United States Patent [19]

McAnalley et al.

[11] Patent Number: 5,106,616

[45] Date of Patent: Apr. 21, 1992

[54] ADMINISTRATION OF ACEMANNAN

[75] Inventors: Bill H. McAnalley, Grand Prairie; Robert H. Carpenter, Bastrop; Harley R. McDaniel, Dallas, all of Tex.

[73] Assignee: Carrington Laboratories, Inc., Irving, Tex.

[21] Appl. No.: 229,164

[22] Filed: Aug. 5, 1988

Related U.S. Application Data

[63] Continuation-in-part of Ser. No. 144,872, Jan. 14, 1988, Pat. No. 4,851,224, which is a continuation-in-part of Ser. No. 869,261, Jun. 5, 1986, Pat. No. 4,735,935, which is a continuation-in-part of Ser. No. 810,025, Dec. 17, 1985, abandoned, which is a continuation-in-part of Ser. No. 754,859, Jul. 12, 1985, abandoned, which is a continuation-in-part of Ser. No. 750,321, Jun. 28, 1985, abandoned, which is a continuation-in-part of Ser. No. 649,967, Sep. 12, 1984, abandoned, which is a continuation of Ser. No. 375,720, May 7, 1982, abandoned.

[51] Int. Cl.$^5$ .................. A61K 45/05; A61K 31/715
[52] U.S. Cl. ................................ 424/85.2; 514/54; 514/885
[58] Field of Search ................... 424/85.2; 514/54, 885

[56] References Cited

U.S. PATENT DOCUMENTS 4,555,987 12/1985 Tumlinson ..................... 100/118

OTHER PUBLICATIONS

Gowda et al., "Structural Studies of Polysaccharides From *Aloe vera,*" Carbohy. Res. 72:201–205, 1979.

*Primary Examiner*—John W. Rollins
*Attorney, Agent, or Firm*—Johnson & Gibbs

[57] ABSTRACT

Acemannan has now been discovered to be a potent inducer of Interleukin 1 (Il-1) and prostaglandin $E_2$ ($PGE_2$) production by human peripheral blood adherent cells in culture. Il-1 has been shown to be an important macrophage product and is associated with influencing the activity and production of T lymphocytes, fibroblasts, B lymphocytes and endothelial cells. Acemannan has no demonstrated toxicity, and acts as an adjuvant and immunoenhancer. Administration of an amount of acemannan sufficient to stimulate monocytes and macrophages not only produces Il-1 and $PGE_2$ but also stimulates phagocytosis, increases antibody production, enhances antiviral activity in the serum and, in those patients with AIDS/ARC, produces defective HIV virus.

Acemannan has been shown to affect the rate of virus production in viral vaccine master seed cultures by accelerating the rate of viral replication. In addition, acemannan is a potent adjuvant to viral vaccines in chickens. Acemannan has also shown specific antitumor activity against sarcoid tumors in horses.

7 Claims, 13 Drawing Sheets

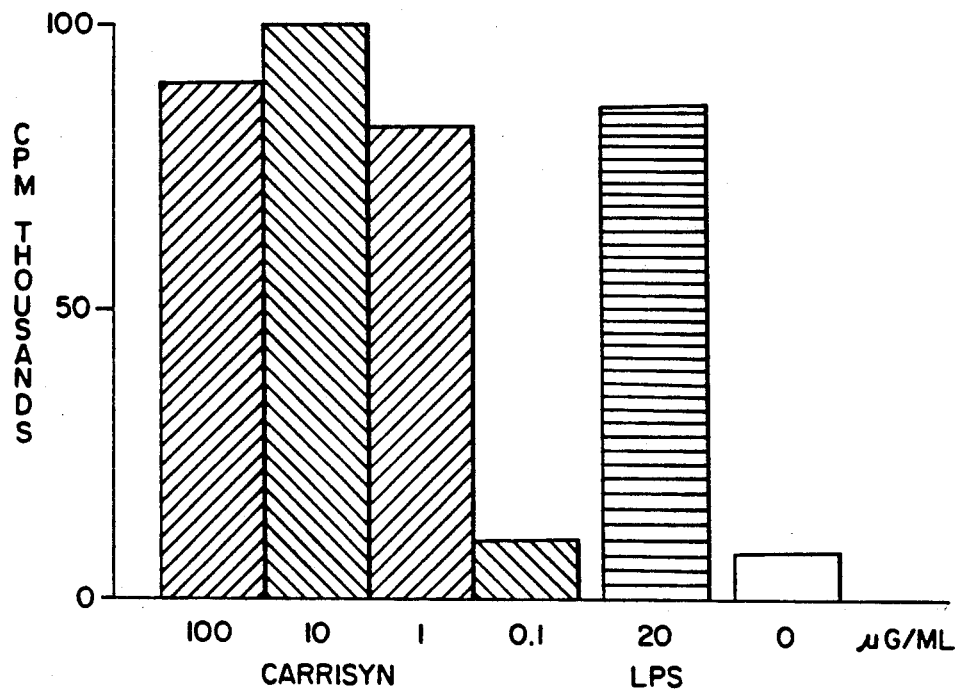
FIG. 3 PRODUCTION OF IL-1 BY HUMAN ADHERENT PBL STIMULATED WITH CARRISYN THYMOCYTE ASSAY
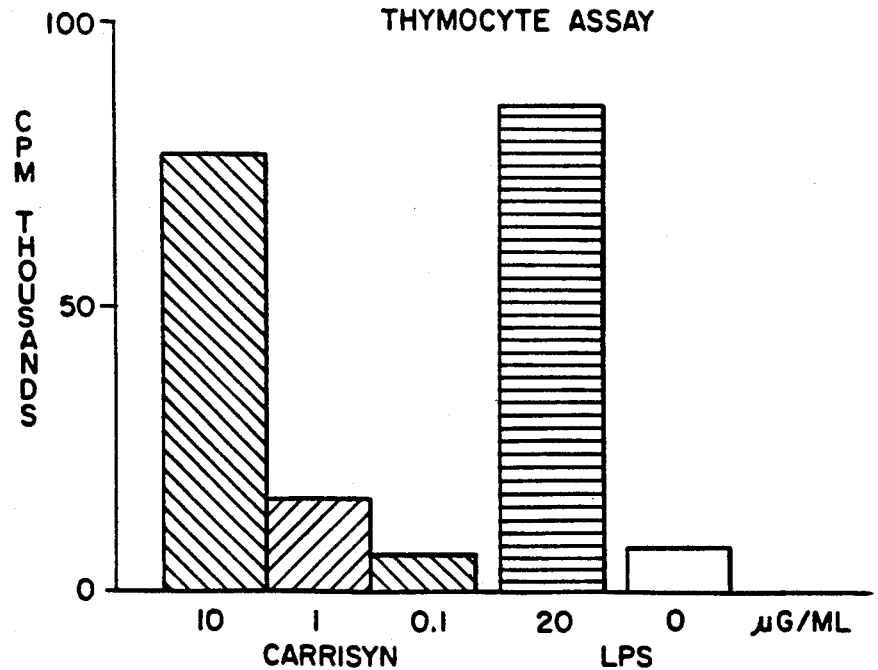
FIG. 4 PRODUCTION OF IL-1 BY HUMAN ADHERENT PBL STIMULATED WITH CARRISYN THYMOCYTE ASSAY △ PRE AND POST TREATMENT T-4 HELPER CELL COUNTS FOR 10 PATIENTS PREDICTED FOR POOR RESPONSE TO TREATMENT

O AVERAGE ABSOLUTE T-4 CELL COUNT FOR ALL PATIENTS PRE AND POST TREATMENT

X PRE AND POST TREATMENT T-4 CELL COUNT AVERAGE FOR 16 PATIENTS PREDICTED FOR GOOD RESPONSE TO TREATMENT

■ AVERAGE - ALL PATIENTS TREATED WITH ALOE DRINK

△ M.W.R. 10 PATIENTS PREDICTED FOR POOR RESPONSE TO TREATMENT

○ M.W.R. AVERAGE ALL PATIENTS TREATED

✕ M.W.R. AVERAGE OF 16 PATIENTS PREDICTED FAVORABLE RESPONSE TO ALOE DRINK

FIG. 22

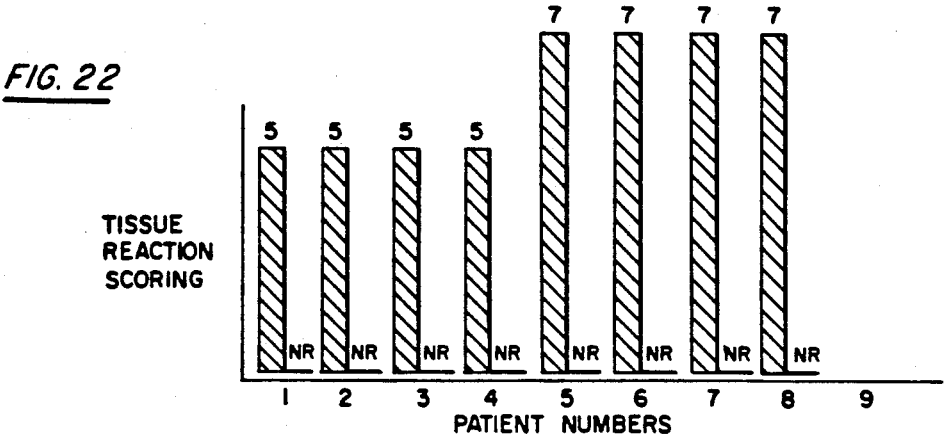

TISSUE REACTION SCORING

▨ PRIOR TO ACEMANNAN THERAPY
▤ MAXIMAL RESPONSE TO ACEMANNAN

NR - NOT REPETED, PATIENT REFUSED EXAM.
---- - PATIENT REFUSED BOTH EXAMS

FIG 23

| CASE No. | PATIENT INITIALS | AGE | SEX | CHART NUMBER | DATE OF ACEMANNAN TREATMENT AND DOSAGE | | CLINICAL SCORING TOTAL | | ENDOSCOPIC SCORING TOTAL | | HISTOLOGICAL TISSUE TOTAL | |
|---|---|---|---|---|---|---|---|---|---|---|---|---|
| | | | | | PRE RX | END RX | PRE | POST | PRE | POST | PRE | POST |
| 1 | S.D. | 24 | F | 137467 | 12/24/85 50mg QID | 7/1/86 | 7 | 1/7/86 0 | 5 | NR | 5 | NR |
| 2 | S.T. | 35 | F | 117736 | 12/23/85 100mg QID | 9/-/86* | 3 | 12/30/86 | 3 | 6/27/86 1 | 5 | NR UNTIL FLARE |
| 3 | G.M. | 30 | M | 102050 | 12/30/85 100mg QID | 9/-/86* | 4 | 12/1/86 0 | 5 | 2/1/86 0 4/12/86 4th FLARE | 4/6/85 3 | 2/1/86 ? |
| 4 | J.M. | 33 | F | 144205 | 6/3/86 250-500mg BID | 9/-/86* | 3 | 7/29/86 1 | 5 | NR | 5 | NR |
| 5 | B.T. | 34 | F | 142280 | 4/17/86 100mg QID | 9/-/86* | 4 | 5/8/86 1 | 2 | NR | 7 | NR |
| 6 | F.C. | 14 | M | 137696 | 1/20/86 CARALOE | 9/-/86* | 5 | 12/20/86 0 | 12/14/85 5 | NR | 8 | NR |
| 7 | M.C. | 26 | M | 141907 | 4/9/86 50mg QID | 9/-/86* | 5 | 6/26/86 1 | 4 | NR | 8 | NR |
| 8 | S.R. | 32 | M | 144108 | 6/6/86 200-250mg QID | 9/-/86* | 3 | 7/15/86 1 | 2 | NR | 7 | NR |
| 9 | K.G. | 46 | M | O.P. | 4/15/86 50mg QID | 5/15/86 | 7 | 0** | | | | |

\* -IND PUT ON HOLD BY INVESTIGATOR DUE QUESTIONS FROM FDA & FDA HOLD ON AIDS IND
\*\*-NO FLARE FOR 2 YEARS, LONGEST INTERVAL IN LAST 20 YEARS
NR-PATIENT DID NOT RETURN

ADMINISTRATION OF ACEMANNAN

RELATED APPLICATIONS

The present application is a continuation-in-part of U.S. application Ser. No. 144,872, filed Jan. 14, 1988, now U.S. Pat. No. 4,851,224 and entitled "Process for Preparation of Aloe Product", the entire contents and disclosure of which are hereby specifically incorporated by reference. Said U.S. application Ser. No. 144,872 is a continuation-in-part of U.S. application Ser. No. 869,261, entitled "Processes for Preparation of Aloe Products, Products Produced Thereby and Compositions Thereof", granted on Apr. 5, 1988, as U.S. Pat. No. 4,735,935, the entire contents and disclosure of which are also hereby specifically incorporated by reference. Said U.S. application Ser. No. 869,261 corresponds to International Application No. PCT/US86/01335 filed Jun. 20, 1986, and published under International Publication No. WO 87/00052 on Jan. 15, 1987, the entire contents and disclosure of which are also hereby specifically incorporated by reference. Ser. No. 869, 261, filed Jun. 5, 1986, was a continuation-in-part of U.S. application Ser. No. 810,025 filed Dec. 17, 1985 (now abandoned), which was a continuation-in-part of U.S. application Ser. No. 754,859 filed July 12, 1985 (now abandoned), which was a continuation-in-part of U.S. application Ser. No. 750,321 filed Jun. 28, 1985 (now abandoned), which was a continuation-in-part of U.S. application Ser. No. 649,967 filed Sept. 12, 1984 (now abandoned), which was a continuation of U.S. application Ser. No. 375,720 filed May 7, 1982 (now abandoned). Application Ser. No. 810,025 was entitled "Processes for Preparation of Aloe Products and Products Produced Thereby". Applications Ser. Nos. 754,859; 750,321; 649,967; and 375,720 were entitled "Process for Preparation of Aloe Vera Products".

BACKGROUND OF THE INVENTION

A. Field of the Invention

This invention pertains to the field of processing aloe plants and removing portions of said plant for processing same into compositions for topical and internal applications and compositions of matter comprising said portions of aloe and uses thereof.

B. Description of the Prior Art, and Other Information

Aloe vera is not a cactus plant, as widely believed, but rather a member of the lily family. There are about 360 species of aloe plants known. Harding, *Aloes of the World: A Checklist, Index and Code, Excelsa* 9: 57–94 (1979). They seem to thrive in hot, arid areas and are widely scattered from the Mediterranean Sea, Middle East, Africa, China, Japan, Mexico and the southern U.S.A. A few of the important species used for their medicinal properties are *Aloe barbadensis* Miller (aloe vera), *A. arborescens, A. plicatilis, A. vahombe, A. saponaria, A. africana, A. ferox* and *Aloe perryi.* Reynolds, *Aloes of Tropical Africa and Madagascar,* The Trustees, The Aloe Book Fund, Mbabane Swaziland. However, *A. barbadensis* Miller is generally recognized as the "true aloe" because of its wide use and, reportedly, most effective healing power, although in Japan, *A. arborescens* Miller traditionally has been used as a folk remedy for various ailments ranging from gastrointestinal disorders to athlete's foot.

Aloe vera is a perennial plant with turgid green leaves joined at the stem in a rosette pattern. The leaves of a mature plant may be more than 25 inches long with saw-like spikes along their margins.

Slicing the leaf transversely as shown in FIGS. 1 and 2 reveals the outer walls of the epidermis (3) covered with thick cuticles. Beneath the epidermis (3) is the mesophyll which is differentiated into chlorenchymal cells and thinner walled cells known as parenchyma. The parenchymal cells harbor a transparent mucilaginous jelly (1). The vascular bundles (2) with inner bundle sheath cells contain the yellow sap, which has laxative properties, and are sandwiched between the two major cells. Needle-shaped crystals of calcium oxalate, produced as a metabolic by-product in plant cells, are found mostly at the central portion of the leaf.

Aloe vera contains two major liquid sources, a yellow latex (exudate) and the clear gel (mucilage). The dried exudate of *Aloe barbadensis* Miller leaves is referred to as aloe. The commercial name is Curacao aloe. It is composed mainly of aloin, aloe-emodin and phenols. Bruce, *South African Medical Journal,* 41: 984 (1967); Morrow et al., *Archives of Dermatology,* 116: 1064–1065 (1980); Saleh et al., *Corrosion Prevention & Control,* 9–10 (1983); Mapp et al., *Planta Medica,* 18: 361–365 (1970); Rauwald, *Archives Pharmazie,* 315: 477–478 (1982). A number of phenolics, including anthraquinones and their glycosides, are known to be pharmaceutically active. Bruce, *Excelsa* 5: 57–68 (1975); Suga et al., *Cosmetics and Toiletries,* 98: 105–108 (1983).

The mucilaginous jelly from the parenchymal cells of the plant is referred to as Aloe vera gel. There are generally no anthraquinones to decompose and cause discoloration of the gel unless the gel is contaminated by an improper processing technique.

Aloe vera gel is about 98.5% water by weight. More than 60% of the total solid is made up of polysaccharides of carbohydrate origin. Organic acids and inorganic compounds, especially calcium oxalate, account for the remainder of the solid.

Whole leaves, exudates and fresh gels of Aloe plants have been used for a variety of human afflictions. Evidence of their use as a medicinal remedy can be traced to the Egyptians of 400 BC. Aloe vera was also used to embalm the dead, as well as to protect the embalmers from the death-causing agent. Other early civilizations used aloe vera for skin care, to relieve insect stings and bites, to treat scratches and ulcerated skin, to promote wound healing, to prevent hair loss and as a purgative. It was the traditional medicine of many cultures as an anthelmintic, cathartic and stomachic and was used inter alia for leprosy, burns and allergic conditions. Cole et al., *Archives of Dermatology and Syphilology,* 47: 250 (1943); Chopra et al., *Glossary of Indian Medicinal Plants,* Council of Scientific and Industrial Research, New Delhi; Ship, *Journal of the American Medical Association,* 238:1770(1977); Morton, *Atlas of Medicinal Plants of Middle American Bahamas to Yucatan,* Charles C. Thomas Publisher, 78–80 (1981); Diez-Martinez, La Zabila, *Communicado N).* 46 *Sobre Recursos Bioticos Potenciales del Pais,* INIREB, Mexico (1981); Dastur, *Medicinal Plants of India and Pakistan;* D. B. Taraporevala Sons & Co., Private Ltd., Bombay 16–17 (1962).

Aloe vera has enjoyed a long history of lay acceptance as possessing "curative" or "healing" qualities. Over the last few years, numerous books and articles meeting scientific standards have been written on Aloe vera. Organizations such as the Aloe Vera Council and recognized medical institutions, through publications and case-histories of physicians, veterinarians and other scientists, have given credence to the "aloe phenomenon". Aloe vera has been featured extensively in the field of dermatology, especially for treating radiation-caused skin conditions. Mackee, *X-Rays and Radium in the Treatment of Diseases of the Skin*, 3rd Ed., Lea and Febiger, Philadelphia, 319-320 (1938); Rovatti et al., *Industrial Medicine and Surgery*, 28: 364-368 (1959); Zawahry et al., *Quotations From Medical Journals on Aloe Research*, Ed. Max B. Skousen, Aloe Vera Research Institute, Cypress, Calif., 18-23 (1977); Cera et al., *Journal of the American Animal Hospital Association*, 18: 633-638 (1982). The body of scientific literature documenting medical applications in digestive problems, as a virucidal, bactericidal and fungicidal agent and in gynecological conditions is extensive and has been adequately reviewed by Grindlay and Reynolds (Journal of Ethnopharmacology, 16: 117-151 (1986)).

The importance of chemicals found in aloes is indicated by the fact that they have been listed in every known national pharmacopeia. *U.S. Pharmacopeia*, 20th Revision, The National Formulary, 15th Edition, United States Pharmacopeial Convention, Inc., Rockville, Md., Jul. 1, 1980. However, the U.S. Pharmacopeia describes the yellow sap drug portion of aloes but not the mucilage. The fresh unpreserved gel is about 98.5-99.2% water. The total solid that remains after the water has been removed ranges from 0.8 to 1.5%. The mucilage, sugars, fiber, proteins, ash, fats, aloin and resin are the major constituents of the solid. Robson et al., *Journal of Burn Care Rehabilitation*, 3: 157-163 (1982). Compositions that include enzymes, organic acids, inorganic salts, amino acids and alkaloids have been noted. Rowe et al., *Journal of the American Pharmaceutical Association*, 30: 262-266 (1941); Roboz et al., *Journal of the American Chemical Society*, 70: 3248-3249 (1948); Waller et al., *Proceedings of Oklahoma Academy of Science*, 58: 69-76 (1978). Depending on the way in which the leaves are processed, mucilage and sugars are the major components of the dehydrated gel. The sugars found are galactose, glucose, mannose, rhamnose, xylose and uronic acids. Although conflicting reports have been observed, the mucilage is mainly composed of mannan or glucomannan. Eberendu et al., *The Chemical Characterization of Carrisyn TM* (in preparation); Mandal et al., *Carbohydrate Research*, 87: 249-256 (1980b); Roboz et al., *Journal of the American Chemical Society*, 70: 3248-3249 (1948); Gowda et al., *Carbohydrate Research*, 72: 201-205 (1979); Segal et al., *Lloydia*, 31: 423 (1968).

Prior to this work, the controversy over the identity of the active substance(s) in Aloe vera had not been settled. It is therefore important to clearly distinguish between the components present in the gel and those found in the exudates. A larger part of the gel is a mucilage of mainly polysaccharide nature with minor amounts of various other compounds. It has been observed that in some of the activities observed there may be some synergistic action between the polysaccharide base and other components. Leung, *Excelsa* 8: 65-68 (1978); Henry, *Cosmetics and Toiletries*, 94: 42-50 (1979). For example, several workers report that the effective components for wound healing may be tannic acid (Freytag, *pharmazie*, 9:705 (1954)) and a kind of polysaccharide. Kameyama et al., Japanese Patent #7856995 (1979). Mackee, supra, noted that the gel, not the rind or the exudate, was responsible for the beneficial effects in the treatment of radiation burns, and he stressed the importance of using fresh leaves for effective treatment. Polysaccharides degrade with time, and certain molecular weight sizes may be necessary to elicit a specified pharmacological response. Goto et al., *Gann*, 63: 371-374 (1972).

There are many examples in the literature that polysaccharides can exhibit pharmacological and physiological activities without help from other components. G. Gialdroni-Grassi, *International Archives of Allergy and Applied Immunology*, 76 (Suppl. 1): 119-127 (1985); Ohno et al., *Chemical and Pharmaceutical Bulletin*, 33: 2564-2568 (1985); Leibovic et al., *Chemico-Biological Interactions*, 60: 191-200 (1986); Ukai et al., *Chemical and Pharmaceutical Bulletin*, 31: 741-744 (1983); Leibovici et al., *Anticancer Research*, 5: 553-558 (1985). One such example relates to development of atherosclerosis. Hyperlipidemia in the general population and especially in familial hypercholesterolemia is associated with coronary heart disease and death. In countries where dietary fiber intake is high, atherosclerosis appears to be uncommon. Trowell et al., Editors, *Refined Carbohydrate Foods and Disease*, London, Academic Press, 207-209 (1975). Pectin and guar are reported to lower cholesterol in normal and hyperlipidemic patients. Kay et al., *American Journal of Clinical Nutrition*, 30: 171-175 (1977). Locust bean gum, a polysaccharide composed of mannose and galactose, decreased the plasma lipoprotein cholesterol concentrations in both normal and familial hypercholesterolemic subjects. Zavoral et al., *American Journal of Clinical Nutrition*, 38: 285-294 (1983). Addition of guar gum to carbohydrate meals decreased the postprandial rise of glucose in both normal and diabetic subjects. Jenkins et al., *Lancet*, 2: 779-780 (1977). Kuhl et al., (*Diabetes Care*, 6 (2): 152-154 (1983)) demonstrated that guar gum exhibited glycemic control of pregnant insulin-dependent diabetic patients.

The anti-tumor activity of polysaccharides has been widely reported. Polysaccharides prepared from *Lentinus cyathiformis* are known to increase hosts' defense against tumors. Rethy et al., *Annales Immunologiae Hungaricae*, 21: 285-290 (1981). There are several reports that polysaccharides from mushroom, yeast or bacterial extracts can elicit a high degree of host defense activity against viral and tumor infestations. Chihara et al., 222: 687-688 (1969); Shwartzman, *Proceedings of the Society for Experimental Biology and Medicine*, 29: 737-741 (1932); Rethy, X. *International Congress of Microbiology; Moscow*, 642 (1966). Suzuki et al. (*Journal of Pharmacobio-Dynamics*, 7: 492-500 (1984) also reported anti-tumor activity of a polysaccharide fraction (GF-1) extracted from cultured fruiting bodies of a fungus, *Grifoloa frondosa*. This fraction showed equivalent, high levels of inhibiting activity when administered intraperitoneally (IP), intravenously (IV) and intratumorally (IT). However, oral administration (PO) was not effective. The GF-1 fraction also exhibited anti-tumor action against the solid form of Meth A fibrosarcoma and MM 46 carcinoma in mice. Lentinan, which is a 6-branched $\beta$-(1-3)-linked glucan similar to GF-1, was ineffective against Meth A fibrosarcoma. Chihara, The antitumor polysaccharide Lentinan: an overview; "Manipulation of Host Defense Mechanisms"; ed. by Aoki et al., *Excerpta Medica*, North Holland, 1-16 (1981); Sasaki et al., *Carbohydrate Research*, 47: 99-104 (1976). Synthesized branched polysaccharides were reported to demonstrate activities against tumors. Matsuzaki et al., *Makromol. Chem.*, 186: 449 (1985). Matsuzaki et al. (*Makromol. Chem.*, 187: 325-331 (1986)) synthesized branched polysaccharides, which showed significant activities, from ivory nut mannan (B-(1-4)-D-mannopyranose) and B-(1-4)-linked glucomannan. A partially acetylated linear B-(1-3)-D-mannan extracted from fruit bodies of *Dictyophoria indusiata* Fisch, also exhibited anti-tumor activity. Hara et al., *Carbohydrate Research*, 111: 143-150. It appears that anti-tumor action depends on the type of polymer main chain and its degree of polymerization, because B-(1-3)-glucan-type polymers show higher anti-tumor activity than B-(1-4)-glucan and hemicellulosic polymers. Matsuzaki et al., *Makromol. Chem.*, 187: 325-331 (1986). A carboxymethylated derivative of B-(1-3)-glucan obtained from bacterial culture filtrate caused severe cell loss from established sarcoma 180 tumors within 2 hours after the injection of the derivative. Baba et al., *Journal of Immunopharmacology*, 8: 569-572 (1986). The same author observed a compensatory increase in polymorphonuclear leukocytes due to injection of the substance. Incidentally, bestatin, a dipeptide known to possess immune-modulating and anti-tumor activity (Ishizuka et al., *Journal of Antibiotics*, 32: 642-652 (1980)), influenced neither the tumor yield nor the polymorphonuclear leukocyte count. Baba et al., supra.

There are numerous reports on the anti-tumor effect of sulfated polysaccharides, including heparin (Jolles et al., *Acta Univ. Int. Cancer*, 16: 682-685 (1960); Suemasu et al., *Gann*, 61: 125-130 (1970)), sulfated laminaran and dextran. Jolles et al., *British Journal of Cancer*, 17: 109-115 (1963).

Yamamoto et al. (*Japanese Journal of Experimental Medicine*, 54: 143-151 (1984)) reported enhancement of anti-tumor activity of a fucoidan fraction by further sulfation. The sulfated product demonstrated activity against L-1210 leukemia. The authors postulated that the mechanism of the anti-tumor action might be due partly to inhibition of invasive growth of L-1210 cells, as a result of electrostatic repulsion between the tumor cell and mesothelial cells. Yamamoto et al., supra. Polysaccharides with sulfate groups are also reported to be human T cell mitogens and murine polyclonal B cell activators. Sugawara et al., *Microbiological Immunology*, 28: 831-839 (1984). Generally, homopolysaccharides of high molecular weight with sulfate groups possess these properties. Dorries et al., *European Journal of Immunology*, 4: 230-233 (1974); Sugawara et al., *Cell Immunology*, 74: 162-171 (1982).

It has been reported that glucan extracted from the yeast *Saccharomyces cerbisiae* is a modulator of cellular and humoral immunity. Wooles et al., *Science* 142: 1078-1080 (1963). The polysaccharide also stimulated proliferation of murine pluripotent hematopoietic stem cells, granulocyte macrophage colony-forming cells and cells forming myeloid and erythroid colonies. Pospisil et al., *Experientia*, 38: 1232-1234 (1982); Burgaleta et al., *Cancer Research*, 37: 1739-1742 (1977). Maisin et al. (*Radiation Research*, 105: 276-281 (1986)) also reported that IV administration of a polysaccharide induced protection of murine hematopoietic stem cells against x-ray exposure, thereby decreasing the mortality of the mice so exposed.

V. Lackovic et al., (*Proceedings of the Society for Experimental Biology and Medicine*, 134: 874-879 (1970)) took yeast cell-wall and extracted all constituent matter leaving only "mannans" that he found were responsible for the induction of α-interferon production by monocytes. The "purified mannans" alleged to be responsible for the physiologic response had a molecular weight of 5,500-20,000 Daltons. He theorized the mannans stimulated mouse peritoneal macrophages to produce the α-interferon. He does state that his mannans isolated showed no toxicity and "they are poor antigens". There was no mention by Lackovic et al. of the use of these "purified mannans" for antiviral activity or for IL-1 stimulation. We submit Lackovic et al.'s "purified mannans" comprised an assortment of unknown and unidentified substituted and unsubstituted mannans.

Seljelid et al., (*Experimental Cell Research*, 131: 121-129 (1981)) have observed that insoluble or gel-forming glycans activated macrophages in vitro, whereas the corresponding soluble glycans did not. They postulated that the orientation in which the glycan was presented to the mononuclear phagocyte was decisive for activation. Bogwald et al. (*Scandinavian Journal of Immunology*, 20: 355-360 (1984)) immobilized glycans that had a stimulatory effect on the macrophages in vitro. This led the authors to believe that the spacial arrangement of the glycan was decisive for the effect on the macrophages in vitro. A purified polysaccharide isolated from *Candida albicans* induced an antibody response by human peripheral blood lymphocytes in vitro. Wirz et al., *Clinical Immunology and Immunopathology*, 33: 199-209 (1984). There were significant differences between the anti-Candida antibodies in sera of normal and Candida-infected individuals. Wirz et al., supra.

The antiviral activity of polysaccharides and polysaccharides linked to peptides has been observed. Suzuki et al., *Journal of Antibiotics*, 32: 1336-134 (1979). Suzuki et al., supra, reported an antiviral action of peptidomannan (KS-2) extracted from culture mycelia of *Lentinus edodes*. Both oral (PO) and intraperitoneal (IP) administration increased the peak serum interferon titer, which protected mice against viral infections. This was different from dextran phosphate (DP-40) (Suzuki et al., *Proceedings of the Society for Experimental Biology and Medicine*, 149: 1069-1075 (1975)) and 9-methylstreptimidone (9-MS) (Saito et al., *Antimirobial. Agent & Chemotherapy*, 10: 14-19 (1976)), which induced higher titers of interferon in mice only if administered intravenously (IV) or intraperitoneally (IP).

Anti-inflammatory activity of Aloe vera gel has been widely reported by both oral testimonies and respected scientific journals. Rubel (*Cosmetics and Toiletries*, 98: 109-114 (1983)) discussed fully the possible mechanism of the anti-inflammatory effect of aloe gel. Ukai et al., (*Journal of Pharmacobio-dynamics*, 6: 983-990 (1983)) noted anti-inflammatory activity of polysaccharides extracted from fruit bodies of several fungi. The polysaccharides demonstrated a significant inhibitory effect on carrageenan-induced edema. One of the polymers, O-acetylated-D-mannan (T-2-HN), in addition demonstrated a more marked inhibitory effect than phenylbutazone on scald hyperalgesia. Ukai et al., supra. The assertion that the polysaccharide is free from protein and lipids strongly suggests that the anti-inflammatory effect is due to the acetylated mannan only. Other researchers have also reported anti-inflammatory effects of complex polysaccharides (Saeki et al., *Japanese Journal of Pharmacology*, 24: 109-118 (1974)), glycoproteins (Arita et al., *Journal of Pharmacology.*, 24: 861-869 (1974)) and sulfated polysaccharides (Rocha E. Silva et al., *Biochemical Pharmacology*, 18: 1285-1295 (1969)).

Literature reports that polysaccharides possess pharmacological and physiological activities continue to flood the pages of well respected scientific journals. It is therefore not illogical that the mucilaginous gel of the Aloe vera, which is essentially a polysaccharide, holds the secret to Aloe vera's medicinal properties. The discrepancies over whether the polysaccharide is a glucomannan, mannan, pectin or of some other composition are a result of chemical purification steps. By processing aloe according to the present invention, a partially acetylated polymannose has been consistently isolated as the major polysaccharide with pharmacological activity. Yagi et al., (*Planta Medica*, 31: 17-20 (1977)), using a slightly modified extraction method, isolated acetylated mannan (aloe mannan) from *Aloe arborescens* Miller var. *natalensis*. Ovodova (*Khim. Prior. Soedin*, 83: 93833 (1975)), however, earlier isolated pectin as the main component of the same aloe species.

As discussed above, the biological activity of polysaccharides has been recognized for many years. Polysaccharide materials recovered from plants, yeast and bacteria have demonstrated direct biological activity by eliciting an increase in host defense systems. This reaction is primarily manifested by increased host surveillance for other antigenic substances. Polysaccharides serve as adjuvants (Freund's, etc.) and immunomodulators. They also function as unique T cell-independent antigens. Both cellular and humoral immunity may be affected, and increased phagocytosis of infectious organisms and tumor cells has been observed, as has enhanced production of immunoglobulins.

The structure of these immunologically active polysaccharides and the types of structural variations appear to be the factors that control their potency and toxicity. Their mode(s) of action remain poorly understood; however, recent evidence indicates that several polysaccharides induce lymphocytes and macrophages to produce a wide range of immunologically active substances. The composition of the present invention possesses all of the attributes of these immunologically active substances; it is among the most potent of all known biologically active polysaccharides but differs in that no toxicity has been observed. It also manifests specific antiviral activity through alteration of viral glycoprotein synthesis.

SUMMARY OF THE INVENTION

It is therefore an object to provide a method of activation, induction and enhancement of the production of Interleukin I and prostaglandin $E_2$ by monocyte and macrophage peripheral blood adherent cells comprising administering an amount of acemannan sufficient to effect monocyte and macrophage stimulation.

It is a further object to provide a method of activation, induction and enhancement of the production of Interleukin I and prostaglandin $E_2$ by monocyte and macrophage peripheral blood adherent cells wherein acemannan is administered orally in the range of about 0.1 mg/kg bwt/day to about 100.0 mg/kg bwt/day, or administered by injection in a range of about 0.001 mg/kg bwt/day to 10 mg/kg bwt/day.

It is a still further object to provide a method of stimulating macrophage phagocytosis in a mammal, comprising administering an amount of acemannan sufficient to effect monocyte and macrophage stimulation.

It is a still further object to provide a method of producing an antiviral effect in mammals, comprising administering an amount of acemannan sufficient to effect monocyte and macrophage stimulation.

It is a still further object to provide a method of producing defective virus in humans, comprising administering an amount of acemannan sufficient to effect monocyte and macrophage stimulation and alter viral replication metabolism in virus infected cells.

It is a still further object to provide a method of producing defective virus in master seed cultures for vaccine production, comprising adding a predetermined amount of acemannan to a master seed culture sufficient to produce altered viral replication.

It is a still further object to provide a method of immunoenhancement of vaccine by production of an adjuvant effect, comprising adding a predetermined amount of acemannan to a vaccine product in the range of about 0.001 mg to 10 mg per vaccine dose.

It is a still further object to provide a method of treatment of tumor in a mammal, comprising administering to a mammal an amount of acemannan sufficient to effect monocyte and macrophage stimulation, enhance natural killer cell activity, and specific tumor cell lysis by white cells and/or antibodies.

It is a still further object to provide a method of inducing acemannan into the Golgi apparatus of (i) a noninfected cell to give rise to altered glycoproteins which provide said cell with protection from viral infection or (ii) a virus-infected cell to produce glycoproteins which destroy or inhibit a viral expression in said infected cell, comprising inducing a sufficient amount of acemannan into a cell to alter glycoproteins at the surface of a cell.

It is a still further object to provide a method of inducing acemannan into the Golgi apparatus of a virus-infected cell to produce glycoproteins which destroy or inhibit a viral expression in said infected cell wherein acemannan is induced into the cell in an amount sufficient to render the virus noninfected.

It is a still further object to provide a method of inducing acemannan into the Golgi apparatus of a virus-infected cell to produce glycoproteins which destroy or inhibit a viral expression in said infected cell wherein the cell is virus-infected, and acemannan is introduced into the cell in an amount sufficient (i) to cause a broad spectrum of specific antibodies to be produced which provide a broader immunological response than the cell had prior to induction, and (ii) to enhance the rate of broad spectrum antibody production.

It is an object of this invention to provide a method of providing in a mammal increased amounts of mannose to intra- and extracellear cell metabolic pathways to correct malabsorption and mucosal cell maturation syndromes in man and animals comprising the step of administering to a mammal an amount of acemannan sufficient to provide additional mannose for the synthesis of glycoprotein by accelerating Michaelis-Menten constants for mannosyl transferase activity.

It is a further object to provide a method of inducing in a mammal a virus-infected cell to express altered viral glycoprotein antigens on its surface which will initiate an antibody dependent cell cytolysis (ADCC) by cytotoxic lymphocytes, comprising the method of administering to a mammal an amount of acemannan into the infected cell sufficient to produce altered viral glycoproteins and cause said altered viral glycoproteins to be expressed on the surface of infected cells which exposes them to humoral antibodies.

It is still another object to provide a method of incuding acemannan into a human to produce an effect to reduce the symptoms associated with multiple sclerosis, comprising the method of administering to a human an amount of acemannan sufficient to reduce plaque formation and to induce plaque replacement with functional tissue in the central nervous system cells.

Finally, a method of inducing acemannan into a mammal to reduce the symptoms associated with inflammatory bowel disease, comprising the method of administering to a mammal an amount of acemannan sufficient to resolve lesions associated with inflammatory bowel disease by increasing tissue regeneration of ulcers in said lesions and by reduction of auto-immune immunoglobulin in local tissues of said lesions.

Carrisyn TM is the brand name given by the assignee of the instant invention to the purified ethyl alcohol extract of the inner gel of the leaves of *Aloe barbadensis* Miller. The active component of Carrisyn TM extract has been designated "acemannan" by the United States Adopted Name Council. Not less than 73% of Carrisyn TM extract is acemannan; Carrisyn TM extract comprises generally about 73% to 90% acemannan. Carrisyn TM extract is produced, generally, by removing the outer sheath of the leaf, then removing and processing the inner filet, or mucilage, by pH adjustment, ethanol extraction, freeze drying and grinding. See Ser. No. 144,872 filed January 1988, a continuation-in-part of Ser. No. 869,261 (now U.S. Pat. No. 4,735,935), the disclosures of which are incorporated herein by reference. By processing in this manner, we believe that no covalent bonds are altered, and therefore no toxic compounds are created. These manufacturing steps were developed to overcome problems presented by the fact that traditional aloe product producers suffered from an inability to standardize and stabilize the polysaccharides. Carrisyn TM extract is a fluffy white amorphous powder, which is poorly soluble in water and dimethyl sulfoxide, and insoluble in most other organic solvents. This powder contains not less than 73% of a polysaccharide consisting essentially of linear (1-4)-D-mannosyl units. The polysaccharide is a long chain polymer interspersed randomly with acetyl groups linked to the polymer through an oxygen atom. The generic name for the polymer is acemannan. The degree of acetylation is approximately 0.913 acetyl groups per monomer as determined by the alkaline hydroxamate method (Hestrin, *Journal of Biological Chemistry*, 180: 249-261 (1949)). Neutral sugars linkage analysis indicates that attached to the chain, probably through a α(1-6) linkage, is a D-galactopyranose in the ratio of approximately one for every seventy sugars. The 20:1 ratio of mannose to galactose indicates that galactose units are also linked together, primarily by a β(1-4) glycosidic bond. The chemical structure of acemannan may be represented as follows:

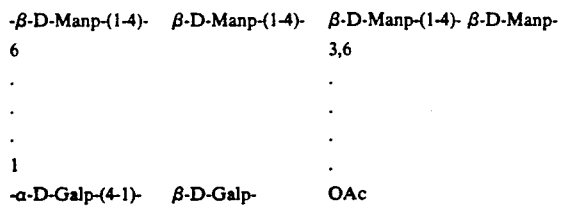

A detailed description of the methods utilized to produce the composition and to arrive at this structure is disclosed in U.S. Pat. No. 4,735,935 and U.S. Pat. application Ser. No. 144,872, the disclosures of which are incorporated herein by reference.

Acemannan is a biologically active component of Carrisyn TM extract and is in th same chemical class as the T-independent antigens LPS (lipopolysaccharide), FICOL, dextran and levan. The T-independent antigens share a number of common properties. In particular, they are all quite negatively charged, large polymeric molecules with repeating antigenic determinants, and many of them possess the ability, at high concentrations, to activate B cell clones other than those specific for that antigen. That is, they exhibit polyclonal B cell activation. See Roitt, Brostoff and Male, *Immunology*, 1986, the C. V. Mosby Company, St. Louis, pages 8.3 and 8.4.

At least 73% of the purified bulk Carrisyn TM extract consists of polysaccharide polymers of acemannan having molecular weights greater than 10,000 Daltons.

Acemannan is not mutagenic or blastogenic in in vitro test systems. In vivo toxicology studies on acemannan include a 91 day subchronic oral toxicity study in dogs and a 180 day chronic oral toxicity study in rats. In these studies no toxic effects were noted in dogs receiving up to 825 mg/kg of acemannan per day. No clinical, gross pathologic or toxic effects were noted in rats receiving up to 38,475 ppm acemannan in their feed.

In pilot studies, administration of acemannan to dogs has caused an absolute monocytosis in blood samples taken for complete white blood cell counts and morphology differential. Within 2 hours after oral administration of high doses of acemannan, large activated monocytes appeared in circulation.

Acemannan has now been discovered to be a potent inducer of interleukin 1 (Il-1) and prostaglandin $E_2$ ($PGE_2$) production by human peripheral blood adherent cells in culture. The instant invention is believed to be the first practical non-toxic stimulator of Il-1 release. Interleukin 1 is an important macrophage product reported in the literature to influence the activity and production of T-lymphocytes, fibroblasts, B-lymphocytes and endothelial cells. L. J. Old, "Tumor Necrosis Factor", SCIENTIFIC AMERICAN, (April 1988). See also G. Wittman, "Die Absorption von DEAE Dextranan die OberHäche von Schweinelymphozyten", Zentralblatt fur Veterinarmedizin Reihe B, 26: 577-590 (1979) and C. A. Dinarello, "Biology of Interleukin 1", FASEB Journal, 2: 108-115 (1988) for the biological properties of Il-1. Il-1 induces fibroblast proliferation which helps wound healing. Il-1 also: (1) decreases the utilization of fat for energy and induces a loss of appetite—it may act as a slimming aid; (2) enhances bone marrow activity—it may be therapeutic in individuals whose bone-marrow is depressed; and (3) enhances the immune system in general.

A series of experiments with mixed lymphocyte cultures (MLC) has shown that acemannan increases the alloantigenic response of these lymphocytes in a dose-related fashion. Incubation of acemannan with monocytes permitted monocyte-driven signals to enhance the T lymphocyte response to lectin. Related studies on acemannan's effects on MLC has shown an increase in phagocytosis and natural killer cell activity. Thus in these in vitro test systems acemannan is not toxic and is an immunoenhancer.

Utilizing an ELISA kit sensitive to nanogram per milliliter quantities, detectable acemannan concentrations have been detected in the blood of dogs after IV administration. The concentration declines quite rapidly and becomes barely detectable after 195 minutes. Uptake and concentration of acemannan within the macrophage/monocyte system has also been determined.

Acemannan is a potent stimulator of monocytesecreting monokines and also causes HIV-infected monocytes to produce altered glycoproteins (GP-120) by a mechanism similar to Swainsonine. Tulsiani et al., *Journal of Biological Chemistry*, 257: 7936-7939 and Elbein et al., *Proceedings of the National Academy of Sciences of the United States of America*, 78: 7393-7397. Acemannan is phagocytized and apparently pumped to the Golgi/-glycoprotein apparatus of the monocyte where it interferes directly with glycoprotein synthesis.

Acemannan increases the amount of IgM and IgG antibodies to viral antigens and decreases the time required for their appearance in serum. In addition, acemannan enhances alloresponsiveness, increases phagocytosis and increases natural killer cell activity of mixed lymphocyte cultures. These mechanisms can account for the increase in absolute CD-4 (i.e., T-4) counts in HIV-infected patients as well as for the reduction in symptoms associated with their concurrent infections. Physicians treating HIV-infected patients with acemannan have reported a highly significant reduction in HIV symptoms and other symptoms associated with concurrent infections.

The mode of action of acemannan against HIV infection is seen as a combination of:

Destruction of infected or defective cells due to activation of killer cells.
Production of noninfective, defective HIV virus.
Enhanced antibody production.
Increased host surveillance for other antigenic substances.

Early information on twenty AIDS/ARC patients currently being treated with Carrisyn TM extract in a placebo-controlled clinical trial indicates that no evidence of toxicity, adverse reactions or side effects has been noted.

Acemannan has been reported to have antiviral activity against herpes and measles viruses in viral plaque assays using VERO monolayers as target cells. The drug did not prevent the infection of susceptible lymphocyte cultures by HIV virus or inhibit reverse transcriptase activity in vitro.

Acemannan is believed to be useful in the treatment of AIDS, colitis, decubitus ulcers, tumors and for use as a novel and extraordinarily potent adjuvant. Acemannan is also useful in a wide variety of applications from vaccine efficacy enhancement to prevention and treatment of diseases caused by pathogenic organisms that create immune deficiencies or that escape immune detection to become established in otherwise healthy persons. Acemannan is also useful in the prevention and treatment of the common cold and several strains of influenza.

Fifteen AIDS patients drinking 20 ounces per day of the stabilized aloe juice (which contained from 388 to 1109 mg acemannan per liter) for up to 350 days reported a significant reduction in symptoms associated with HIV infection without adverse effects. Another group of 26 HIV-infected patients consuming 20 ounces of aloe drink per day were observed for 90 days, and no adverse effects were noted.

Tabulation and analysis of data from HIV-positive patients treated with aloe drink indicated that in 15 patients observed for 350 days the average Walter Reed (modified) scores fell from 5.6 to 1.5. In a second group of 26 patients, observed for 90 days, average scores fell from 2.98 to 1.76. The absolute CD4 lymphocyte counts in these same two groups of patients rose from 350 to 446 and from 217 to 259, respectively. Analysis of serum core antigen concentrations revealed no significant trend. Examination of data from the 15-patient group led to development of criteria for predicting the response of HIV patients to treatment with aloe drink. When these criteria were applied prospectively to the second group of HIV patients who had also been treated with aloe drink, the criteria were found to be generally predictive.

DESCRIPTION OF THE FIGURES

FIGS. 3-5 are graphs depicting production of Interleukin 1 (Il-1) and Interleukin $1_B$ in human AB serum by Human Adherent Peripheral Blood Leukocytes (PBL) stimulated with Carrisyn TM extract at various concentrations, as determined by Thymocyte or ELISA Assay.

FIG. 5 shows the production of IL-1 by human adherent PBL stimulated with Carrisyn as determined by ELISA Assay.

FIG. 22 is a graph showing mucosal biopsy evaluation of patients with inflammatory bowel syndrome in response to acemannan therapy.

FIG. 23 is a chart showing acemannan pilot patient study tabular summary of patients with inflammatory bowel disease in response to acemannan therapy.

DETAILED DESCRIPTION OF THE PREFERRED EMBODIMENTS

A. Toxicology

Figure 1:
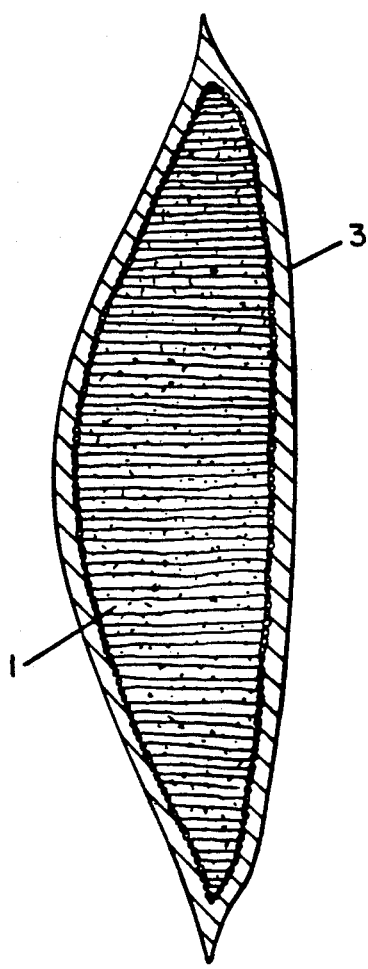
FIGS. 1, 1A and 2 show cut-away portions of an Aloe vera leaf.
Figure 1A:
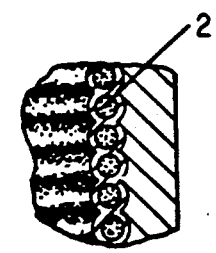
Figure 2:
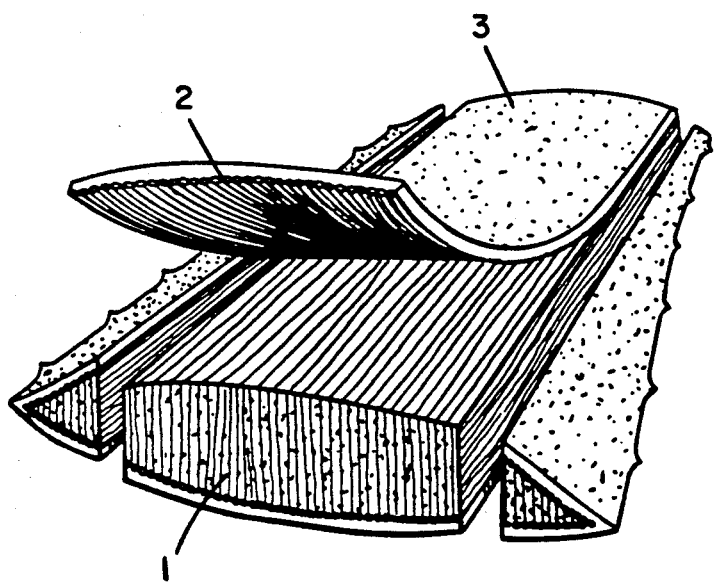

The toxicological effects of acemannan have been studied in in vivo and in vitro systems.

Acemannan was examined for mutagenic activity in the Ames *Salmonella* microsome assay. The assays were conducted with *Salmonella typhimurium* strains TA1537, TA1538, TA98 and TA100, in both the presence and absence of an Aroclor 1254-induced rat-liver metabolic activation system. Acemannan was not shown to be mutagenic when tested according to these assay procedures.

Acemannan was placed into several in vitro test systems to evaluate toxicity to cells, the blastogenic response caused by acemannan and the effects on HIV virus and HIV-susceptible cells. In preliminary studies, a 1:10 dilution of the 0.2% stock solution (0.02% final dilution) was chosen as the nontoxic concentration, using H-9 cells as target cells. A 1:20 dilution was chosen as the nontoxic level using normal leukocytes as the target cells. Toxicity studies showed that acemannan at a concentration of 0.02% had a slight stimulatory effect on group B cells when compared to the media control group A cells. The drug tested together with phytohemagglutinin (PHA) (group D) had a slight inhibitory effect as compared to PHA alone (group C). These observed differences were not considered significant.

The tested concentration of acemannan did not substantially inhibit infection of target cells by HIV-I (formerly HTLV-III). Some target cells were infected with virus on day 0 and treated with drug from day three post infection (group III). Additionally, other target cells were treated with drug three days prior to viral infection, and cultivation was continued in the presence of drug (group IV). In both instances, the viral infection and/or replication appeared similar, even to a high concentration of positive control virus, as demonstrated by comparison of reverse transcriptase results of day seven and day 14. Virus treated under the second condition may have demonstrated somewhat reduced infectivity, but due to an overestimation of drug activity, insufficient dilutions of treated sample points did not allow an exact endpoint for the test to be obtained.

A 14-day toxicity study to determine an appropriate dosage range was performed using Sprague-Dawley weanling rats to assess toxicological effects of Carrisyn TM extract (acemannan) and, subsequently, to determine dose levels for a 6-month subchronic study. Dose levels of 0, 6000, 12500, 25000 and 50000 ppm of Carrisyn TM extract were administered in the feed to groups of 10 male and 10 female rats. All animals were observed daily for signs of toxicity, morbidity and mortality. Body weight and feed consumption were determined weekly. Clinical chemistry and hematology parameters were determined at termination. Terminal necropsies were conducted over a 2-day period. Organ weights were obtained, and selected tissues were retained in 10% neutral buffered formalin. Compound-related changes were not observed in clinical signs, body weight, feed consumption, hematology, clinical chemistry or organ weights. Gross pathological examination revealed incidental non-compound-related changes. Sprague-Dawley rats, therefore, appear to tolerate up to 5% of Carrisyn TM in the diet for at least 2 weeks duration.

In another study with rats, 60 Charles River CD rats were randomly assigned to six treatment groups of five males and five females each for use in a 2 week (14 day) exploratory oral dosing study of acemannan. Carrisyn TM extract (acemannan) was suspended in cottonseed oil carrier in amounts that provided the following dose (treatment) levels: 500, 1000, 2000, 3000 and 5000 mg/kg bwt/day. Controls received only cottonseed oil carrier. All treatments were administered orally by gavage at a constant volume of 20 mL/kg bwt. All animals were observed at least twice daily for overt signs of toxicity, sickness or mortality and detailed observations were made at least once per week. Individual body weights and food consumption values were recorded weekly. Five rats died including one male in each of the 2000 and 5000 mg/kg/day groups and two females in the 5000 mg/kg/day group. The one female in the 1000 mg/kg/day group that died showed no prior abnormal signs. Of the other four rats, at least two showed abnormal respiration, red staining around the mouth, decreased defecation and were cold to the touch. Distended abdomens were noted during the second week in all males in the highest dose group and in two females in the 3000 mg/kg/day group. Abnormal respiration was observed in most animals, particularly during the second week, at the 1000, 2000, 3000 and 5000 mg/kg/day dosage levels and was noted in one male at the 500 mg/kg/day dosage level. Body weights and/or food consumption were reduced in the 5000 mg/kg/day male and female rats compared to those of the control group. The respiratory distress and distended abdomen noted in some animals were considered related to the physical nature of the test article/cottonseed oil mixture rather than to the chemical nature of the test article; it seems probable that the rats were unable to digest the material well enough to allow the stomach to empty normally. The distended stomach intruded into the chest to cause respiratory distress.

In acute studies, five male and five female rats were dosed once orally with the test article, Carrisyn TM extract (acemannan), at a dose level of 5000 mg/kg. The test article was administered as a w/v suspension in cottonseed oil in a volume of 20 mL/kg. Criteria evaluated for treatment effect during the 15-day study period were mortality, pharmacotoxic signs, body weights and pathology, determined by gross necropsy examinations. There was no evidence of test article-related toxicity noted in any animal. The $LD_{50}$ value of the test article was found to be greater than 5000 mg/kg when administered once orally to male and female rats. Identical results were obtained when the same procedure was carried out using five male and five female mice.

A 91-day subchronic toxicity study in dogs was undertaken with Carrisyn TM extract (acemannan) to assess toxicological responses following oral administration. The study consisted of four groups of four male and four female purebred beagle dogs receiving Carrisyn TM extract (acemannan) at oral doses of 0, 100, 400 or 1,500 mg/kg/day. The material was administered daily by incorporating the quantity of test article required to provide the assigned dose for each dog into an amount of feed expected to be consumed by the dog during a 1-hour feeding period. The quantity of feed offered was based on feed consumption on the prior day. All dogs received the theoretical dose ±10%. The dogs were weighed during pretest, at weekly intervals and prior to terminal necropsy. Feed consumption was measured daily starting 1 week prior to dosing. Morbidity, mortality and signs of toxicity were monitored daily, prior to initiation and during dosing. Clinical chemistry, electrophoresis, hematology and urinary parameters were determined during pretest, after 45 days and prior to termination. After the 86th dose, blood samples were collected from high-dose and control dogs at periodic intervals over a 24-hour period to assess possible changes in white blood cell parameters. All dogs survived to the end of the study. At termination the dogs were given a complete gross necropsy examination; selected organs and tissues were saved in 10% neutral buffered formalin, and hematoxylin and eosin-stained slides of these tissues were examined microscopically. Selected organs from all dogs were weighed for determination of absolute and relative organ weights, as well as for calculation of organ-to-brain weight ratios. Clinical signs noted in treated animals were considered incidental findings or of comparable severity as those seen in the control animals and were not believed related to compound administration. Compound-related changes were not observed in body weight, feed consumption, clinical chemistry, urinary or electrophoretic parameters. A possible trend towards an increase in absolute numbers of monocytes was noted during the 24-hour serial bleed, but only in male dogs. Mean absolute and relative organ weights were similar in control and compound-treated dogs. All gross and microscopic pathological findings were considered incidental and not related to compound administration.

B. Pharmacology

The pharmacological actions and effects of acemannan have been studied in a variety of in vitro and in vivo test systems.

Carrisyn TM extract (acemannan) was evaluated in vitro for anti-HIV and anti-mannosidase activity. In the test system used, acemannan was not shown to have antiviral activity. Acemannan protected only 43% of MT-2 human lymphocytes in culture at the highest tested concentration (1000 mcg/mL) and demonstrated no inhibition of mannosidase. Acemannan did not prevent glycosylation (GP-120 formation) but did produce a number of radiolabeled bands of higher and lower molecular weight glycoproteins of HIV-I. Acemannan also showed cell growth-promoting activity at all concentrations: vital dye uptakes were 140% and 158% of controls. Although exhibiting no direct activity against HIV, acemannan was concluded to have immune-stimulating properties.

Acemannan was tested in a standard antiviral plaque assay against *Herpes simplex* virus, and an antiviral effect was noted at an acemannan concentration of 0.771 mg/mL, a concentration that is readily achievable in certain immune system cells.

When measles virus was pre-incubated with various concentrations of acemannan prior to addition of the virus to susceptible cultures of VERO (Green monkey kidney) cells, the acemannan-treated virus did not infect the VERO monolayer, as evidenced by the absence of cytopathic effects (CPE) of the virus at a threshold concentration of 2.5 mg/mL. Complete absence of CPE was achieved at 5 mg/mL of acemannan in the virus inoculum. Saliva incubated with acemannan increased the antiviral activity of acemannan in VERO cell monolayer culture exposed to measles virus. Saliva-treated acemannan showed as much as a five-fold increase in antiviral activity; thus oral amylase enzyme exposure may enhance acemannan antiviral activity. In another evaluation, VERO cells were incubated with media containing 40 TCID/mL of measles virus for various periods of time (0.5 to 6 hours) prior to the addition of 5 mg/mL of acemannan. However, in this assessment, incubation with acemannan after cells were exposed to the measles virus did not protect the VERO cells from infection.

Polymer chain lengths were separated by hollow fiber size exclusion ultrafiltration to explore the effect on herpes-virus of various polymer chain lengths of acemannan. The resulting chain length fractions were evaluated according to their ability to inhibit infection of VERO cell cultures by *Herpes simplex* II virus. In this system, the greatest degree of protection to the VERO cells was afforded by the fractions containing molecular weights of less than 3000 daltons.

VERO cell monolayers were treated with 5 mg/mL of acemannan in the media for 2, 4, 8 and 12 hours. The monolayers were then washed with media containing no acemannan. Forty TCID/mL of measles virus were added to each treated monolayer, and the cultures were examined for cytopathology after 5 days. Pretreatment of the VERO cells with acemannan did not prevent measles virus infection.

Laboratory procedures were devised to quantitate the amount of virus produced by HIV-infected peripheral blood lymphocytes and to assess their infectivity. Included in this profile were an anti-complement immunofluorescent (ACIF) stain as an indicator that the cells had accepted the HIV infection, an HIV p24 core antigen assay to assess the amount of antigen being produced and a reverse transcriptase assay as a quantitative indicator of biologically active, infectious viral antigen production. Cell density and trypan blue dye exclusion tests were used to evaluate the growth and viability of the cells in culture. Results of these experiments suggested that acemannan did not directly, via reverse transcriptase inhibition, inhibit the replication of HIV.

A study was performed using human peripheral blood monocyte cell cultures and $C^{14}$-labeled acemannan to track the incorporation or adsorption of acemannan into a biological system (Example 23, infra). In this study, detectable amounts of $C^{14}$-labeled acemannan were adsorbed or ingested by human peripheral monocyte/macrophage cells. Peak incorporation occurred at 48 hours. The $C^{14}$-labeled acemannan at a concentration of 5 mg/mL was not cytotoxic to the monocyte/macrophage cells, and the digested cell mass in weight/volume (w/v) terms was 760 times greater than the w/v of the digested acemannan solution. These results suggest that the macrophage cell form is capable of intracellular concentration of acemannan at very high levels that are not cytotoxic.

Experiments toward developing an ELISA kit for detection of free acemannan in sera of human patients and animals were conducted on serum samples obtained from a 15-kg dog given 3 mg/kg of acemannan IV. The results indicated that acemannan is detectable in serum and is rapidly cleared from blood. Samples taken 195 minutes after acemannan injection contained very low concentrations.

To assess the suitability of acemannan for parenteral use, two rabbits were given 5 mg of acemannan IV to determine any obvious effect on the rabbit and any change in white blood cell morphology at 1 hour and 2 hours after injection. Acemannan caused no observable clinical change in the physical condition of either rabbit. The blood samples from one rabbit clotted for an unknown reason (probably defective EDTA tubes). A different lot of EDTA tubes was used for the other rabbit, and the blood samples did not clot. The presence of a number of large mononuclear cells on the blood smear slide prepared 2 hours after injection was attributed to acemannan.

A dermal test was performed on rabbits to assess the irritant properties of acemannan after intradermal injection. No cutaneous or systemic reaction was noted in response to any of the test materials after injection of 0.1 mL of a 1 mg/mL test solution.

A pyrogen assay was performed in rabbits in accordance with the pyrogen test protocol outlined in the U.S.P. XXI, Biological Test [151], using a 1 mg/mL injectable solution of acemannan. More frequent temperature measurements were taken than specified in the U.S.P. because of the unknown systemic effects of injected acemannan. Temperature changes in the test animals did not exceed the minimum changes allowed by the U.S.P. protocol; therefore, the solution met the U.S.P. requirements for absence of pyrogens. Acemannan injectable elicited a maximum body temperature increase of 0.3° C., measured in one rabbit. It was noted that this temperature rise occurred 90 minutes after injection. Acemannan is an inducer of Interleukin-1 (Il-1) secretion by macrophages and monocytes in vitro. Since Il-1 is a potent pyrogen, this might explain the minimal, delayed temperature rise in this rabbit.

To evaluate the suitability of acemannan solution for intraarterial use, a dose of 1.5 mL of acemannan injectable (1 mg/mL) was injected without difficulty into the central artery of a rabbit's ear. The tissue supplied by the artery showed no gross changes at 24 hours, 48 hours or 7 days after injection. Even though the injectable acemannan formed a thick suspension of particles, the material was well tolerated by the local tissue and did not occlude the capillaries of the ear tip.

An experiment was also performed to determine if a large dose of acemannan injected IP would elicit signs of discomfort or an increase in temperature. Baseline clinical-physical exams, including rectal temperatures, were collected on two rabbits. The rabbits were given IP injections of either 5 mL of acemannan solution (1 mg/mL) or 5 mL of the same normal saline that was used to dilute and prepare the acemannan test material. The rabbits were examined at 1, 2, 24 and 48 hours after the injection for signs of physical change, discomfort or temperature increase. No reaction to any of the test materials was detected.

To determine the effect of acemannan on human peripheral blood adherent cells, in vitro assays were performed. It was observed that acemannan is a potent inducer of interleukin-1 and prostaglandin $E_2$ production by monocytes and macrophages.

Four mongrel dogs were given single doses of Carrisyn TM extract (acemannan) and observed for changes in clinical signs and laboratory blood parameters. Doses of Carrisyn TM extract administered ranged from 15 to 1500 mg/kg of body weight. A control dog was subjected to placebo administration and manipulation. Subsequently, the same five dogs were assigned to a 93-day oral administration protocol with Carrisyn TM extract. The dose selected was 150 mg/kg/day. In both studies, treated and control dogs exhibited no changes in behavior or in the results of clinical examination. The only measured parameter observed to change with administration of the test article was an increase in the number of circulating monocytes noted during white cell differential counting. Some of these monocytes appeared to be activated because they were larger than other monocytes seen on the blood slides. Necropsy and histopathological examination of all dogs at the end of the studies showed no abnormal findings.

In a study performed to evaluate a possible biological marker (increased numbers of circulating monocytes) for orally administered acemannan in dogs, 20 beagles (10 male and 10 female) were divided into three treatment groups. Carrisyn TM extract (acemannan) was given orally in doses of 0.05, 0.5 or 5.0 mg/kg. Blood smears were examined for total and differential WBC counts prior to acemannan treatment and at 1, 3, 5, 7 and 24 hours after treatment. Total WBC and monocyte counts increased in the 0.5 and 5.0 mg/kg treatment groups. Monocytosis was maximal 7 hours after acemannan administration. The no effect dose level for this potential biological marker was 0.05 mg/kg.

Since acemannan appeared to enhance monocyte function in other experiments, studies were designed to test the capacity of acemannan to enhance immune response to alloantigen and to test whether the potential enhancement is a monocyte driven phenomenon. Acemannan did not enhance lymphocyte response to syngeneic antigens in the mixed lymphocyte culture (MLC), but it more importantly increased alloantigenic response in a dose-related fashion $(2.6 \times 10^{-7} - 2.6 \times 10^{-9} M)$. This effect of acemannan was shown to be a specific response and to occur with in vitro concentrations of acemannan that can also be achieved in vivo. A separate series of mixing experiments demonstrated that acemannan incubation with monocytes permitted monocyte-driven signals to enhance T cell response to lectin. It was concluded that acemannan is an immunoenhancer in that it increases lymphocyte response to alloantigen. It was suggested that the mechanism involves enhancement of monocyte release of Il-1 under the aegis of alloantigen. This mechanism may explain in part the recently observed capacity of acemannan to abrogate viral infections in animal and man.

The effect of Carrisyn TM extract (73%–90% acemannan) was studied in vitro to ascertain its effect on phagocytic function. Carrisyn TM extract was injected IP into CBA mice, and peritoneal and splenic macrophages were collected 3 days later. Thioglycolate and saline were similarly tested as positive and negative controls, respectively. The macrophages were incubated with sheep red blood cells (SRBC) as ingestion particles, in the presence and absence of anti-SRBC titers, and phagocytosis was measured histologically as percent cells that ingested SRBC. Although nonspecific phagocytosis was increased slightly after Carrisyn TM extract treatment, phagocytosis was significantly increased in the presence of antibody. In the presence of complement, Carrisyn TM-stimulated antibody-mediated phagocytosis was increased to an even greater extent. These results indicate that Carrisyn TM extract increases the number of macrophages and enhances their phagocytic activity. Such responses may contribute to its effectiveness as a stimulant of wound healing and as an anti-infectious agent.

Carrisyn TM extract (acemannan)-stimulated macrophages were also compared to thioglycolate-stimulated and control macrophages in vivo and in vitro to determine effects of stimulated phagocytes on nonspecific tumor death. Thioglycolate-stimulated macrophages incubated with $Cr^{51}$ target cells released $Cr^{51}$ at an average of 2800 cpm, whereas Carrisyn TM extract-labeled cells released radioactivity at an average of 3100 cpm. There was no statistical difference between these groups. Nonstimulated macrophages released in the range of 2800 cpm. However, macrophages stimulated with Carrisyn TM extract in vitro had a $Cr^{51}$ release of 21,000 cpm. This indicated two obvious facts. Carrisyn TM extract does not induce a long standing cytolytic effect, and its activation can occur in a relatively short time in tissue culture. The percent cytotoxicity was parallel to the cpm. A subsequent experiment was performed using the cytotoxic assay over time. The cytotoxic effect was shown to begin as early as 6 hours after stimulation and to increase to its maximum in 12 hours. The mechanism of this activation was not investigated. The data shown in these investigations indicated that Carrisyn TM extract (acemannan) may have an important role in nonspecific therapy of cancer.

Twenty healthy cats, 16–20 weeks old, with no previous vaccinations for any feline diseases, were selected for a study of the efficacy of acemannan in the treatment of feline viral rhinotracheitis. Ten cats were treated with a single oral dose (15 mg/kg) of Carrisyn TM extract (acemannan), and the others served as non-acemannan (positive) controls. Four hours after acemannan administration, the cats were exposed intranasally to feline rhinotracheitis virus. All untreated cats developed signs of the disease, whereas only two of the 10 acemannan-treated animals exhibited clinical signs. Furthermore, the two affected cats in the latter group experienced a milder course of the disease.

C. Mode of Administration

The physical properties of acemannan allow it to be formulated and incorporated into all pharmaceutical dosage forms that are known to those skilled in the art. The biopharmaceutical and toxicological properties of acemannan permit it to be used in tissues and organs of living organisms and to be administered over a wide range of doses.

Acemannan may be administered orally, parenterally, topically and locally, in a daily dosage of 0.001 mg/kg to 100 mg/kg body weight per day.

Mixed with suitable auxiliaries acemannan may be compressed or filled into solid dosage units such as pills, tablets and coated tablets or processed into capsules. These oral dose forms would be administered at a dosage of about 0.1 mg/kg to 100 mg/kg of body weight per day.

By means of suitable liquid vehicles acemannan can be injected in solutions, suspensions or emulsions. These products would be administered at a rate of 0.001 mg/kg to 10 mg/kg of body weight per day. As an adjuvant component of a vaccine or other product, acemannan would be used at a rate of 0.001 to 10 mg per unit dose of adjuvanted product.

As a general rule, acemannan becomes effective in humans when administered in any form by which at least 10 $\mu$g/kg bwt/day is available.

Topical administration of acemannan can be in the form of a processed gel, cream, lotion, solution, ointment or powder. These formulations could contain up to 90% acemannan.

EXAMPLE 1

Production of Interleukin-1 and PGE$_2$ by Human Adherent Peripheral Blood Leukocytes Stimulated with Carrisyn

A. Induction of Il-1 Production

Figure 5:
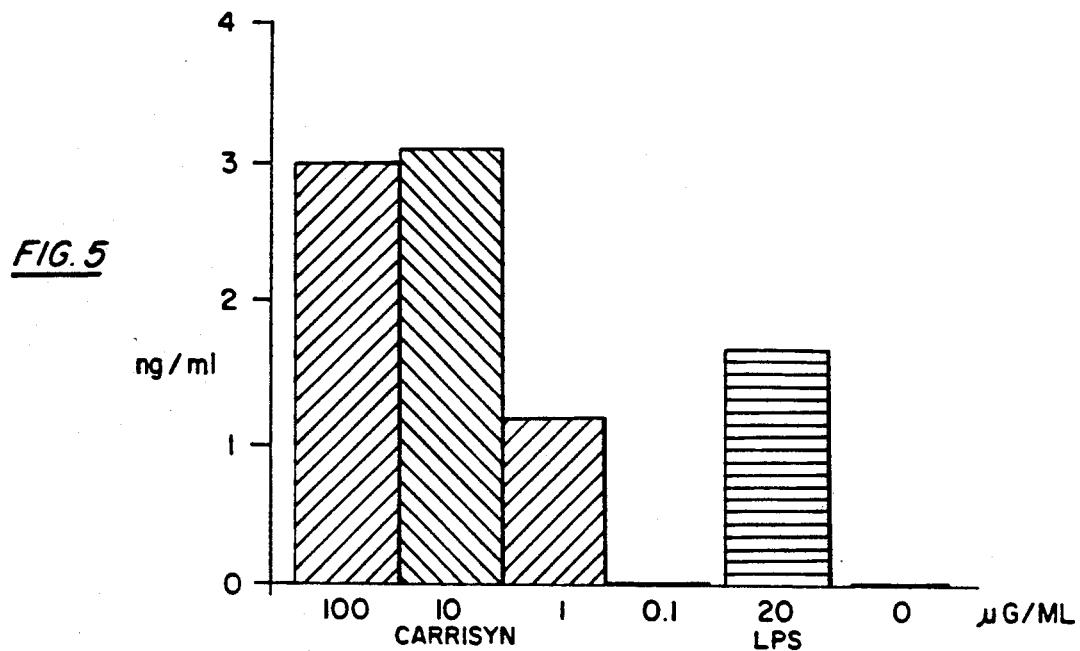

Human mononuclear cells were separated from heparinized whole blood by density-gradient centrifugation in Ficoll-Hypaque (Pharmacia, Sweden). After washing, cells were resuspended at a concentration of $2 \times 10^6$ mL in RPMI-1640 with 25 mM Hepes, supplemented with 50 U/mL penicillin, 50µg/mL streptomycin and 2 mM L-glutamine. Two mL aliquots of the cell suspensions were dispensed into each well of a six-well plate and incubated for 1 hour at 37° C. in a 5% CO$_2$-humidified atmosphere. After removal of non-adherent cells, adherent cells were washed three times with the medium described above. Two mL of medium supplemented with 5% pooled human AB serum was added to each well. Cultures were stimulated with Carrisyn TM extract at different concentrations as shown in FIGS. 3-5. Simultaneous controls with lipopolysaccharide (LPS) from *E. coli* (Sigma 0111:B4) at a final concentration of 20 µg/mL, and without any addition (background), were included. The cultures were incubated at 37° C. as described above for 24 hours. Supernatants were harvested, centrifuged to remove cells and dialysed against 500 volumes of PBS for 48 hours (changed once), followed by 4 hours of dialysis against 20 volumes of RPMI-1640 with 25 mM Hepes, antibiotics and L-glutamine as described. Supernatants were frozen at −20° C. until Il-1 activity was evaluated.

B. Il-1 Determination in Supernatants

Two different procedures were used to assay Il-1: (1) the thymocyte proliferation assay and (2) an ELISA assay specific for Il-1.

1. Thymocytes from C3H/HeJ mice 5-8 weeks old were used. A homogeneous cell suspension was prepared in minimum essential medium (MEM) supplemented with 5% FCS, 100 U/mL penicillin, 50 µg/mL streptomycin, 2 mM L-glutamine and $5 \times 10^{-5}$ M 2-mercaptoethanol. The cell concentration was adjusted and dispersed into 96-well plates at $1 \times 10^6$ cells/well. PHA was added to each well at a concentration of 10 µg/well. Samples were diluted serially and a volume of 25 µL was added to each well, starting from 1:10 final dilution. Every dilution was tested in quadruplicate. Plates were incubated at 37° C. in a humidified atmosphere with 5% CO$_2$ for 72 hours and were pulsed with [H3]-thymidine (0.5 µCi/well) during the last 16 hours. Cells were harvested onto fiberglass filters with an automatic cell harvester, and radioactivity was measured by standard scintillation procedures. FIGS. 3 and 4 show results from two separate experiments. Results are represented as cpm of thymidine incorporation by thymocytes in response to the supernatants at a final 1:10 dilution.

2. Two-site "Sandwich" ELISA for Il-1. This procedure has recently been described in *Journal of Immunology*, 138: 4236-4242 (1987), the disclosure of which is hereby specifically incorporated herein by reference. See also U.S. Pat. No. 3,654,090 and U.S. Pat. No. RE 31,006 to Schuurs et al. Briefly, monoclonal purified antibody Il-1-H6 against Il-1β, (100 µL/well, 10 µg/mL) was coated on vinyl assay plate wells overnight at 4° C. The wells were washed with PBS/0.5% Thimerosal and counter-coated with 200 µL of 5% non-fat dry milk/0.5% Thimerosal/PBS for 1 hour at room temperature. After washing, 50 µL/well of sample or human recombinant Il-18 standard and 50 µL of another monoclonal antibody against a non-overlapping epitope of Il-1β, biotinylated IIB1-H67 (2 µg/mL) in 1% non-fat dry milk/0.5% Thimerosal/PBS, were added, and the plates were incubated for 2 hours at room temperature. After washing, 100 µL/well of a 1:1000 dilution of streptavidin-peroxidase was added and the plate was incubated for 1 hour. The wells were washed, incubated for 30 minutes in the dark with 100 µL OPD substrate solution, and adsorbance at 450 ηm was measured (FIG. 5).

C. Determination of PGE$_2$

Prostaglandin E$_2$ was evaluated with a radioimmunoassay in the same non-dialyzed supernatants. The antibody to PGE$_2$ (ICN Biomedical, Inc., Costa Mesa, CA) was used according to the manufacturer's instructions.

D. Observations

Representative experiments are shown in FIGS. 3-5 and Table 2. Carrisyn TM extract is a potent inducer of Il-1 production by human adherent peripheral blood leukocytes. At doses between 1 and 10 µg/mL, Carrisyn TM extract induced production of Il-1 comparable to that induced by 20 µg/ml LPS, which is the reference inducer of Il-1 production. Carrisyn TM extract in the same dose range also induced the production of PGE$_2$ at levels comparable to those induced by 20 µg/mL LPS (positive control).

TABLE 1

Induction of prostaglandin E$_2$ synthesis by human peripheral blood adherent cells stimulated by Carrisyn TM and by lipopolysaccharide (LPS).

| Experiment Number | Stimulator | PGE$_2$ ng/ml |
|---|---|---|
| 198 | 0 | 0 |
|  | LPS 20 µg/mL | 2.6, 3.9 |
|  | Carrisyn 10 µg/mL | 3.5 |
|  | Carrisyn 1 µg/mL | 0 |
| 148 | 0 | 0 |
|  | LPS 20 µg/mL | 0.5, 1.3 |
|  | Carrisyn 10 µg/mL | 0.7 |

EXAMPLE 2

The Effect of Carrisyn TM on Phagocytosis in Vitro

The effect of Carrisyn TM extract (73% acemannan) was studied in to ascertain its effect on phagocytic function. CBA mice were injected intraperitoneally with Carrisyn TM extract, and peritoneal and splenic macrophages were collected 3 days later. Thioglycolate and saline were similarly tested as positive and negative controls, respectively. The macrophages were incubated with sheep red blood cells (SRBC) as ingestion particles in the presence and absence of anti-SRBC titers, and phagocytosis was measured histologically as percent cells that ingested SRBC. Although non-specific phagocytosis was increased slightly after Carrisyn TM extract treatment, phagocytosis was significantly increased in the presence of antibody. In the presence of complement, Carrisyn TM -stimulated antibody-mediated phagocytosis was increased to an even greater extent. These results indicate that Carrisyn TM extract may increase the number of macrophages and enhance their phagocytic activity. Such responses may contribute to effectiveness as a stimulant of wound healing and as an anti-infectious agent.

A. Methods and Materials

Carrisyn TM extract (acemannan) was stored at room temperature in its dried form. The amount needed for each experiment was weighed out and microwaved in 2-minute exposures at 600 watts of power. It was then transferred to a sterile plastic centrifuge tube and microwaved for one additional minute. The material was diluted in cell culture medium (RPMI-1640) to the desired concentration.

Phagocytic Cells: Mouse spleen cells were obtained from BALB/c mice purchased from Harlan Sprague-Dawley. The mice were killed by $CO_2$, and their spleens were removed aseptically. Subsequently, the cells were separated into adherent and non-adherent populations by nylon wool column fractionation according to the method of *Journal of Immunology*, 71: 220-225 the disclosure of which is hereby specifically incorporated herein by reference. Adherent cells were determined by microscopic analysis, a described below, to be macrophages (monocytes) and lymphocytes in a ratio of 4 to 1. After single-cell suspensions were obtained by monolayer disruption, both adherent and non-adherent single cell preparations were placed on ficoll-hypaque and centrifuged to obtain a mixture of lymphocytes and macrophages.

Blastogenesis Assay: A standard blastogenesis assay was set up as outlined below. The mitogen used in the assay was PHA-P obtained from Burroughs Wellcome. As indicated for individual experiments, the cultures were maintained for 72 hours in a 5% $CO_2$, humidified atmosphere. Tritiated thymidine was added during the last 6 hours of the culture. The cell concentrations per well using flat bottom microtiter tissue culture plates were $5 \times 10^5$ mouse cells/0.2 mL. Cells were first deposited in the wells followed by the addition of Carrisyn TM extract or mitogen. A stimulation index (S.I.) was calculated using the formula:

$$S.I. = \frac{\text{cpm experimental} - \text{cpm background}}{\text{cpm control} - \text{cpm background}}$$

Cell Staining: Briefly, smears of cells were stained by non-specific esterase stain as follows. Approximately $2 \times 10^6$ cells in 2 drops were mixed with 2 drops of fetal calf serum and 4 drops of a fixative solution consisting of a mixture of 25 mL of 35% formaldehyde, 45 mL of acetone, 100 mg of $KH_2PO_4$, 10 mg of $Na_2HPO_4$ and 30 mL of water. The slides were incubated with a mixture of 10 mg of naphthyl acetate and 4.5 mg of Fast Blue stain in 1.4 mL of ethylene glycol monomethyl ether with 5 mL of 0.1 M Tris-maleate buffer, pH 7.8 (Wright's stain) *Journal of Histochemistry*, 21: 1-12 (1973)). The stain was allowed to react for 10 minutes, then washed in water for 20 seconds. A counterstain of 0.2 g of Giemsa, 12.5 mL of ethanol and 12.5 mL of glycerol was used for 30 seconds before washing again.

Induction of Peritoneal Macrophage Cells: Saline thioglycolate broth or acemannan was injected IP into female BALB/c mice to induce peritoneal exudate macrophage cells. Induced cells were removed from the peritoneal cavity 3 days post-injection.

Macrophages were washed twice with phosphate-buffered saline (PBS) and covered with 2 mL of fresh medium 0.1 mL of the macrophage suspension was added to each tube. Cultures were placed for 30 to 60 minutes into a 37° C., humidified 5% $CO_2$ 95% air incubator. The cultures were washed twice with PBS and covered with 2 mL of PBS. One of each pair of coverslips was removed with needle-nosed forceps, dipped for 5 seconds only in distilled water and promptly replaced in the culture dish. The PBS was removed, and the cultures were covered with ice-cold glutaraldehyde. After 10 minutes, the glutaraldehyde was removed, and the coverslips were overlaid with distilled water.

Mounted coverslips were examined promptly with the oil immersion lens of a phase contrast microscope. Attachment was scored on the coverslip that was not subjected to hypotonic shock, whereas ingestion was scored on the coverslip that was lysed in distilled water.

Antibody-Dependent and Antibody-Independent Phago-cytosis: Sheep red blood cells (SRBC), obtained from Austin Biologics Laboratory, Austin, Tex., were washed three times in PBS (pH 7.2 ). BALB/c mice were given IP injection of $10^6$ cells and bled on day 14 post injection. Serum was collected, pooled and heat inactivated at 56° C. for 45 minutes. Agglutination titers were determined to be 1024 using round-bottomed microtiter wells.

Antibody-independent phagocytosis was determined by incubation of SRBC (0.5% v/v) with macrophages ($10^6$) in RPMI-1640 containing 20% fetal calf serum (FCS). Slides were prepared at various intervals and stained. The percent macrophages that had ingested red cells was determined visually by counting 200 cells/slide and three slides/animal.

Antibody-dependent phagocytosis was determined using SRBC (0.5% in RPMI 1640 with 20% FCS) mixed with anti-SRBC serum or IgM fraction (minimum titer of 2000). The mixture was incubated for 15 minutes at 37° C., then washed twice in PBS (pH 7.2) and resuspended to the original volume.

Serum Fractionation: Whole serum was fractionated to remove IgM by euglobulin precipitation and dialysis against distilled water. After dialysis at 4° C. for 24 hours, the precipitate was removed by centrifugation at 1500 $\times$ g for 20 minutes, and the supernatant was analyzed by ion electrophoresis and complement-mediated lysis. Less than 5% of the original IgM remained.

B. Results

To evaluate the effect of acemannan on macrophages, the first experiment utilized mouse spleen cells cultured in vitro with acemannan (Table 2).

TABLE 2

PERCENT CELL TYPES BY HISTOLOGICAL EVALUATION OF MOUSE SPLEEN CELLS IN CULTURE

| Time in Culture | Cells[a] | Acemannan (μg/well) | | | |
|---|---|---|---|---|---|
| | | 0.0 | 0.002 | 0.02 | 0.2 |
| 72 hours | macrophages | 30 ± 6 | 32 ± 7 | 41 ± 3 | 45 ± 9 |
| | lymphocytes | 70 ± 5 | 68 ± 8 | 59 ± 3 | 55 ± 6 |
| 96 hours | macrophages | 22 ± 4 | 28 ± 4 | 36 ± 6 | 38 ± 8 |
| | lymphocytes | 78 ± 8 | 72 ± 7 | 64 ± 10 | 62 ± 4 |

[a]Macrophages (monocytes) were determined by esterase staining. The results are expressed as mean ± S.D. The results are from six experiments with 200 cells studied/experiment. "Lymphocytes" are cells that did not stain by esterase and had the appearance of lymphocytes by Wright's stain.

Cultures were incubated for 72 or 96 hours, and at termination of the experiment smears were made and stained by Wright's stain and by the esterase method. The relative percentage of macrophages and lymphocytes was determined. At 72 hours there was a dose-related increase in macrophage numbers from 30% with no acemannan to 45% with 0.2 μg of acemannan per well. Since data are expressed as percent cells, there was a concomitant reduction in the lymphocytes. At 96 hours there was also a dose-related increase in the percentage of macrophages in the presence of acemannan. At 96 hours the cultures with 0.2 μg of acemannan per well showed significant acidosis, as indicated by a yellow coloring. Furthermore, 96-hour cultures had a lower percentage of macrophages, possibly due to the longer time in culture. To relate the acemannan-induced increase in macrophage numbers to a known standard, a similar experiment was conducted with the mitogen PHA-P. Results are shown in Table 3.

TABLE 3

PERCENT CELL TYPES BY HISTOLOGICAL EVALUATION OF MOUSE SPLEEN CELLS IN CULTURE

| Time in Culture | Cells[a] | PHA-P (μg/well) | | | |
|---|---|---|---|---|---|
| | | 0.0 | 0.02 | 0.01 | 0.2 |
| 72 hours | macrophages | 33 ± 8 | 32 ± 6 | 30 ± 6 | 31 ± 5 |
| | lymphocytes | 70 ± 12 | 68 ± 8 | 70 ± 6 | 69 ± 4 |
| 96 hours | macrophages | 18 ± 6 | 21 ± 3 | 26 ± 6 | 25 ± 5 |
| | lymphocytes | 77 ± 10 | 79 ± 4 | 74 ± 8 | 73 ± 6 |

[a]Monocytes were determined by esterase staining. The results are expressed as mean ± S.D. The results are from six experiments. "Lymphocytes" are cells that did not stain by esterase and had the appearance of lymphocytes by Wright's stain.

Although the percentage of macrophages did not change at 72 hours, there was a dose-related increase in macrophages after incubation with PHA-P for 96 hours. By comparison, acemannan was twice as effective as PHA-P. The percentage of macrophages increased a maximum of 16 with acemannan compared to 7 with PHA-P (Tables 2 and 3).

Since acemannan appeared to increase the percentage of macrophages, it was decided to determine if the activity of the phagocytes was also increased. Peritoneal exudate cells from CBA mice given saline, thioglycolate broth or acemannan were used [as phagocytes] with sheep red blood cells as the particles to be ingested (Table 4).

TABLE 4

NONSPECIFIC PHAGOCYTOSIS OF SHEEP ERYTHROCYTES BY PERITONEAL EXUDATE[a]

| | Percent of Phagocytosis[b] | | | | | |
|---|---|---|---|---|---|---|
| | Time (minutes) | | | | | |
| Treatment | 0 | 5 | 10 | 20 | 60 | 120 |
| Saline | 3 ± 3 | 11 ± 6 | 15 ± 10 | 25 ± 9 | 45 ± 12 | 52 ± 15 |
| Thioglycolate | 1 ± 1 | 14 ± 8 | 20 ± 8 | 52 ± 14[c] | 84 ± 32[c] | 89 ± 21[c] |
| Acemannan | 3 ± 2 | 10 ± 6 | 12 ± 8 | 41 ± 18 | 61 ± 18 | 63 ± 23 |

[a]The results were determined by counting 200 cells/slide with two slides/animal. The results are based on two experiments.
[b]Percent phagocytosis indicates the proportion of cells showing erythrocyte ingestion. The results are expressed as mean ± S.D.
[c]Significantly different from saline control group, assessed by the Student's t-test at the 95% confidence level Over a 120-minute period, nonspecific phagocytosis increased from 3% to 52% in saline controls, whereas percent phagocytosis in cells from thioglycolate broth-treated animals rose to 89%. Phagocytosis in acemannan-treated animals rose to 63% at 120 minutes. Acemannan-stimulated phagocytosis was greater than that in controls after 20-120 minutes; however, the differences were not statistically significant.

To determine if the acemannan effect on phagocytosis was antibody-dependent, a similar experiment was performed with anti-SRBC (Table 5).

TABLE 5

ANTIBODY MEDIATED PHAGOCYTOSIS[a]

| Phagocyte Source | Pre-treatment | Antibody Titer (× 10³)[b] | | | |
|---|---|---|---|---|---|
| | | 0 | 2 | 4 | 8 |
| Peritoneum | Saline | 15 ± 8 | 43 ± 10 | 39 ± 9 | 19 ± 11 |
| | Thioglycolate | 49 ± 11 | 89 ± 22 | 80 ± 22 | 58 ± 14 |
| | Acemannan | 36 ± 14 | 73 ± 13[c] | 62 ± 8 | 40 ± 13 |
| Spleen | Saline | 11 ± 4 | 38 ± 9 | 32 ± 11 | 20 ± 4 |
| | Thioglycolate | 29 ± 9 | 73 ± 13 | 54 ± 16 | 38 ± 12 |
| | Acemannan | 21 ± 10 | 60 ± 9[c] | 51 ± 17 | 26 ± 11 |

[a]Phagocytosis is expressed as the mean % of cells showing erythrocyte ingestion ± S.D.
[b]The antibody titer by agglutination was shown to be 1:1024. Pre-treatment and cell sources are discussed in Methods.
[c]Significantly different from saline control, assessed by the Student's t-test at the 95% confidence level.

Sera were inactivated with heat (56° C. for 30 minutes), and the antibody titer used was $2 \times 10^3$, well above the hemagglutination titer. In this experiment, macrophages were obtained from two sources, the peritoneal cavity and the spleen. Again, mice were pre-treated with IP injections of saline, thioglycolate or acemannan. At a titer of $2 \times 10^3$, the phagocytic activity of thioglycolate-induced peritoneal macrophages was twice as great (89% vs 43%) as activity from the saline-induced controls, whereas acemannan-induced macrophages were more active by 30% (73% vs 43%) compared to controls. The difference between phagocytic activity in the acemannan-treated and saline control groups was statistically significant.

Similar results were seen with macrophages obtained from mouse spleens. Phagocytic activity was lower than that of macrophages obtained from the peritoneal cavity, possibly due to manipulations of the spleen cells (see Methods). Again, at a titer of $2 \times 10^3$, acemannan-induced macrophages were significantly higher in phagocytic activity than saline controls at the 95% confidence level; phagocytic activity was similar to control at a titer of $8 \times 10^3$.

To determine the effect of complement (C') on antibody-mediated phagocytosis, an experiment utilizing addition of C' to media was undertaken. (Table 6).

TABLE 6

COMPARISON OF COMPLEMENT-MEDIATED PHAGOCYTOSIS

| Cell Source | Phagocyte Inducer | % Phagocytosis[a] | |
|---|---|---|---|
| | | +C' | −C' |
| Peritoneum | Saline | 24 ± 11 | 18 ± 9 |
| | Thioglycolate | 84 ± 10 | 62 ± 12 |
| | Acemannan | 70 ± 8[b] | 54 ± 4 |
| Spleen | Saline | 18 ± 11 | 16 ± 9 |
| | Thioglycolate | 54 ± 9 | 41 ± 11 |
| | Acemannan | 48 ± 10 | 35 ± 6 |

[a]Phagocytosis is measured as percent uptake of sheep erythrocytes ± S.D. after incubation for 30 minutes. Guinea pig complement was added.
[b]Significantly different compared to −C', assessed by the Student's t-test at the 95% confidence level.

To assure that lysis would not occur, IgM-depleted mouse serum was used (see Methods). The titer utilized was $3 \times 10^3$, as determined by hemagglutinations and the Coombs technique. Cells from both the peritoneal cavity and spleen were more active in phagocytosis with the addition of C' than without C', although the difference was statistically significant only with peritoneal cells induced by acemannan.

Finally, an experiment was performed to differentiate the effect of acemannan phagocytosis and adherence (Table 7).

TABLE 7

COMPARISON OF PHAGOCYTOSIS AND ADHERENCE[a]

| Cell Source[b] | Pre-treatment | Phagocytosis | Adherence |
|---|---|---|---|
| Peritoneum | Saline | 5 ± 8 | 6 ± 4 |
| | Thioglycolate | 12 ± 9 | 23 ± 9[c] |
| | Acemannan | 11 ± 9 | 18 ± 10[c] |
| Spleen | Saline | 8 ± 7 | 14 ± 11 |
| | Thioglycolate | 14 ± 6 | 36 ± 10[c] |
| | Acemannan | 10 ± 8 | 20 ± 7[c] |

[a]Cell mixtures were allowed to incubate for 7 minutes.
[b]Results are reported as percent phagocytes showing phagocytosis or adherence ± S.D. The results are from one experiment with 200 cells scored/animal with three animals used.
[c]Significantly different from saline controls, assessed by the Student's t-test at the 95% confidence level.

In this experiment, antibody to SRBC was used in a titer of $2 \times 10^3$, but the experiment was stopped after 7 minutes. Acemannan-induced macrophages from both the peritoneum and spleen were more efficient in adherence than the saline controls and, as seen previously, less efficient than the thioglycolate-induced group.

C. Discussion

The results indicate that acemannan both directly and indirectly stimulates phagocytosis. The results also indicate that acemannan enhances phagocytosis by macrophages, both non-specifically and specifically, through antibody-mediated reactions. This demonstrates that acemannan has immunostimulatory properties on phagocytes.

EXAMPLE 3

In Vitro Evaluation of Acemannan as an Anti-HIV Agent

A. Effect of Carrisyn TM Extract on HIV Production and Infectivity

Equal-density cultures of washed H9/HTLV-III$_B$ cells were incubated in the presence and absence of various concentrations of Carrisyn TM extract (acemannan) for 2 days. Conditioned culture fluids were then harvested and used to infect cultures of C3 cells. Reverse transcriptase (RT) activity in these culture fluids was also determined. Infection in the C3 cultures was monitored by indirect immunofluorescence for HIV p24 antigen synthesis.

Results are summarized in Table 8.

TABLE 8

| Carrisyn TM (μg/mL) | RT Activity (cpm × $10^{-3}$/mL) | Infectivity (%) |
|---|---|---|
| 1000 | 588 | 100 |
| 100 | 808 | 100 |
| 10 | 918 | 100 |
| 1 | 906 | 100 |
| 0 | 1026 | 100 |

B. Effect of Carrisyn TM Extract on Jack Bean-Mannosidase Activity

Carrisyn TM extract (acemannan) was evaluated for anti-mannosidase activity by direct Jack bean mannosidase inhibition. Jack bean mannosidase activity was assayed using PNP-mannose as substrate. Swainsonine was evaluated as a positive control.

Results are summarized in Table 9.

TABLE 9

| Carrisyn TM (μg/mL) | Swainsonine (M) | Avg. A$_{400}$ | % Inhibition |
|---|---|---|---|
| 0 | — | 1.40 | 0 |
| 0.001 | — | 1.45 | 0 |
| 0.01 | — | 1.35 | 4 |
| 0.1 | — | 1.40 | 0 |
| 1 | — | 1.45 | 0 |
| 10 | — | 1.50 | 0 |
| 100 | — | 1.55 | 0 |
| — | 0.1 | 1.40 | 0 |
| — | 0.2 | 1.10 | 21 |
| — | 0.5 | 0.74 | 47 |
| — | 1.0 | 0.465 | 67 |

Microtiter Infection Assay

Carrisyn TM extract (acemannan) (7.813–1000 μg/mL) was evaluated for anti-HIV activity by microtiter infection assay on MT-2 cells; the HIV isolate HTLV-III$_{B(H9)}$ was used. Cells (cell protection) or virus (HIV inactivation) were preincubated in the presence of Carrisyn TM extract for 4 hours prior to challenge. For cell toxicity profiles, virus was omitted from the assay.

Results are summarized in Table 10.

TABLE 10

| | MW | Init. Conc. μM |
|---|---|---|
| DRUG 1: Cell Toxicity | 4000.000 | ERR |
| DRUG 2: Cell Protection | 4000.000 | ERR |
| DRUG 3: HIV Inactivation | 4000.000 | ERR |
| Drug Dilution: | 2.000 | |
| File Identifier: | Carrisyn TM Extract 4d | |

| CELL CONTROL VIRUS CONTROL | Viral Dye Uptake as % of Normals 0.387 Range | Dose of Carrisyn TM μg/ml | μM |
|---|---|---|---|
| DRUG1DIL1 | 143.762% +/− 33.248% | 1000.000 | ERR |
| DRUG1DIL2 | 147.813% +/− 8.469% | 500.000 | ERR |
| DRUG1DIL3 | 133.506% +/− 20.915% | 250.000 | ERR |
| DRUG1DIL4 | 140.315% +/− 8.945% | 125.000 | ERR |
| DRUG1DIL5 | 142.728% +/− 6.060% | 62.500 | ERR |
| DRUG1DIL6 | 142.986% +/− 8.511% | 31.250 | ERR |
| DRUG1DIL7 | 154.277% +/− 5.621% | 15.625 | ERR |
| DRUG1DIL8 | 158.845% +/− 6.467% | 7.813 | ERR |
| DRUG2DIL1 | 43.353% +/− 9.883% | 1000.000 | ERR |
| DRUG2DIL2 | 15.859% +/− 4.205% | 500.000 | ERR |
| DRUG2DIL3 | 12.066% +/− 1.760% | 250.000 | ERR |

TABLE 10-continued

| | | | |
|---|---|---|---|
| DRUG2DIL4 | 12.928% +/- 6.115% | 125.000 | ERR |
| DRUG2DIL5 | 12.411% +/- 4.988% | 62.500 | ERR |
| DRUG2DIL6 | 14.049% +/- 2.200% | 31.250 | ERR |
| DRUG2DIL7 | 13.876% +/- 5.017% | 15.625 | ERR |
| DRUG2DIL8 | 10.084% +/- 2.688% | 7.813 | ERR |
| DRUG3DIL1 | 1.896% +/- 2.169% | 1000.000 | ERR |
| DRUG3DIL2 | 11.980% +/- 3.587% | 500.000 | ERR |
| DRUG3DIL3 | 9.998% +/- 4.092% | 250.000 | ERR |
| DRUG3DIL4 | 14.997% +/- 3.879% | 125.000 | ERR |
| DRUG3DIL5 | 13.618% +/- 4.181% | 62.500 | ERR |
| DRUG3DIL6 | 12.066% +/- 4.407% | 31.250 | ERR |
| DRUG3DIL7 | 21.719% +/- 2.299% | 15.625 | ERR |
| DRUG3DIL8 | 16.548% +/- 3.862% | 7.813 | ERR |

Carrisyn TM extract (acemannan) had no toxicity against MT-2 human lymphocytes but was a growth promoter for the cells. Viral dye uptake values at all concentrations of Carrisyn TM extract were 140 to 158% of non-Carrisyn controls. Only at 1000 µg/mL was any anti-HIV activity obtained (i.e., 45% of cells were protected).

D. Effect of Carrisyn TM Extract on HIV GP-120 Molecular Weight

Carrisyn TM extract (acemannan) was evaluated for anti-mannosidase activity by its effect on HIV GP-120 molecular weight with the use of $^3$H-mannose incorporation and analysis by radioautography of SDS-PAGE gels.

Washed H9/HTLV-III$_B$ cells were incubated in the presence of Carrisyn TM (1 mg/mL) and [2-H$^3$]D-mannose (30 Ci/mmole, 50 C/mL) for 2 days. The conditioned culture fluid was then clarified of cells by low speed centrifugation and filtration (0.45 µm). The virus was harvested by centrifugation (18,000 rpm, JA-20 rotor, 4 hours, 20° C.), washed once with phosphate-buffered saline (PBS) containing 1 mM phenyl methyl-sulfonylfluoride (PMSF) and suspended in 0.2 mL of PBS-PMSF. The solubilized virus was then electrophoresed under reducing conditions in 10% acrylamide with appropriate molecular weight markers and processed for fluorography. Control virus was synthesized and processed in an identical manner except in the absence of Carrisyn TM.

Figure 6:
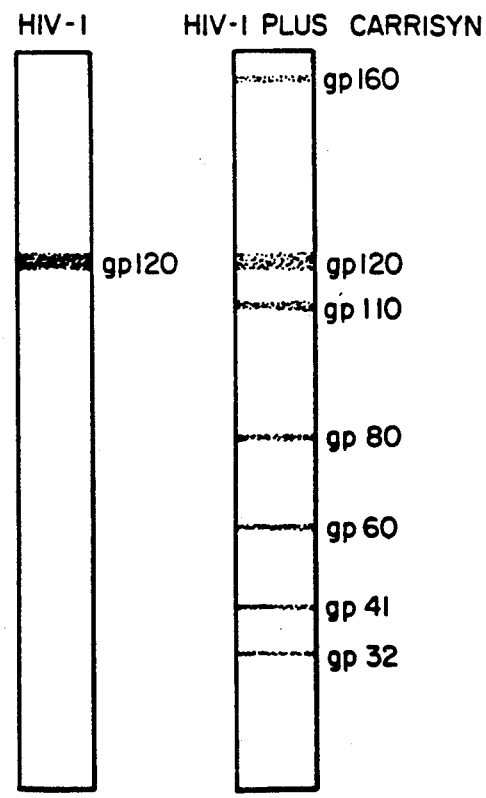
FIG. 6 is a graph depicting the effect of Carrisyn TM extract (acemannan) upon the molecular weight of the glycoprotein coat of HIV (HTLV-111$_B$).

Acemannan did not prevent glycosylation (GP-12 formation) but did result in the appearance of a number of greater and smaller molecular weight bands. Acemannan did alter glycosylation (GP-120 HIV coat glycoprotein) dramatically, as shown in FIG. 6.

Viral coat protein (GP-120) was present, but the higher and lower glycoproteins could prove to result in non-viable defective virus that compete for T$_4$ receptors in vivo. This would reduce the rate of T$_4$ infection by blocking T$_4$ receptors with non-infective viral glycoproteins.

EXAMPLE 4

The Effects of Carrisyn TM on Nonspecific Tumor Lysis

This example investigates the possibility of nonspecific tumor death induced by Carrisyn TM extract-stimulated phagocytes.

A. Procedures

Carrisyn TM Extract Polymer: Carrisyn TM extract (acemannan) was kept in a dried form. The amount needed for each experiment was weighed and microwaved in 2-minute exposures at 600 watts of power. The material was transferred to a sterile centrifuge tube (15 mL) and microwaved for one additional minute. The material was diluted in Hanks Balanced Salt Solution (HBSS) to the concentration needed. In some experiments, material was sterilized by autoclaving, with no apparent loss in activity.

Cells: Macrophages were harvested from the peritoneal cavity of BALB/c female mice obtained from Harlan/Sprague Dawley. Either thioglycolate broth (25 mg/kg) or Carrisyn TM extract (25 mg/kg) was injected IP into some groups of animals six days before harvesting. Saline-stimulated cells were also utilized as an additional control. Harvested cells were washed three times in HBSS and diluted in RPMI-1640 to a concentration of $5 \times 10^6$/cells/mL.

Target cells: Target cells were obtained from the American Type Culture Collection (C#H/HeN Fibro Sarcoma L929) and maintained in passage. Labeling was done with 150 mCi of Chromium$^{51}$ (Cr$^{51}$) mixed with 1 mL of the cell suspension containing $10^7$ cells in RPMI-1640. Cells were incubated for 1 hour, washed with RPMI-1640 three times and adjusted to a final concentration of $5 \times 10^4$ cells/mL.

Aliquots of effector cells (100 cells/µL) were placed in flat-bottomed microtiter plates. Cr$^{51}$-labeled cells were added with a minimum of three replicates per experimental point. The test plates were incubated at 37° C. in 7% CO$_2$ (previously 5% CO$_2$) for 20 hours. Supernatants (100 µL), were obtained after centrifgation of the plates at 250 ×G for 15 minutes. The amount of radioactivity was assayed on a Packard gamma counter. Controls consisted of thymocytes. The percent of cytotoxicity (%CT) was determined by:

$$\% CT = \frac{\text{cpm in test cells} - \text{cpm control cells}}{\text{total cpm of target cells}}$$

B. Results

Table 11 shows the results of the initial experiments

TABLE 11

EFFECT OF CARRISYN TM EXTRACT ON CYTOTOXICITY

| Cells | cpm ± S.D.$^a$ | % cytotoxicity |
|---|---|---|
| thioglycolate stimulated in vivo | 2,800 ± 300 | 6.6 |
| thioglycolate stimulated in vitro | 2,950 ± 260 | 7.0 |
| nonstimulated | 2,870 ± 400 | 6.8 |
| Carrisyn TM stimulated in vivo | 3,100 ± 360 | 7.4 |
| Carrisyn TM stimulated in vitro | 21,000 ± 900 | 50.0 |
| Carrisyn TM stimulated in vivo and in vitro | 20,500 ± 1100 | 48.8 |

$^a$total cpm of target cell = 42,000

Thioglycolate-stimulated macrophages incubated with Cr$^{51}$ target cells released Cr$^{51}$ at an average of 2800 cpm, whereas Carrisyn TM extract-labeled cells released radioactivity at an average of 3100 cpm. There was no statistical difference between these groups. Nonstimulated macrophages released in the range of 2800 cpm. However, macrophages stimulated with Carrisyn TM extract in vitro had a Cr$^{51}$ release of 21,000 cpm. This indicates two obvious facts. Carrisyn TM extract does not induce a long standing cytolytic effect, and its activation can occur in a relatively short time in tissue culture. The percent cytotoxicity is parallel to the cpm.

A subsequent experiment using the cytotoxic assay over time is shown in Table 12.

TABLE 12
TIME DEPENDENT EFFECT OF CARRISYN ™ EXTRACT ON CYTOTOXICITY

| Time[a] | Stimulation | cpm[b] | % Cytotoxicity |
|---|---|---|---|
| 0 | Carrisyn ™ Extract | 800 | 2.0 |
|   | Thioglycolate | 780 | 1.9 |
| 3 | Carrisyn ™ Extract | 1,400 | 3.5 |
|   | Thioglycolate | 800 | 2.0 |
| 6 | Carrisyn ™ Extract | 18,000 | 46.0 |
|   | Thioglycolate | 1,200 | 3.0 |
| 9 | Carrisyn ™ Extract | 22,600 | 57.9 |
|   | Thioglycolate | 2,200 | 5.8 |
| 12 | Carrisyn ™ Extract | 22,500 | 57.6 |
|   | Thioglycolate | 2,300 | 5.8 |
| 15 | Carrisyn ™ Extract | 23,000 | 58.9 |
|   | Thioglycolate | 21,100 | 5.8 |

[a]Time in hours after injection
[b]Cpm control cells = 39,000

The cytotoxic effect of Carrisyn ™ extract began within 6 hours after stimulation and increased to its maximum by 9 hours. The mechanism of this activation has not been investigated.

The data shown in this example indicate that Carrisyn ™ extract may have an important role in the nonspecific therapy of cancer.

Screening of Carrisyn ™ Extract for Potential Efficacy Against Equine Sarcoid. Three sarcoids on two horses were treated both IV and intralesionally with Carrisyn ™ extract. The goals of this trial were to determine if Carrisyn ™ extract might be effective treatment against equine sarcoid and also to observe the patients for adverse reactions. On horse 1, one sarcoid completely resolved while a second sarcoid did not decrease in size. A third nodular sarcoid developed during treatment. On horse 2, a single sarcoid completely resolved. These results suggest that Carrisyn ™ extract may be useful in the treatment of equine sarcoid.

Two horses with three suspicious lesions were purchased at a sale. The lesions were photographed, measured and confirmed by histopath as sarcoids.

Horse 1: Day 1. Each of the two lesions on the right rear leg was treated by direct injection (20 ga. needle), with 50 mg Carrisyn ™ extract diluted in 10 ml saline (lesion 1) and 5 ml saline (lesion 2). Twenty-five mg Carrisyn ™ extract diluted in 7.5 ml saline was also given IV.

Day 7. Lesion 1 (upper lesion) was treated (18 ga. needle) with 50 mg Carrisyn ™ extract diluted in 10 ml saline. Lesion 2 was treated with 25 mg diluted in 7.5 ml saline. Fifty mg in 10 ml saline was given IV.

Day 14. Lesion was treated with 50 mg in 10 ml saline, whereas lesion 2 was treated with 25 mg in 5 ml saline. Seventy-five mg in 25 ml saline was given IV.

Day 21. Lesion 1 was treated with 50 mg in 10 ml saline, and lesion 2 was treated with 25 mg in 10 ml saline. One hundred mg in 25 ml saline was injected IV.

Day 29. Lesion 1 was treated as on day 21, but because of local swelling lesion 2 was not treated directly. One hundred mg in 25 ml saline was given IV.

Day 42. Lesion 1 was not treated directly. Lesion 2 was treated with 25 mg in 10 ml saline. One hundred mg in 50 ml saline was given IV.

Day 57. Horse 1 was euthanized, and tissue samples were taken at the site of lesion 1, from lesion 2, inguinal lymph nodes and a nodular lesion on his left shoulder that had developed during the course of treatment.

Horse 2: Day 1. The lesion on the lower left thorax was treated with 50 mg Carrisyn ™ extract diluted in 30 ml saline. One half was injected subcutaneously (S/Q) and the other half intralesionally.

On days 6, 16, 24, 30, 49, 56, 63, 70 and 77 horse 2 was given 100 mg Carrisyn ™ extract IV diluted in 60–120 ml saline, the amount of diluent varying as required to make a clear solution.

On days 105, 113 and 120 the lesion was treated with 25 mg Carrisyn ™ extract diluted in 5 ml saline, intralesionally and S/Q at the base of the lesion. An additional 75 mg was given IV.

Results-Horse 1: Day 1. Lesion 1 measured 2.5 cm (length horizontally) ×2.5 cm (height vertically) ×1 cm (thickness). The resolution of this lesion can be followed below:

| Horse 1 - Lesion 1 | |
|---|---|
| Day | Measurements |
| 1 | 2.5 cm × 2.5 cm × 1 cm |
| 7 | 2.5 cm × 1.75 cm × 1 cm |
| 14 | 2.0 cm × 1 cm × 1 cm |
| 21 | 2.0 cm × 1 cm × now flush with skin level |
| 29 | 2.0 cm × 1 cm × flat and dry |
| 42 | all but healed |
| 54 | completely healed |

Lesion 2 measured 2 cm ×2 cm×1 cm on Day 1 and never changed significantly. Results on lesion 2 are indicated below:

| Horse 1 - Lesion 2 | |
|---|---|
| Day | Measurements |
| 1 | 2 cm × 2 cm × 1 cm |
| 7 | 2 cm × 2 cm × 1 cm |
| 14 | 2 cm × 2 cm × 1 cm |
| 21 | 2 cm × 2 cm × 1 cm |
| 29 | 2 cm × 2 cm × 1 cm - entire hock still swollen and painful |
| 42 | size slightly less - still swollen, not as painful |
| 54 | same size - hock swelling down 65% |

Results-Horse 2: Day 1. The lesion measured 5 cm×3.5 cm×2.5 cm with a pedunculated base of 2.5 cm. The changes until complete resolution are shown below:

| Horse 2 - Lesion 1 | |
|---|---|
| Day | Measurements |
| 1 | 5 cm × 3.5 cm × 2.5 cm |
| 6 | no change |
| 16 | no change - more granulomatous |
| 24 | 5 cm × 3 cm × 2.5 cm |
| 30 | less granulomatous |
| 49 | 4 cm × 3 cm × 2 cm |
| 56 | 4 cm × 3 cm × 2 cm |
| 63 | 3.8 cm × 3 cm × 2 cm |
| 70 | 3.7 cm × 2.6 cm × 1.8 cm |
| 77 | 2.7 cm × 2 cm × 1.3 cm |
| 105 | 2.5 cm × 2 cm × 1.3 cm |
| 113 | 3.5 cm × 2.25 cm × 1.5 cm |
| 120 | 2.5 cm × 2.4 cm × 0.6 cm |
| 177 | Lesion completely resolved |

After IV administration there was no change in heart rate and no sweating, muscle fasciculation or obvious signs of distress. A slight increase in depth of respiration was noted in horse 1 only. Locally, horse 1 showed an inflammatory cellulitis of a mild nature at lesion 1 and of an acute painful type at lesion 2, enough so that the lesion was not injected as scheduled on day 29. Lesion 2 was more fibrous and much more difficult to inject into, so that there was more leakage S/Q. This could account for the lack of effect on lesion 2. Horse 2 did not show cellulitis.

The fact that a nodular sarcoid developed during the course of treatment leads one to suspect that the main effect of Carrisyn TM extract is a local tissue reaction rather than a systemic one, although IV administration may sensitize the sarcoid to intralesional treatment.

The exact date at which the lesion on horse 2 resolved is unknown because the investigator was on a 60-day sick leave between day 113 and day 177. Judging from the lack of significant reduction in tumor size by day 56, it would appear that weekly IV administration alone had little effect on the sarcoid on horse 2.

EXAMPLE 5

Enhancement of Allo-Responsiveness of Human Lymphocytes by Carrisyn TM

This example was designed to test the capacity of Carrisyn TM extract (acemannan) to enhance immune response to alloantigen and to test whether the potential enhancement is a monocyte-driven phenomenon. Carrisyn TM extract did not enhance lymphocyte response to syngeneic antigens in the mixed lymphocyte culture (MLC), but it importantly increased alloantigenic response in a dose-response fashion ($2.6 \times 10^{-7}$–$2.6 \times 10^{-9}$M). This effect of Carrisyn TM extract was shown to be a specific response and to concur with concentrations of in vitro Carrisyn TM extract achievable in vivo. A separate series of mixing experiments demonstrated that Carrisyn TM extract incubation with monocytes permitted monocyte-driven signals to enhance T cell response to lectin. It is concluded that the acemannan of Carrisyn TM extract is the active ingredient of the Aloe vera plant and is an important immunoenhancer in that it increased lymphocyte response to alloantigen. It is suggested that the mechanism involves enhancement of monocyte release of Il-I under the aegis of alloantigen. This mechanism may explain in part the capacity of Carrisyn TM extract to abrogate viral infections in experimental animals and man.

This example was designed to directly assess the impact of Carrisyn TM extract as an immune enhancer in the model of monocyte-T-lymphocyte, cell-cell interaction response to alloantigen presented in the mixed lymphocyte culture. This model tests the capacity of Carrisyn TM to stimulate additional monocyte-macrophage functions in an immunologically relevant model.

A. MATERIALS AND METHODS

1. Cell Preparation. Mononuclear leukocytes were obtained from the peripheral blood of normal, informed and consenting human volunteers under the aegis of a study approved by the Institutional Review Board of the University of Texas Southwestern Medical Center at Dallas. Peripheral blood was diluted 1:3 in Hanks' balanced salt solution (HBSS) and layered on top of a ficol-hypaque gradient according to the method described in *Journal of Clinical Investigation*, 59: 338-344 (1977). Cells from subjects known to be Major Histo. Compatibility disparate were obtained on each study day to ensure a positive mixed lymphocyte reaction. For specific experiments, more carefully characterized pedigrees of cells which inhabit the mononuclear leukocyte pool were isolated. T-lymphocytes were isolated by the standard nylon wool separation technique as described in *Journal of Clinical Investigation*, 59: 338-344 (1977), the disclosure of which is hereby specifically incorporated herein by reference. The nylon effluent cells contained about 90% pure T cells. B lymphocytes and monocyte-macrophages preferentially adhere to the column. The adherent population was removed by forcibly pushing media through the column with a plunger. To enrich for monocytes (macrophages), the glass adherence procedure as described in *Journal of Clinical Investigation*, 59: 338-344 (1977) was utilized to produce a population greater than 95% pure.

2. Carrisyn TM Extract. Carrisyn TM extract was tested in these studies by preparing a 0.5% (w/v) solution in RPMI-1640 medium and further diluting to the following working concentrations: $2.6 \times 10^{-7}$M, $2.6 \times 10^{-8}$M and $2.6 \times 10^{-9}$M.

3. Mixed Lymphocyte Cultures (MLC). Unidirectional MLC were set-up in microtiter, flat-bottom tissue culture plates (Costar Co., Cambridge, MA). Mononuclear cells, isolated by the ficoll-hypaque density gradient technique discussed above, served as stimulator cells after exposure to 2000 rads for 30 minutes in a cesium source (Gammacell, Atomic Energy of Canada, Ontario, Canada). Responder cells, similarly isolated, and stimulators were adjusted to $1.3 \times 10^6$ cells/mL. To each well the following were added: 25 μL of Carrisyn TM or media (control), 25 μL of RPMI-1640 supplemented with 10% fetal bovine serum and 75 μL of each cell population. Cells were incubated at 37° C. in 5% $CO_2$: 95% air for 6 days. Cultures were pulsed with 25 μL of $^3$H-thymidine (1 μCi/well) for 4 hours, after which the cells were harvested and counted. To test the specificity of Carrisyn TM extract on the afferent recognition and response to MHC, additional unidirectional MLC were set up with the agent added just 20 minutes before the cells were pulsed with $^3$H-thymidine.

4. Monocyte-T Cell Interaction. Lewis female rat spleens were teased through a sterile steel mesh into RPMI-1640 medium. Mononuclear leukocytes were collected from the interface of a ficoll-hypaque density gradient as described above. Monocytes, obtained by enrichment on glass petri dishes and adjusted to a final concentration of $10^6$/mL, were incubated with varying doses of Carrisyn TM extract or medium (control) in a total volume of 2 mL and incubated for 24 hours at 37° C. The monocytes were harvested, extensively washed with fresh medium and co-cultured with syngeneic T lymphocytes, at a ratio of 10 T-cells: 1 monocyte, with the plant lectin phytohemagglutinin (Difco, Detroit, MI) [(1:100)] for 48 hours at 37° C. Cells were harvested over a MASH II (Whittaker, M.A. Bioproducts, Walkersville, MD), placed in fluor and counted in a scintillation counter (Beckman Laboratories, Chicago, IL). A control experiment was performed by incubating T lymphocytes with Carrisyn TM extract, followed by wash and co-culture with freshly prepared T lymphocytes, again at 10:1 along with PHA-P.

B. Results

1. Alloantigenic Response. Carrisyn TM extract had no statistically important effects on the response of T-cells to autoantigens. When the agent was added at the beginning of mixed lymphocyte cultures (MLC), cells receiving syngeneic stimulation incorporated tritiated thymidine equally in the presence or absence of test reagent at the doses described (see FIG. 7 for doses). In the absence of oral Carrisyn TM extract these MLC incorporated $2616\pm1099$ cpm of tritiated thymidine at the end of a 4 hour pulse. Although there was a trend upward with respect to the dose of agent added ($3281\pm1355$ at $2.6\times10^{-9}$M, $3742\pm1670$ at $2.6\times10^{-8}$M, and $3828\pm1978$ at $2.6\times10^{-7}$M), none of these rates of isotopic incorporation into DNA was statistically significantly different.

Figure 7:
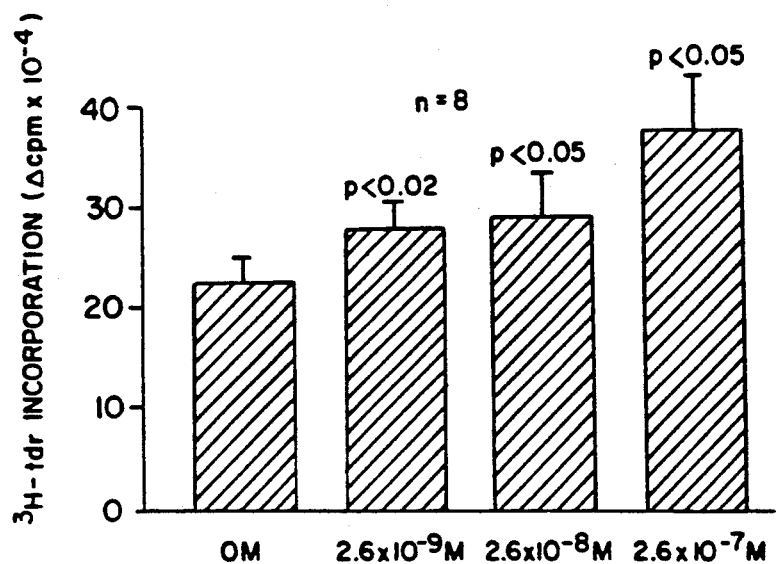
FIG. 7 is a graph showing the effect of Carrisyn TM extract on the alloresponse in the Mixed Lymphocyte Response (MLC) in which tested cells receive syngeneic stimulation. The graph shows a comparison between various does of acemannan and the amount of synthesis, estimated by the incorporation of $^3$HTdR, tritiated thymidine. Drug was added at the beginning of the MLC. The mean ±SEM of eight experiments is shown.
Figure 8:
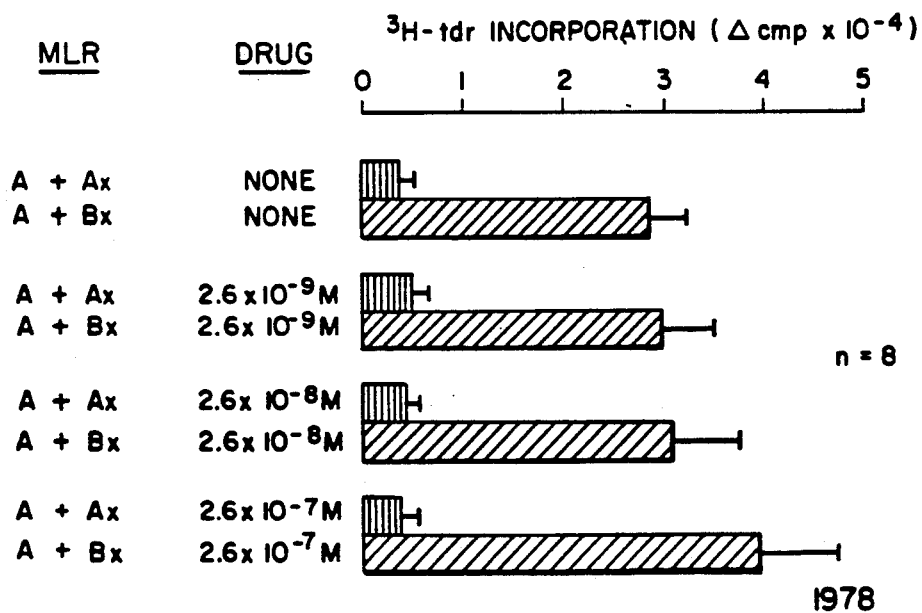
FIG. 8 is a graph showing the effect of Carrisyn TM extract on the alloresponse in the MLC; the alloresponse is plotted as a function of syngeneic response. The effect is represented by (A) for syngeneic, (B) for allogeneic, and (X) for irradiated populations. Results are plotted as —counts per minute (CPM) of alloresponse as a function of syngeneic response. The mean ±SEM of eight experiments is shown.

In contrast to the absence of effect of Carrisyn TM extract on autoresponse in the MLC was the agent's effect on alloresponse in the same immunologic assay (FIG. 7). Firstly, Carrisyn TM extract did not interfere with the capacity of lymphocytes to recognize and respond to class 2 alloantigenic differences in the mixed lymphocyte culture; this is apparent when the syngeneic cultures are compared to the allogenic response in the presence of the lowest concentration of drug. Secondly, there was a dose response-related enhancement of alloresponse by Carrisyn TM extract such that the culture treated with the highest dose, $2.6\times10^{-7}$M, reflects a nearly 60% increase over the culture without addition of drug. The effect of Carrisyn TM extract on allogeneic stimuli is most clearly seen in FIG. 8, in which the results are plotted as $\Delta$cpm of alloresponse as a function of syngeneic response. The dose response relationship is most convincingly demonstrated as the enhanced allogeneic response is shown to be significant for each dose of Carrisyn TM extract tested with respect to the no drug condition.

Figure 9:
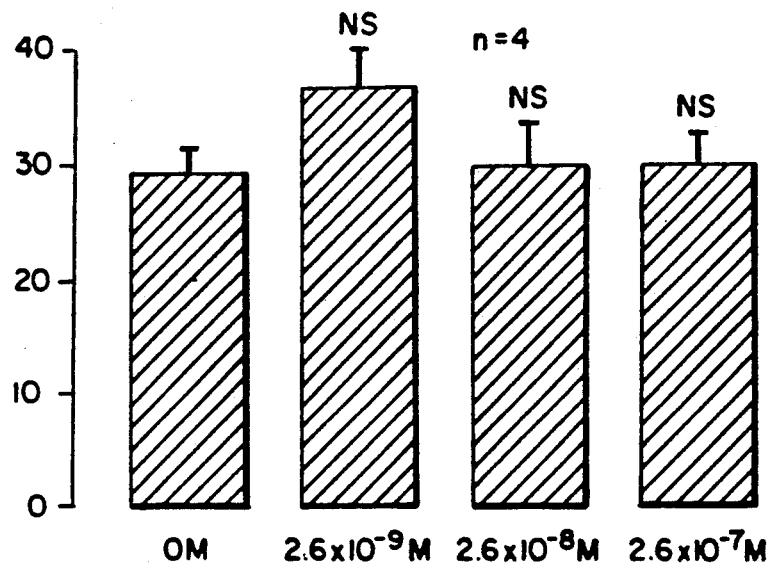
FIG. 9 is a graph showing the effect of Carrisyn TM extract on the nonspecific MLC response of a tritiated thymidine incorporation. Various doses of the drug were added to MLC 20 minutes before addition of tritiated thymidine. The mean ±SEM of four experiments is shown.

To ascertain whether Carrisyn TM extract exerts a specific effect on lymphocyte alloresponse or a nonspecific effect on tritiated thymidine incorporation, the reagent was added at the conclusion of a 7 day mixed lymphocyte culture MLC, 20 minutes before addition of the tracer to the culture. As can be seen in FIG. 9, there was no effect of Carrisyn TM extract when added in this manner as a pulse at the conclusion of the MLC. These data support the specificity of the Carrisyn TM extract effect on enhancement of lymphoid response in the MLC.

Figure 10:
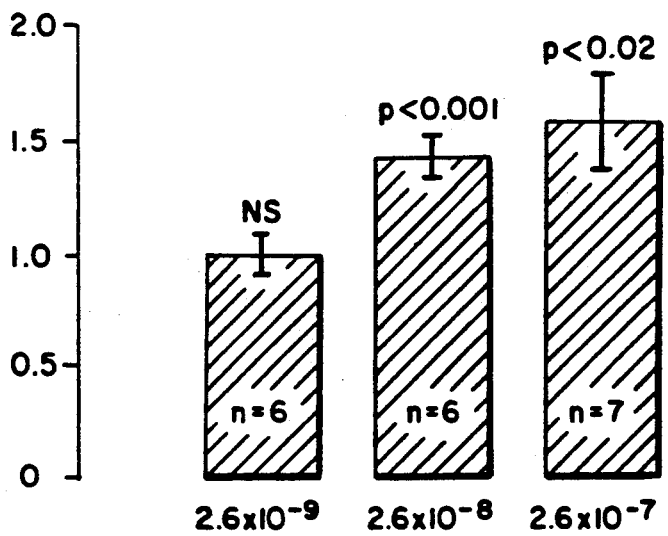
FIG. 10 is a graph showing the effect of Carrisyn TM extract on Monocyte-T-Cell Cooperation. Comparison between various doses of the drug on the ratio of enhancement, expressed as CPM in experimental wells divided by CPM in the control well. The mean ±SEM of five experiments is shown.

2. Carrisyn TM and Monocyte-T Cell Cooperation. To test the hypothesis that Carrisyn TM extract directly stimulates the monocyte responding to alloantigen to provide signal(s) to enhance lymphoid response to antigen and/or mitogen, purified populations of monocytes were incubated for 24 hours with various doses of drug. At the conclusion of the incubation the cells were washed extensively and then co-cultured with T lymphocytes at a ratio of 10:1, to simulate the natural ratio found in peripheral blood. Co-cultured cells were stimulated with phytohemagglutinin. As can be seen in FIG. 10, the co-cultures with monocytes that were previously incubated with Carrisyn TM extract had a significantly increased mitogenic response in a dose related fashion.

C. Discussion

This example has explored the capacity of acemannan to function as an immunostimulating drug with important clinical consequence.

Carrisyn TM extract is believed to be capable of delimiting infections to DNA and retro-viruses that cause significant disease in animals and in man. For example, in an animal model, Carrisyn TM extract reduced feline viral rhinotracheitis. There is additional evidence that Carrisyn TM extract in vitro and in vivo may be effective against *Herpes simplex* II virus, the measles virus and perhaps the HIV. There is evidence that the immunologic mechanism may involve enhancement of the monocyte, both as a phagocytic cell and as a cell that contributes to afferent recognition of antigen. Studies have shown direct enhancement of phagocytic properties of the monocyte on the one hand and an increase in the absolute numbers of that important cell on the other. There is mounting evidence to support the concept that Carrisyn TM extract enhances the elaboration by the activated monocyte of the signal substance interleukin-I.

The studies described in this example were directed specifically at exploring the mechanism by which Carrisyn TM extract may be an immuno-enhancing reagent. The MLC is an in vivo model of the manner in which immunocompetent cells participate in response to antigen of the variety that is necessary for recognition and response to virus. In this reaction, there are important monocyte-T-lymphocyte interactions that generate a response to alloantigen. It was this model that was chosen for testing the capacity of the drug to function as an immunoactivator.

Carrisyn TM extract is therefore an important enhancer of the alloantigenic response in the MLC. There is a dose response relationship, with enhancement at the highest dose tested of about 60% above basal. This represents not only a statistically significant but also a biologically relevant increase in response to alloantigen and may serve as one means by which the drug can aid the response of the organism to viral assault. This effect of Carrisyn TM extract was shown to be specific for the allogeneic stimulus, provided the drug did not enhance either basal response to self (syngeneic MLC) or nonspecific incorporation of a tracer DNA precursor, tritiated thymidine, when drug was added at the conclusion of the MLC.

A second series of experiments tested the hypothesis that monocyte-T-lymphocyte interactions may be at least in part responsible for the heightened alloresponse in the mixed lymphocyte culture. In this series of experiments Carrisyn TM extract was incubated along with monocytes, after which the treated, extensively washed monocytes were mixed with freshly prepared, syngeneic, T-lymphocytes that had not been exposed to and would not be exposed to drug. These experiments demonstrated the enhancement of T-lymphocyte response to the polyclonal mitogen phytohemagglutinin at a magnitude equal to the response that had been seen previously in the MLC, approximately 55% above baseline with a dose response relationship.

The lowest dose that was tested in the study that was effective in the MLC had no effect in the monocyte experiment. It is not surprising that the threshold dose may be different for the two models tested, polyclonal response to mitogen and alloantigenic response in the MLC. It can also be observed that the monocyte experiment is a more stringent test of the effect of Carrisyn TM extract, because it presents a treated cell type, the monocyte, to T cells that then see an immune stimulus in the absence of drug. While the alloantigenic response may be due solely or in great measure to Carrisyn TM extract-enhanced monocyte production of interleukin-I (Il-1), the lesser polyclonal mitogen-enhanced response may be a consequence of an assay of immune stimulations, each with a different threshold response to Carrisyn TM extract.

The dose of Carrisyn TM extract used in these experiments is clinically relevant. The dose range selected was chosen precisely to bracket that concentration of Carrisyn TM extract that could be expected to be achieved in plasma if the drug distributes in extracellular water and is absorbed at the rate of a third of the orally administered dose, figures that were based on previous pharmacological studies in dogs. The actual concentrations achievable in man also have been shown to be in this range, further supporting the potential relevance of these studies for clinical practice.

Carrisyn TM extract (acemannan) was shown by these experiments to cause monocytes to release monocyte-driven signals to enhance T4 cell response to lectin. While acemannan did not enhance lymphocyte response to syngeneic antigens in mixed lymphocyte culture (MLC), it did increase MLC alloantigenic response in a dose related manner. This response was shown to be an acemannan specific response at acemannan concentrations achievable in vivo.

This experimental documentation demonstrates that acemannan is an immunoenhancer and biological response modifier in that it increases lymphocyte response to alloantigen. A proposed mechanism of action involves stimulation of monocytes to release Il-1; in the presence of acemannan Il-1 has been shown to be released from monocyte cultures. The pharmacological action of acemannan stimulation of monocytes may explain acemannan activity against viral infection in animals and man.

EXAMPLE 6

Preparation of 125 mg CARRISYN TM Capsules

|   |   | (A) mg/dose | (B) Quantity of Raw Material for Final Blend to Yield Product (A) |
|---|---|---|---|
| (1) | Acemannan (Carrisyn TM extract as a powder, U.S. Pat. No. 4,735,935) | 125 | 1250 g |
| (2) | Lactose USP | 249.5 | 2495 g |
| (3) | Aerosil TM 380 (colloidal silicone dioxide NF) | 3.6 | 36 g |
| (4) | Calcium Stearate NF | 1.9 | 19 g |
|   |   | 380 mg | 3800 g |

A. Manufacture of the Capsule Mixture

The preparation area is inspected for any foreign contaminants. The operators should maintain sterile conditions and should preferably wear hair nets, rubber gloves and dust masks when handling the open product. A standard Hobart Mixer (Hobart Corporation, Troy, Ohio, Model No. D300) with 30 quart capacity and a "B" type beater blade is set at mixing speed one. After the raw materials are checked and weighed, the mixer is initially charged as follows: The Aerosil TM 380 NF (Degussa Corp., Tetterboro, N.J.), ingredient (3), is screened through a #12 stainless steel hand screen into a drum of lactose, ingredient (2). The Aerosil 380 silicon dioxide is mixed with a scoop in the drum to disperse the Aerosil into the Lactose USP (McKesson, Burkley, Calif.). An operator adds one-half of the Lactose/Aerosil mix into the Hobart TM Mixer. Next, an operator screens the Carrisyn TM extract, ingredient (1), through a #12 stainless steel screen, and adds it to the Hobart Mixer. Then, an operator adds to the screened material the remaining half of the Lactose/Aerosil mixture. The screened material is then mixed for 10 minutes. Next, an operator screens the Calcium Stearate NF (Mallinckrodt, St. Louis, Mo.), ingredient (4) through a #12 stainless steel hand screen, and adds it to the Hobart Mixer. After mixing for an additional 3 minutes, the resulting mixture is a blended powder. It is then discharged into a clean, double poly-lined container. An operator then records the weight and retains the mixture for the final blend. Carrisyn TM powder is then added, ingredient (1). Then, the final blend is transferred to clean, double poly-lined containers. The weight of each container of final blend is recorded. The material is transferred to the encapsulation area.

B. Capsule Filling

The encapsulation area is checked for any foreign contaminants as before. The operators should maintain sterile conditions and should preferably wear hair nets, rubber gloves and dust mask when handling the open product. A Model 8 Capsule TM capsule filling machine is set at 0.6 row set. The auger of the machine is installed in the powder feed hopper. The rotary table speed is adjusted to achieve the indicated net capsule fill weight. The powder hopper of the machine is maintained three-quarters full of powder (final blend). The vacuum and air pressure are adjusted to the #0 PoSilok Capsule Size (opaque white QX) (Elanco, Indianapolis, Ind.). The net fill weights of the capsules are checked. The weights of the capsules are recorded along with the capsule shell usage.

C. Capsule Polishing (Finishing)

The preparation area is checked for contaminants. The operators should maintain sterile conditions and should preferably wear hair nets, rubber gloves and dust masks when handling the open product. The 364' stainless steel coating pan of a capsule polishing machine (Sharpels-Stokes Div. of Pennwalt Corp., Warminster, Pa.) is loaded with sufficient amount of sodium chloride U.S.P. Granular (Morton Salt Div., Richardson, Tex.). An operator records the weight of sodium chloride added. While rotating the pan, an operator charges unpolished capsules into the pan and allows the capsules to rotate in the salt bed. An operator stirs the polished capsules as needed. Polished capsules are then removed from the pan with a hand screen and passed over a #10 stainless steel screen to remove excess salt or capsule fragments. Next, the capsules are visually inspected, and any empty capsule shells, caps or bodies are removed. The capsules are then transferred to a paper-lined stainless steel tray and spread out into a single layer. The capsules are visually inspected for dented ends, splits or low fills. An operator drums up the inspected capsules in a double poly-lined container. The capsules are held for sampling and release to packaging. The final weight, number of containers and net weight are recorded.

EXAMPLE 7

Preparation of 50 mg Carrisyn TM Tablets

A. Preparation of the Commercial Mixture

The equipment of Example 6 is cleaned and sanitized with 50% isopropyl alcohol (Delta Solvents and Chemicals Co., Dallas, Tex. 75285) and then dried. The following materials are weighed separately, added to a 2-ft$^3$ PK blender ("Twin Shell Dry Blender", Patterson Kelly, Div. of Harsco Corp., East Stroudsburg, Pa., Ser. No. 710352) and mixed for 30 minutes. The end product will be tablets of the composition indicated below (A).

| Ingredient | (A) mg/dose | (B) Quantity of Raw Material for Final Blend to Yield Product (A) |
|---|---|---|
| (1) Acemannan (as Carrisyn TM powder) prepared according to U.S. Pat. No. 4,735,935 | 50 | 500 g |
| (2) Stearic Acid (NF grade) (Union Camp Co., Wayne, NJ) | 6 | 60 g |
| (3) Syloid TM 244 (Davison Chemical Co. Baltimore, MD) | 0.6 | 6 g |
| (4) Solka TM Floc (Granular) (James River Corp., Atlanta, GA) | 130.9 | 1309 g |
| (5) Corn Starch (Best Foods Co. Inglewood Clif, NJ) | 100 | 1000 g |
|  | 287.5 | 2875 |

The PK blender is turned on by an operator, and mixing continues for 30 minutes.

B. Tablet Preparation

The blended powder is transferred into a 10-gallon stainless steel container. A stainless steel scoop is used to fill the hopper of the tablet press of a standard tablet machine (Stokes "Model F" Single Punch Tablet Press TM, Sharpels-Stokes Div. of Pennwalt Corp., Warminster, Pa.) with blended powder. The machine is turned by hand through a few cycles to adjust to the designated tablet weight according to the batch record (1-4 tons). An operator switches on the motor and starts the tablet press. The necessary adjustments are made until the tablets are uniform with regard to proper weight and hardness. An operator weighs ten tablets collectively each ten minutes and records the weight. The hardness should be in the range of 4 to 6 on a Stokes hardness tester.

EXAMPLE 8

Preparation of Injectable Carrisyn TM Solution

A. Manufacture of the Solution

Carrisyn TM extract (acemannan) is prepared according to U.S. Pat. No. 4,735,935. Twelve samples of Carrisyn TM extract in wet form, weighing approximately 100 grams each, are placed in sterile Mason jars and lyophilized (two units: one of Unitop TM 600 SL, the other Freeze Mobile TM 21, both Vertis Corp., Gardiner, N.Y.). The resultant Carrisyn TM raw powder is weighed, and the weights are recorded. Approximately 87 grams of the finished lyophilized raw product is obtained. A Krup TM "Fast Touch" Coffee Mill, Model 203 (Robert Krup N.A., Closter, N.J.) is sanitized with 50% isopropyl alcohol (Delta, Dallas) and allowed to dry. The operators should maintain sterile conditions and should preferably wear gloves and laboratory coats. All work is carried out in a Biological Safety Cabinet that has been cleaned with Bac-Down TM disinfectant (containing both (1) n-alkyl-(60% $C_{14}$, 30% $C_{16}$, 5%-$C_{12}$, 5%-$C_{18}$)-dimethyl benzyl-ammonium chloride and (2) n-alkyl (68% $C_{12}$, 32% $C_{14}$) dimethyl ethyl benzyl ammonium chloride, sold through Curtin Matherson Scientific, Houston, Tex.) and lined with clean under-padding. Sterile Corning jars are preweighed before adding the milled Carrisyn TM. Approximately 5 grams of the lyophilized Carrisyn TM raw powder is milled, after cutting the large pieces into smaller pieces with sterile B-P blades The Carrisyn TM powder is milled to 100 mesh with a pulsating action to reduce it to a fine powder form. The Carrisyn TM fine powder is placed into sterile Corning jars and reweighed. To form a solution, 5 grams of fine-milled Carrisyn TM powder is transferred into 1 liter of sterile 0.9% normal saline (Travenol Co., Deerfield, Ill.), which contains 0.5% chlorobutanol (Kodak Co., Rochester, N.Y.), and placed in a large sterile, pyrogen-free bottle (1.5L). The Carrisyn TM saline solution is placed on an Orbitron TM Rotator (Boekel Co., S.N. HRO 8155-27, Philadelphia, Pa.) in a refrigerator overnight to allow the Carrisyn TM -containing solution to solubilize. The Carrisyn TM saline solution is then taken off the rotator and set upright in the refrigerator for 1 hour to allow the particles to settle.

B. Bottling

Sterile 60 mL commercial IV bottles for subcutaneous IV injection (Wheaton Co., Millville, N.J.) with sterile rubber stoppers are rinsed with deionized water, capped with aluminum foil and autoclaved for 15 minutes at 15 lbs. pressure and 121° C. The sterile bottles are placed in a 170° C. drying oven overnight to inactivate any residual pyrogen. The caps for the bottles are also rinsed and autoclaved along with the bottles. The Carrisyn TM saline solution is dispensed in 10 mL aliquots into the 60 mL sterile, pyrogen-free bottles. This process is done in a Biological Safety Cabinet (Class 2, Type A, Germ Free Co., Model 820, Miami, Fla.). The desired concentration is approximately 50 mg Carrisyn TM /50 mL or 1 mg/mL saline. The bottles are capped with the sterile rubber stoppers. The Carrisyn TM saline solution in the capped bottles is lyophilized. After the samples are dry, the bottles is capped with metal bands and labeled properly. The samples are then held until released from the quality control and assurance personnel according to good manufacturing practices. When ready for use, 25 mL of normal saline solution U.S.P. is added to the contents of the 60 mL vials. The mixture should be shaken well before administration to the patient.

EXAMPLE 9

Preparation of Carrisyn TM Gel and Cream

All equipment for this example is cleaned and sanitized with 50% isopropyl alcohol (Delta Solvents and Chemicals, Dallas, Tex. 75285) and then rinsed with deionized water. Ten gallons (37.9 L) of deionized water are added to the collection tank of the 1000 gallon mixer of Example 1 of U.S. Pat. 4,735,935 (Process Equipment Corp. of Belding, Mich., Model No. 1000 Gallon OVC, Ser. No. 40866-2). The following chemicals are dissolved with agitation in the deionized water:

|   | Ingredient | Amount |
|---|---|---|
| (1) | Methylparaben (Sutton Labs, Chatham, NJ) | 681.0 g |
| (2) | Potassium Sorbate (Miles Laboratories, Elkhart, IN) | 379.0 g |
| (3) | Imidazolidinyl Urea (Germall TM 115) (Sutton Labs., Chatham, NJ 07928) | 189.0 g |
| (4) | Sodium Metabisulfite (General Chemical, Parsippaney, NJ) | 76.0 g |

With continued agitation, the raw Aloe vera gel (preferably Carrisyn TM wet extract) is collected from the grinder into the collection tank to a total volume of 100 gallons (379L). The tank is removed to the compounding area. A homogenizer (Crepaco Food Equipment and Refrigeration Inc., Chicago, IL, Model 3DD13, Ser. No. 04-03) is set at 1500 psig pressure and is connected to the collection tank. The homogenizer is started, and the product is discharged into the open stainless steel basket mounted in the 1000 gallon stainless steel tank When the product covers the mixer blades, agitation is started. Agitation is continued at slow speed all day. All 100 gallon portions manufactured are then added to the 1000 gallon tank. The wet product is allowed to set overnight. A Leslie's TM Diatomaceous Earth Filter (Model DE-48) is used. The diatomaceous earth filtered material is flushed for 20 minutes with a 5% by weight solution of 65% calcium hypochlorite (York Chemical, Dallas, Tex.) and then flushed with deionized water. One kilogram of diatomaceous earth (Eagle Pitcher Co., Tulsa, Okla.) is added to 11 gallons of deionized water and mixed until suspended. The final mixture is circulated through the Leslie's TM diatomaceous earth filter until the water is clear. The excess water is then flushed from the diatomaceous earth filter with product. The product is circulated through the filter until the product is clear of pulp. Then the final product is mixed for 30 minutes and is ready for packaging.

EXAMPLE 10

Preparation of Carrisyn TM Douche or Enema

The tanks with mixers, the homogenizers and other equipment of Example 9 are sanitized with 50% isopropyl alcohol (Delta Solvents and Chemicals, Dallas, Tex. 75285) and rinsed with hot deionized water. The diatomaceous earth filter is sanitized by filtering a 5% calcium hypochlorite solution (York Chemical, Dallas, Tex.) through the entire system for 20 minutes.

Ten gallons (37.9L) of deionized water is added to the collection tank of the 1000 gallon mixer of Example 9. While stirring the following chemicals are dissolved in the deionized water:

|   | Ingredient | Amount |
|---|---|---|
| (1) | Sodium Benzoate U.S.P. (Southland, Dallas, TX) | 756 g |
| (2) | Glycine (Emuetec, Dallas, TX) | 3.0 Kg |
| (3) | Citric Acid U.S.P. (Miles, Elkhart, IN) | 416 g |
| (4) | Potassium Sorbate U.S.P. (Miles, Elkhart, IN) | 569 g |
| (5) | Vitamin E (1000 Units) | 1 capsule |

|   | Ingredient | Amount |
|---|---|---|
|   | (Hoffman-La Roche Inc., Dallas, TX) |   |

Agitation is continued and Carrisyn TM wet extract is added to the grinder into the collection tank to make a total volume of 100 gallons (379L). The tank is removed to the compounding area as in Example 9. The sanitized Crepaco homogenizer of Example 9 is set at 1500 psig pressure and is connected to the collection tank of the 1000 gallon mixer. The homogenizer is started and discharges the product to the open stainless steel basket mounted in the 1000 gallon jacketed stainless steel tank. Starting and stopping times during the homogenization process are recorded. Agitation is started when the product covers the mixer blades. Approximately 151.2 g of sodium metabisulfite (General Chemical Co., Parsippaney, N.J.) is added to the mix, and agitation is continued for 20 minutes. All 100 gallon portions manufactured are added to the 1,000 gallon tank. The product is allowed to set overnight. The diatomaceous earth filter is then flushed out with hot deionized water. Then 1 kilogram of diatomaceous earth (Eagle Pitcher Co., Tulsa, Okla.) is added to 10 gallons of deionized water and mixed until suspended. The mixture is circulated through the diatomaceous earth filter until the water is clear. The excess water is flushed from the product through the diatomaceous earth filter until the product is clear of pulp. The product is allowed to mix for 30 minutes. The product is held until released by quality control and assurance personnel, and once the product is approved, the bottles may be filled.

EXAMPLE 11

Preparation of Carrisyn TM Suppositories

A. Sanitization of Equipment

First all the equipment is sanitized with 50% isopropyl alcohol (Delta, Dallas, Texas) and rinsed with hot deionized water. Approximately 927 Kg of Eutra TM paraffin mineral oil and petrolatum (Colleen Ryan Corp., Dallas, Tex.) is added to the dry kettle and agitated. Then, approximately 30 Kg of paraffin (Carbowax TM, melting point −37° C., Union Carbide, Danbury, Conn.) is added.

B. Preparation of Suppository Composition

The Eutra TM material and Carbowax TM paraffin are first heated to 50° C. ±5° C. with agitation, then the heat is turned off and agitation is continued. 1.0 Kg of propylparaben (Sutton Labs, Chatham, N.J.) and 2.0 Kg of butylparaben (Delta, Dallas, Tex.) are added. The solution is then mixed for 15 to 20 minutes until the preservatives are dissolved. 30.6 Kg of lecithin and a protein binder (Alcolee TM Z-3, American Lecithin Co., Atlanta, Ga.) are added and mixed for 20 minutes. The temperature is checked, and the mixture is reheated if necessary. The temperature of the mixture is maintained constant at approximately 40° C. While stirring the mixture slowly, 19.14 Kg of miconazole nitrate (U.S.P.) are added. The heat is then turned off and while continuing agitation 102 0 g of the Carrisyn TM wet extract are added.

C. Molding of the Suppositories

The mixture is mixed well before pouring it into a conventional suppository mold, which may be made of an aluminum alloy, brass or plastic. The mixture should be poured slowly to prevent entrapment of air bubbles. The suppositories and mold are thoroughly cooled by refrigeration. After chilling the cooled suppositories, any excess product is scraped off. The mold is opened, and the suppositories are removed. It is recommended that sufficient time be allowed for cooling to permit easier removal and to minimize splitting of the finished suppository. The product is held until it is released from the quality control assurance personnel according to a standard good manufacturing process.

EXAMPLE 12

Preparation of Carrisyn ™ Ophthalmic Drops

| Preparation of Carrisyn ™ Ophthalmic Drops | | |
|---|---|---|
| | Ingredients | Amount |
| (1) | Sterile D.I. Water (73 gals) | 276 Kg |
| (2) | Carrisyn ™ Wet Extract | 284 Kg |
| (3) | Boric Acid | 5.7 Kg |
| (4) | Sodium Chloride | 1.1 Kg |
| (5) | Disodium EDTA NF | 567 g |
| (6) | Methocel E4M Premium NF | 284 g |
| (7) | Benzalkonium Chloride NF | 56.7 g |
| (8) | Sodium Metabisulfite NF | 112.2 g |

A. Required Sanitization of Equipment

Previously uconventionally-cleaned tanks, mixers and fittings (see Example 9 above) should be sanitized with 50% isopropyl alcohol (IPA) solution (Delta, Dallas, Tex.) and then rinsed free of the alcohol with hot D.I. (deionized) water. A 5% calcium hypochlorite (York Chemical, Dallas, Tex.) solution is then drained through pumps and attached hoses which are then flushed with 50% IPA solution and finally flushed with hot D.I. water until the apparatus is free of IPA. A suitable homogenizer (and attached hoses) and pumps are then sanitized with 50% IPA solution and are flushed with hot D.I. water until free of IPA. A 5% solution of calcium hypochlorite is prepared and circulated through the entire diatomaceous earth filter system for 20 minutes. The previously conventionally-cleaned 0.2 micron filter and housing are then sanitized using 50% IPA solution.

B. Manufacture 73 gals (276L) of D.I. water and Sodium Metabisulfite (General Chemical, Parsippaney, NJ) are added to the 100 gallon stainless steel tank. Agitation is then started and the Carrisyn ™ wet extract is collected from the 1000 gallon mixer into the collection tank of Example 9 to make a total volume of 150 gallons (567 L). The tank is then removed to the compounding area as above and the previously sanitized homogenizer is set at 1500 psig pressure and is connected to the collection tank. The homogenizer is started, and the product is discharged to the open stainless steel basket that has been mounted in a suitably-sized jacketed stainless steel tank. The starting and stopping times of homogenizing should be noted. All 100 gallon portions manufactured are added to the 1000 gallon stainless steel tank.

The sanitizing solution is flushed from the diatomaceous earth filter using hot D.I. water, 1 Kg of diatomaceous earth (Eagle Pitcher Co., Tulsa, Okla.) is added to 10 gallons of D.I. water and mixed until a suspension is obtained. The mixture is circulated through the diatomaceous earth filter until the water is clear. Excess water is flushed from this filter with the Carrisyn ™ extract and then circulated through the filter. While mixing, the Carrisyn ™ product is heated to 90° C. The following chemicals are added, while mixing is continued, until the solution is entirely homogeneous: boric acid (Hancock, Fort Worth, Tex.), sodium chloride (Morton Salt Div., Richardson, Tex.), disodium EDTA (Dow Chemical, Houston, Tex.) and benzalkonium chloride (Ruger Chemical, Hillside, N.J.). The product is allowed to cool overnight.

The following day, the solution is heated to 90° C. while agitating and then allowed to cool to 27° C. While mixing, the Methocel ™ E4M Premium (Dow Chemical, Houston, Tex.) is added to the mixing tank and solvated. When solvated, the product is filtered through a Romicon 0.2 micron filter (Amicon USA Corp., Danvers, Ma.). The pH is checked and recorded. The desired pH is 6.0±0.5, and sodium hydroxide (Sargent Welch, Dallas, Tex.) can be used to adjust the pH if necessary. The final pH is recorded. The osmolarity is checked and recorded. The desired osmolarity is 290±20; sodium chloride can be used to adjust the osmolarity if necessary. The final osmolarity is recorded. When a sample has been approved according to good manufacturing procedures, the product is pumped into drums, and the drums are sampled for micro tests. The product is held until released by proper quality control and assurance personnel.

EXAMPLE 13

Preparation of Carrisyn ™ Wound Irrigation Solution

| Preparation of Carrisyn ™ Wound Irrigation Solution | | |
|---|---|---|
| | Ingredients | Amount |
| (1) | D.I. Water (40 gals) | 152.0 L |
| (2) | Methylparaben | 948.0 g |
| (3) | Imidazolidinyl Urea NF (Germall 115) | 948.0 g |
| (4) | Quaternium-15 NF (Dowicil 200) | 758.0 g |
| (5) | Potassium Sorbate NF | 758.0 g |
| (6) | Sodium Metabisulfite NF | 76.0 g |
| (7) | Carrisyn ™ extract gel (50 gals) | 224.0 L |
| (8) | Sodium Lauryl Sulfate NF | 190.0 g |

A. Sanitization

The previously cleaned tanks, mixers and fittings of Example 9 are sanitized with 50% isopropyl alcohol (IPA) solution (Delta Solvents and Chemicals, Dallas, Tex.) and said equipment is rinsed free of IPA with D.I. water. The 5% solution of 65% calcium hypochlorite (York Chemical, Dallas, Tex.) is drained from pumps and attached hoses. The equipment is then flushed with D.I. water. The pump, homogenizer and attached hoses are sanitized with 50% IPA solution and flushed with D.I. water until the apparatus is free of IPA.

The previously-cleaned Leslie's ™ diatomaceous earth filter of Example 9 is disassembled and all parts are placed into a 5% solution of 65% calcium hypochlorite for 15 minutes. All parts are replaced into the pool filter. A solution is prepared of 10 gallons of D.I. water and 400 grams of 65% calcium hypochlorite. The solution is circulated through the entire system for 20 minutes. The entire system is then rinsed with D.I. water for 30 minutes or until free of chlorine.

B. Manufacture

Forty gallons (152 L) of D.I. water are added to the collection tank. The following chemicals are dissolved with agitation in the D.I. water: methylparaben (Sutton Labs, Chatham, NJ), imidazolidinyl urea (Sutton Labs, Chatham, NJ), Quaternium-15 (Dow Chemical, Houston, TX), potassium sorbate (Miles, Elkhart, Indiana) and sodium metabisulfite (General Chemical, Parsippaney, NJ). With continued agitation, Carrisyn TM extract is collected from the grinder into the collection tank to make a total volume of 100 gallons (379 L). The tank is moved to the compounding area as before: the previously sanitized homogenizer is set at 1500 psig pressure and connected to the collection tank. The homogenizer is started, and the product is discharged into the 1,000 gallon stainless steel tank. Agitation is started when the product covers the mixer blades as before. The sodium lauryl sulfate (Du Pont, Wilmington, DE) is added while the mixer continues to agitate at slow speed. All 100 gallon portions manufactured are added to the 1,000 gallon tank as in the previous example, and the product is allowed to set overnight.

The sanitizing solution is flushed from the diatomaceous earth filter using D.I. water. One Kg of diatomaceous earth (Eagle Pitcher Co., Tulsa, Okla.) is added to 10 gallons of D.I. water and mixed until suspended. The mixture is circulated through the diatomaceous earth filter until the water is clear. The excess water is flushed from the diatomaceous earth filter with product, and the product is circulated through the filter until it is clear. The solution is held until released from the quality control and assurance personnel according to good manufacturing practices.

EXAMPLE 14

Preparation of Carrisyn TM Moisture Barrier Cream

| Preparation of Carrisyn TM Moisture Barrier Cream | | |
|---|---|---|
| | Ingredients | Amount |
| (1) | Lyophilized Carrisyn TM powder (U.S. Pat. No. 4,735,935) | 102.0 g |
| (2) | D.I Water | 30.6 Kg |
| (3) | Sodium Chloride USP (Morton Salt Div., Richardson, TX) | 102.0 g |
| (4) | Quaternium-15 (Dowicil 200) (Dow Chemical, Houston, TX) | 31.0 g |
| (5) | Eutra (Colleen Ryan Corp., Dallas, TX) | 957.0 g |
| (6) | Lecithin (Alcolec TM Z-3) (American Lecithin Co., Atlanta, GA) | 30.6 Kg |
| (7) | Propylparaben (Sutton Labs, Chatham, NJ) | 1.0 Kg |
| (8) | Butylparaben (Delta, Dallas, TX) | 1.0 Kg |

A. Sanitization

The previously cleaned kettle, mixers, pump, hoses and containers of Example 9 are sanitized.

B. Manufacture

The Eutra TM mixture (made from Mineral Oil, Petrolatum and Paraffin (Colleen Ryan Corp., Dallas, Tex.)) is added to the dry kettle, and agitation is started. The mixture is heated to 50° C. ±5° C. with agitation. The heat is turned off and the agitation is continued. Propylparaben and butylparaben are then added and mixed until dissolved (approximately 15 to 30 minutes). Lecithin is added and mixing is continued for 20 minutes. Carrisyn TM wet extract solution is then added to the mixture. Force-cooling with slow agitation is begun until the product is solid (approximately 25° C.). The sample is submitted for approval, and the product is held until released from the quality control and assurance personnel according to good manufacturing practices.

EXAMPLE 15

Biological Activity

It has been observed by both in and in vitro experiments that Carrisyn TM extract promotes the proliferation of fibroblast cells. Promotion by a factor of 2-3 over the control has occasionally been recorded. Table 13 illustrates fibroblast proliferation counts influenced by Carrisyn TM extract at a concentration of 0.1% (w/v) over a 72 hour period. These experiments were conducted to evaluate the cell response to samples of Carrisyn TM extract prepared under various conditions.

TABLE 13

| Effect of Carrisyn TM Extract on Fibroblast Proliferation | | | |
|---|---|---|---|
| Carrisyn TM Sample # | Conc. % (w/v) | 24 hrs. % | 48 hrs. % | 72 hrs. % |
| TCX Lab. 7/25/85 | 0.1 | 90.7 | 162.2 | 163.8 |
| Batch 1 (TCX) | 0.1 | 104.3 | 139.7 | 129.5 |
| Batch 2 | 0.1 | 72.1 | 123.2 | 144.9 |
| Batch 3 | 0.1 | 75.5 | 130.9 | 128.4 |
| Batch 4 | 0.1 | 102.3 | 131.2 | 135.1 |
| Batch 5 | 0.1 | 79.3 | 115.0 | 129.2 |
| Batch 6 | 0.1 | 57.7 | 130.9 | 113.3 |
| Batch 7 | 0.1 | 65.1 | 110.6 | 120.2 |
| Batch (Lab.) 5/83 | 0.1 | 81.1 | 138.3 | 169.7 |
| Man. Batch 1 B | 0.1 | 125.6 | 174.8 | 114.8 |
| Man. Batch 2 B | 0.1 | 103.5 | 175.3 | 118.6 |
| Man. Batch 3 B | 0.1 | 138.9 | 156.4 | 147.0 |
| Man. Batch 3 B (Hydrate) | 0.1 | 103.3 | 141.3 | 158.9 |
| Glucomannan (Konjac plant) | 0.1 | 103.3 | 69.9 | 108.6 |
| Control SCM | 0.1 | 100.0 | 100.0 | 100.0 |

EXAMPLE 16

Comparison of Common Topical Agents for Wound Treatment

Cytotoxicity for Human Fibroblasts in Culture

Cultures of human fibroblasts were used to determine the cytotoxicity of several topical agents that are commonly used to cleanse wounds. The objective was to compare a wound gel containing Carrisyn TM extract with several standard cleansing agents that have different modes of action. These standard cleansing agents are designed to reduce bacterial damage and tissue breakdown after breach of the epidermal barrier. Release of radiolabeled chromium and uptake of trypan blue dye were used to measure cytotoxicity. The cultured fibroblasts were not damaged by concentrations of Carrisyn TM extract as high as 0.5%. In contrast, povidone-iodine (Betadine), trypsin and balsam of Peru (Granulex), chlorhexidine (Hibiclens) and hydrogen peroxide released $Cr^{51}$ from labeled cells. Betadine, Hibiclens and Granulex also enhanced staining with trypan blue, but treatment with Carrisyn TM extract did not. Based upon these in vitro studies, Carrisyn TM extract appears safe for topical application and wound treatment.

Cell Cultures. Human skin fibroblasts were grown from explants of newborns' foreskins and from samples of adult skin collected from the lower abdomen at Caesarean section. The tissue was cleaned of fat and subcutaneous connective tissue, minced into 2-mm³ particles and placed into small (25 cm²) culture flasks. Culture medium, consisting of Minimum Essential Medium (MEM) (Inland Laboratories) supplemented with 5% fetal calf serum (Hazelton), 200 mM glutamine and 1% antibiotics, was added, and the cultures were maintained at 37° C. in an atmosphere of 5% $CO_2$.

A mixture of keratinocytes and fibroblasts grew from the edges of the tissue within a few days. The keratinocytes failed to divide, but within 16-21 days the fibroblasts proliferated to form monolayers of elongated cells with a characteristic swirled pattern. All cultures were passaged at least three time before use and were used for up to 10-15 passages.

Topical Agents. Several products that are commonly used to treat wounds and decubiti were added directly to standardized cultures of human fibroblasts in order to measure cytotoxicity in an in vitro system. Povidone-iodine solution (Betadine), hydrogen peroxide, Granulex and chlorhexidine (Hibiclens) are commonly used cleansing agents with different mechanisms of action. These compounds (0.001-0.5%) were compared with Carrisyn TM extract for cytotoxic effects on cultured fibroblasts.

Treatment of Cells. Cells from confluent monolayers were detached with 0.25% trypsin after a brief exposure (5-10 min) to Pucks-EDTA solution. The suspended cells were centrifuged to a pellet, washed once with fresh medium and resuspended in MEM supplemented with glutamine, antibiotics and 1% fetal calf serum. Cell number was determined in an electronic cell counter (Coulter Electronics, Hialeah, Fl.) and adjusted by dilution as required for individual experiments. The cells were labeled with $Cr^{51}$ (1 µCi/ml) and plated in 24-well multiwell plates at a density of $10^5$ per well. The plates were returned to the incubator for 18 hours. At the start of each experiment, the radioactive medium was removed by suction, and each well was washed four times with fresh MEM plus 1% fetal calf serum. MEM alone or MEM containing various dilutions of the test products was added to replicate wells, and the plates were incubated 1-30 minutes longer. At the end of the incubation period, the media were collected and reserved for measurement of released radioactivity. The cells in each well were lysed by addition of 0.5 ml of Triton X-100 (1%) with 0.1M NaOH, and samples of the lysates were taken for measurement of radioactivity.

Measurement of Cytotoxicity. Cytotoxicity was quantitated by release of radioactive chromium from labeled fibroblasts that had been incubated with the various chemical agents. The percent release was calculated by dividing the amount of radioactivity in both media and cells.

An alternate assessment of cytotoxicity was provided by staining with trypan blue. The cells were incubated with each of the test agents for 15 minutes. Trypan blue (1%) was added to each well, and incubation was continued for 5 additional minutes. The samples were inspected by light microscopy and photographed with a Nikon 35-mm camera attached to a Nikon inverted phase microscope. Cytotoxicity was estimated by determining the percentage of cells stained with trypan blue in comparison with control (untreated) cells.

TABLE 14

Cytotoxicity of Topical Preparations As Determined by Trypan Blue Staining

| Product | Conc. | Inc. Time | Percent Staining |
|---|---|---|---|
| Betadine | 0.01% | 15 min. | 100 |
| Hibiclens | 0.01% | 15 min. | 100 |
| Granulex | 0.01% | 15 min. | 100 |
| Carrisyn TM extract | 0.01% | 15 min. | 5 |
| Media Alone | — | 15 min. | 1 |

Cultured cells were incubated with each of the agents or with media alone for 15 minutes. Trypan blue (1%) was applied, and after 5 minutes the nuclei were counted. The result is expressed as the percent of the total cell nuclei within the visual field that were stained.

Figure 11:
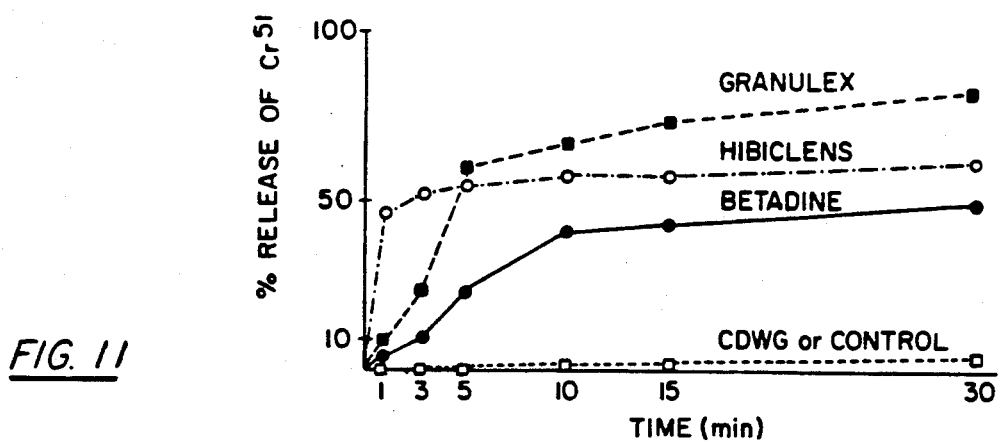
FIG. 11 shows time course of $Cr^{51}$ release by topical agents. Cultures of human fibroblasts were incubated for various times with 0.05% Granulex, Hibiclens, Betadine or Carrisyn TM extract (CDWG) and the percent of the total radioactivity release was determined. Data are means of 3-5 separate determinations at each time point. Control cells (treated with media alone) released 3-5% of the total $Cr^{51}$ during 30 minutes.

Time Course of Cell Injury. Direct cell injury by the topical agents occurred rapidly and was reflected by increased release of $Cr^{51}$ from the cells. Cultured fibroblasts that were treated with medium alone or with 10% fetal calf serum released no more than 5% of the total chromium label during incubation for 5-60 minutes (FIG. 11). In contrast, cells treated with 0.05% Granulex or Hibiclens released between 55% and 62% of the total label within 5 minutes. Betadine was somewhat less effective. Incubation for 10 or 15 minutes increased the amount released for all three agents, but longer incubation (30 minutes) did not appreciably enhance release of radioactivity. Cells treated with Carrisyn TM extract (CDWG) (0.05%) released no more than 5% of the total label during a 30-minute incubation.

Figure 12:
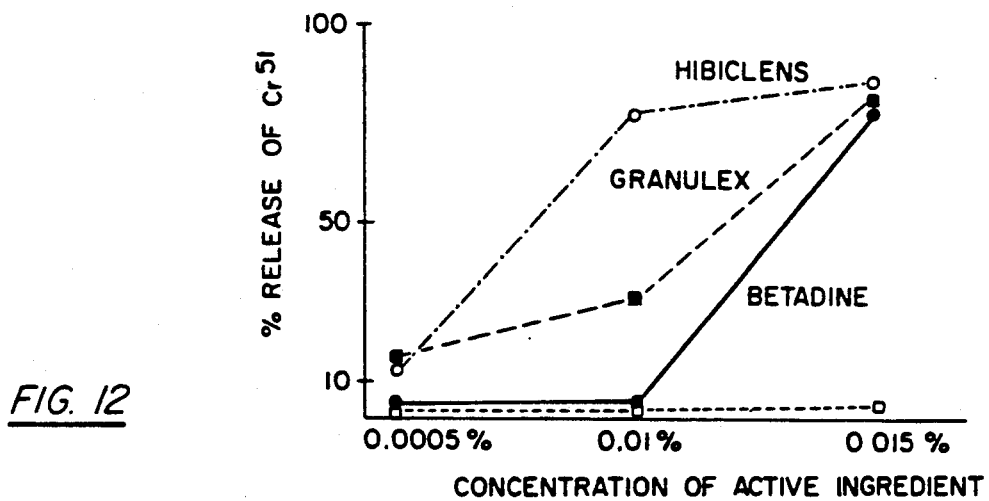
FIG. 12 shows influence of concentration on cell injury. Cultured fibroblasts were incubated with varying concentrations of Hibiclens, Granulex, Betadine or Carrisyn TM extract (CDWG) for 15 minutes at 37° C. The percentage of $Cr^{51}$ released was determined for each concentration. Control release (from untreated cells) ranged from 1-5%. Data are means of 3-5 separate determinations.

Influence of Concentration on Cell Injury. The various agents were tested for cytotoxicity in concentrations ranging from 0.005 to 0.05%. As shown in FIG. 12, Granulex and Hibiclens (0.01%) released approximately 25% and 70%, respectively, of the total chromium label from fibroblasts. Release by the lowest concentrations of Betadine (0.005 and 0.01%) was no greater than that by medium alone, but cells exposed to 0.015% Betadine released more than 70% of their total radioactivity. Carrisyn TM extract in concentrations up to 0.5% released no more than medium alone.

Similar results were obtained when trypan blue staining was used to assess cell injury. As shown in Table 14, incubation for 15 minutes with 0.01% Betadine, Hibiclens or Granulex killed 100% of the cells. Incubation with Carrisyn TM extract at the same concentration killed only 5%. Hydrogen peroxide at a concentration of 0.01% badly damaged the cells as judged by changes in morphology, but trypan blue staining by this agent could not be measured because of its decolorizing effects.

Figure 13:
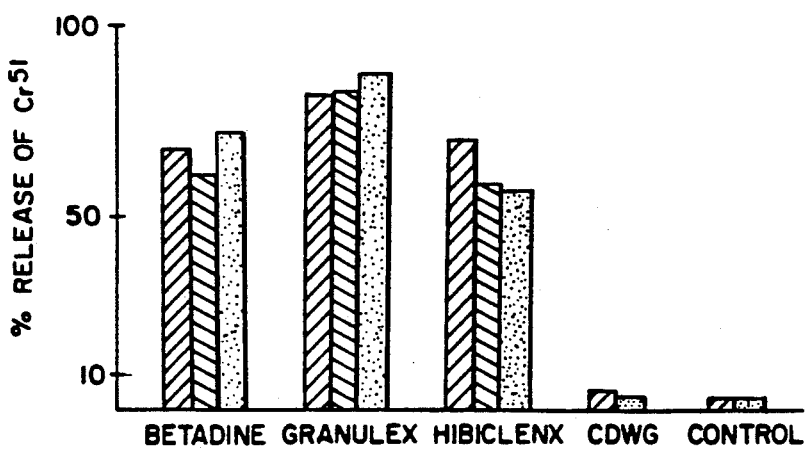
FIG. 13 shows release of chromium: effect of CDWG and serum. Cells were incubated in medium alone (dark bars) or in medium containing Carrisyn TM extract (0.5%) (hatched bars) or medium with 10% fetal calf serum (strippled bars) for 15 minutes. Betadine, Granulex or Hibiclens (0.15%) were added and the incubation was continued for 15 minutes longer. Data are means of 3-4 separate experiments.

Effects of Combined Agents. In some experiments Carrisyn TM extract was added to fibroblast cultures before addition of other topical agents to determine if the extract had a protective effect. The cytotoxic effect was measured in medium alone and in medium that contained 10% fetal calf serum. FIG. 13 shows that although Carrisyn TM extract alone did not damage the cells, it did not alter the amount of $Cr^{51}$ released by Betadine, Granulex or Hibiclens during a 15-minute incubation period. Similarly, inclusion of fetal calf serum in the incubation medium did not alter the cytotoxic effects of these agents.

For an independent evaluation of the effects of an unlyophilized, unstabilized earlier version of Carrisyn TM extract on burn tissue in animals, see Miguel Rodriguez-Bigas et al., "Comparative Evaluation of Aloe Vera in the Management of Burn Wounds in Guinea Pigs", 81 Plastic and Reconstructive Surgery 81:386 (1988).

EXAMPLE 17

An 83 year old female patient, TB, developed an ulcer, 25 mm in diameter, on the lateral margin of her left foot. The ulcer had been present for several months and had failed to respond to several treatment regimens.

The wound was treated with the product of Example 3 of U.S. Pat. No. 4,735,935 and the product of Example 7 of U.S. Pat. No. 4,735,935 using a three times daily treatment schedule. The clean wound was soaked for 15 minutes with the product of Example 2 of U.S. Pat. No. 4,735,935. Excessive product was absorbed from the wound with a dry sterile 4×4 gauze. The product of Example 7 of U.S. Pat. No. 4,735,935 was then applied in a quantity sufficient to cover the wound and to prevent wound dehydration between dressing changes.

The progression of wound healing was measured by interval photographs and planimetry of the wound defect. The progression of wound closure is shown in Table 15.

TABLE 15

Progression of Wound Healing

| Day | Wound Area (Sq. In.) | Percentage of Healing |
|---|---|---|
| 1 | 1.24 | 0.00 |
| 28 | 0.51 | 58.87 |
| 77 | 0.29 | 76.61 |
| 83 | 0.12 | 90.32 |
| 97 | 0.00 | 100.00 |

The epidermal defect was substantially closed in 12 weeks; complete closure occurred in 14 weeks.

EXAMPLE 18

A 32 year old patient was presented with a history of ulcerative colitis for "many years". During an active episode, she had been unresponsive to a daily regimen of 40 mg prednisone, 3 grams Azulfidine, 50 mg 6-mercaptopurine and Flagyl. She continued to have a painful abdomen and 4–8 bloody bowel movements per day. She was placed on hyperalimentation. Endoscopic findings revealed severe ulcerations in the ascending colon with mild hepatic to transverse ulcerations. The patient was placed on 50 mg of Carrisyn TM extract four times daily in addition to her other medications and sent home. In 1 week, her symptoms were virtually gone. Her abdomen was mildly tender, and endoscopy revealed a healed and mildly congested mucosa. She was slowly taken off other medications, and the clinical picture continued to improve. The patient was maintained on Carrisyn TM extract as the sole medication, and her physical exam and symptoms were recorded as totally normal.

Five additional cases with similar responses to ulcerative colitis and Crohn's disease have been seen. One patient ran out of Carrisyn TM capsules. In 4 weeks, mild symptoms began to recur (there was increased stool with mild abdominal discomfort), and she returned for a supply of medication. In 3 days she was back to total normal bowel symptomatology.

EXAMPLE 19

A number of AIDS patients have received prolonged treatment with high doses of Carrisyn TM extract without toxicity or side-effects. A rise in T-4 and T-8 lymphocyte ratios and an increase in absolute T-4 counts was seen in these patients, with a reduction and elimination of clinical symptoms as well as a reduction in opportunistic infections.

Since stimulation to the lymphocytes of these patients was observed, it appears that Carrisyn TM extract may be involved in immune modulation.

EXAMPLE 20

Tic douloureux, or neuralgia of the fifth cranial nerve, is characterized by attacks of severe, unbearable pain over one or more branches of the trigeminal nerve. The pain usually is transient, and attacks may be precipitated by touching some area of the face—the so-called trigger zone.

The cause and cure of this painful disease are unknown. Several attempts to treat the disorder have met with little or no success. Various treatments have included analgesics, phenytoin, peripheral avulsion of the involved nerve branch as it leaves the skull and injection of 98% alcohol into the gasserian ganglion.

A more drastic treatment—sectioning the sensory root of the nerve proximal to the ganglion—leaves the patient permanently without sensation in the area supplied by the sectioned nerve. Another recent treatment attempt uses carbamazepine and phenoliophendylate injections. However, these injections can be complicated by painful numbness and serious side effects.

None of the previously cited treatments is desirable.

A 43 year old woman was diagnosed as having tic douloureux. The affected area included the first and third divisions of the trigeminal nerve on the right side.

The patient could trigger the pain by brushing or combing her hair on the right side. She had been treated unsuccessfully with diazepam (Valium), antihistamines, analgesics, propranolol hydrochloride (Inderal) and phenobarbital. The patient said she had not had a pain-free day since the onset of the disease.

The proposed therapy involved drinking 1 to 2 oz. of the product of Example 2 U.S. Pat. No. 4,735,935 daily for 3 months. After that period, the therapy was evaluated.

The patient's pain diminished significantly within 2 weeks of initiating therapy. She said she felt well for a few weeks. However, she then went on a 2-week trip, during which she did not drink the product, and symptoms and pain returned. After she resumed the medication, however, the pain disappeared within a few days. For the next few weeks, she again felt well.

After drinking the juice daily for more than 6 months without interruption, she reports that she can brush and comb her hair without triggering the pain. Her appearance has improved, and she says she feels better than ever before.

EXAMPLE 21

Results Obtained Using Oral Aloe Drink in 41 Symptomatic HIV Patients, Including Development of Tentative Diagnostic Criteria for Patient Response A first two-year clinical pilot was performed under Texas and Federal INDs on 14 ARC-AIDS patients to determine whether aloe drink or a freeze-dried extract of aloe (Carrisyn TM extract) produced evidence of clinical benefit for HIV-1 patients. Tests to establish the diagnosis of HIV infection and to monitor patient responses were either nonexistent, not available or primitive when this pilot was begun. In this study, it was found that an intake of between 500 mg/day and 1000 mg/day of Carrisyn TM extract constituted a threshold dose for clinical response. Eight patients in the pilot ARC-AIDS group who had no recognized untreatable condition achieved a 71% improvement in modified Walter Reed clinical scoring at 90 days of therapy. Six pilot AIDS patents with advanced disease and severe complications recorded a 20% gain in their clinical scoring. Thus the less advanced patients improved more rapidly and progressed to a higher state of health. An independent academic statistician analyzed the data and concluded that patient improvement was attributable to treatment at the 99.5 percent confidence interval. The result of this pilot study justified collection and analysis of data from patients who had been subjected to the more objective evaluation techniques that were becoming available at the time the pilot was being concluded. In the first such study 15 patients were analyzed, and these are referred to herein as "Pulse-McDaniel Group". A second group of 26 patients was also analyzed and are herein referred to as the "Watson-McDaniel Group".

A. General Approach to Evaluation of Patients under Treatment (First and Second Groups)

The general approach to documenting the results of treatment with aloe drink in these pilots was as follows:

1. The patient group was composed of HIV symptomatic patients treated with 20 fl. oz. per day of oral aloe drink produced by Carrington Laboratories, Inc.[1]

[1] Formula for all aloe Drink Prescribed for AIDS Patients: 1985-1988

| Component | % w/w |
|---|---|
| D.I. Water | 40.00 |
| Sodium benzoate, USP | 0.10 |
| Glycine, FCC | 0.80 |
| Citric acid, USP | 0.11 |
| Potassium sorbate, USP | 0.05 |
| Sodium metabisulfite, FCC | 0.02 |
| Raw Aloe vera gel | 58.56 |
| Flavoring agents: | |
| "Adams Best" brand vanilla extract | 0.032 |
| Natural cinnamon oil, FCC | 0.002 |
| "Real" brand lime juice | 0.128 |
| "Adams Best" brand lemon extract | 0.198 |
| | 100.000 |

Vitamin E added as an antioxidant.

2. These were retrospective studies to analyze the records of patients to whom this particular aloe drink had been prescribed by the physician and therefore no placebo or blind component was available.

3. Study patients were encouraged to avoid underground drugs and additional medications alleged to be useful for HIV therapy. It was stressed they must inform their physicians of all medications taken; however, each patient was advised that taking drugs would not be a basis for removal from the aloe drink treatment.

4. Clinical evaluations were performed by an independent physician using a modified Walter Reed clinical scoring sheet.

5. All clinical data were treated as confidential and maintained in the standard chart packet.

6. Confidentiality of patient identity and results were maintained. Code numbers were assigned to charts and all records.

B. Assessment Criteria

A favorable patient response to therapy was defined as a combination of clinical and laboratory findings consisting of a reduction in the modified Walter Reed clinical score, an increase in absolute T-4 lymphocytes of more than and core antigen levels that either remained negative or decreased more than 10% from the previous assay for each evaluation interval.

Patients were selected on the following basis:

1. HIV antibody positive with Western Blot confirmation by two or more reactive virus antigens.

2. At least one symptom typical of acquired immunodeficiency syndrome.

3. The target population was patients with an absolute T-4 helper lymphocyte count of 150 to 350 mm$^3$. However, some patients with values above or below this range were taken.

4. There was no age, race or sex exclusion in the study group.

5. All patients were required to be outpatients and not in an experimental study group for other investigators. Conditions imposed by this evaluation acted to select less debilitated HIV patients.

6. The proposed treatment was received and approved by the Investigational Review Board for Human Experimentation of Dallas-Ft. Worth Medical Center. The plan was an extension of the individual Physician Investigational New Drug Exemption. Patients were appraised of these facts in their informed consent session.

Parameters Monitored

1. History and physical examination, plus particular emphasis on the modified Walter Reed clinical scoring.
2. HIV antibody and Western Blot.
3. Complete blood count with platelets.
4. 21-test biochemical profile.
5. Serum core antigen assay (P-24) Abbott Diagnostics
6. Quantitative fluorescent flow cytometry of T-4 and T-8 lymphocytes with ratio.
7. Culture of FICOL separated white cells in 1986-87 pilot.
8. Delayed skin test antigens on 1986-87 pilot.

C. Results

Figure 14:
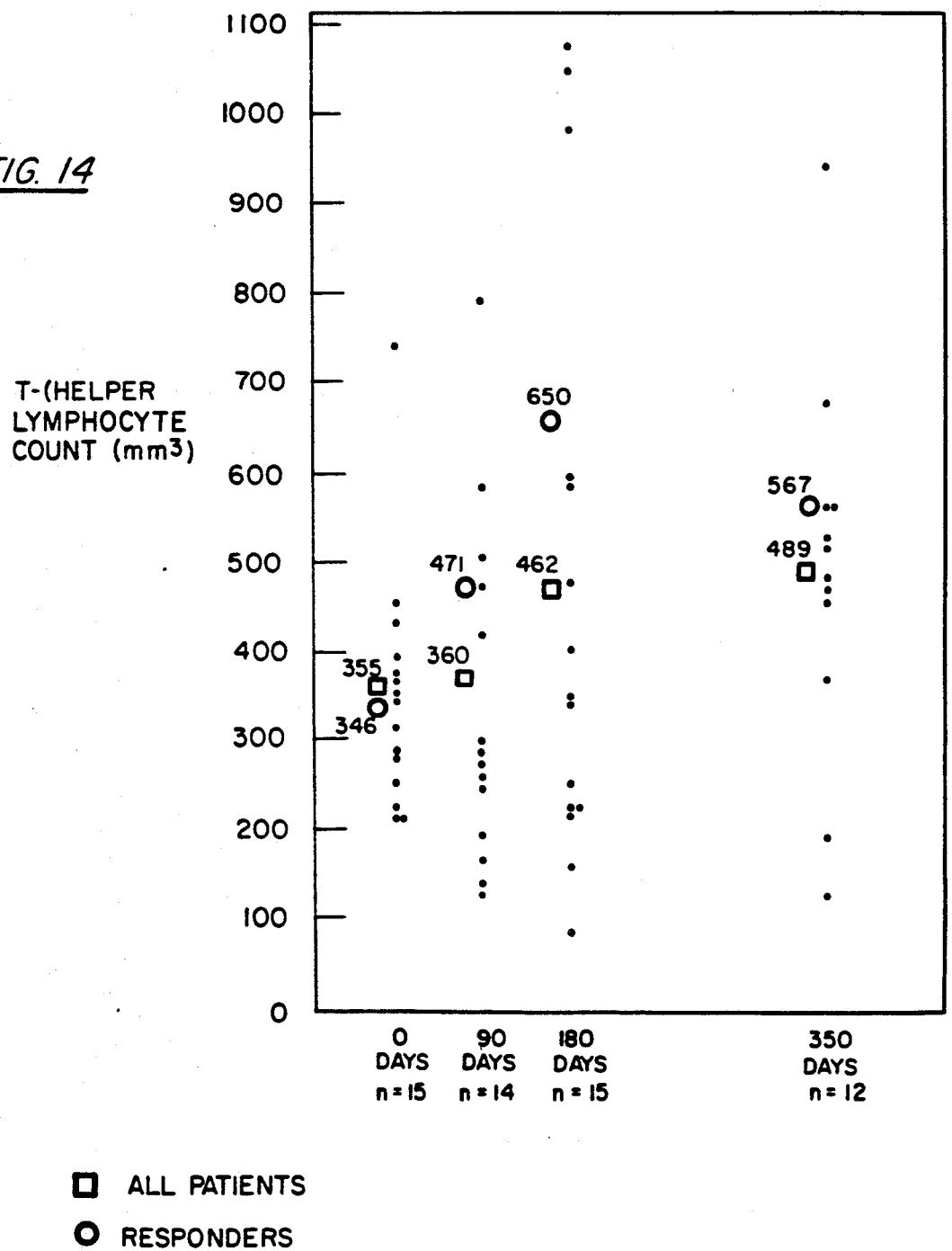
FIG. 14 is a graph presenting data reflecting change in absolute T4 helper lymphocyte count ($mm^3$) in 15 HIV-infected patients administered aloe drink for 350 days in tests on a test first group (Pulse-McDaniel Group).
Figure 15:
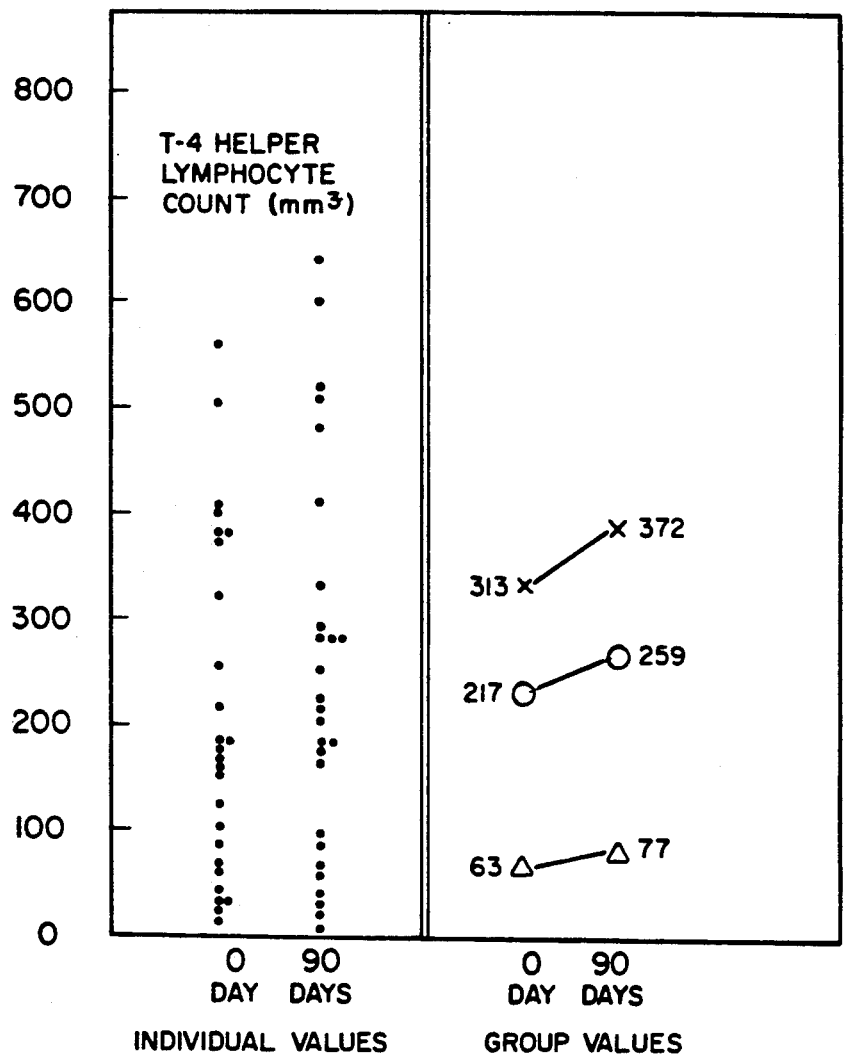
FIG. 15 is a graph presenting data reflecting change in absolute T4 helper lymphocyte count ($mm^3$) in 26 HIV-infected patients administered oral aloe drink for 90 days in tests on a test second group (Watson-McDaniel Group).

Data collected from HIV patient records in the Pulse-McDaniel group of patients indicate that the average absolute T-4 helper lymphocyte counts in the 15 patients rose from 355 initially to 360 after 90 days treatment with oral aloe drink. After 180 days the average count in these same patients had risen to 462, and in the 12 patients for whom data were available at 350 days, the average absolute T-4 helper lymphocyte count was 489 (FIG. 14). In the Watson-McDaniel group the average absolute T-4 helper lymphocyte count in 26 patients rose from 217 initially to 259 after 90 days treatment with oral aloe drink (FIG. 15). In view of these data it is concluded that the aloe drink had a favorable effect on T-4 helper lymphocyte counts.

The standard Walter Reed Scale was modified to eliminate life-style or at-risk population and status of HIV antibody because the treatment was not expected to have an impact on these parameters. In addition, the patients' individual complaints and physical findings were added to the assessment scoring sheet if deemed by the physician to be related to the HIV syndrome.

Figure 16:
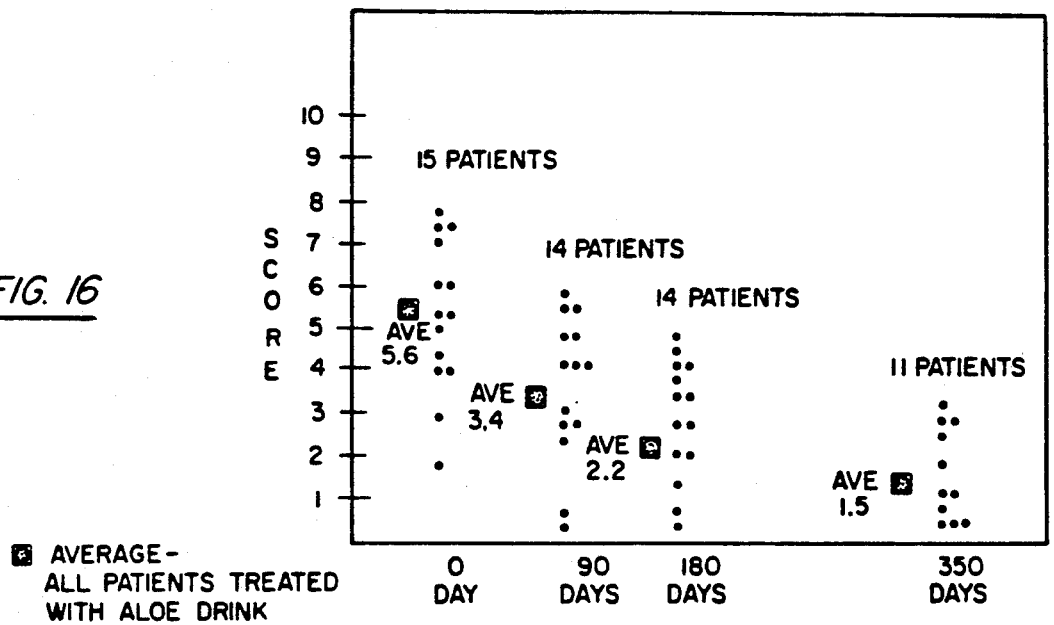
FIG. 16 is a graph showing modified Walter Reed Clinical scores in 15 HIV patients administered oral aloe drink for 350 days in tests on the first group mentioned above (Pulse-McDaniel Group).
Figure 17:
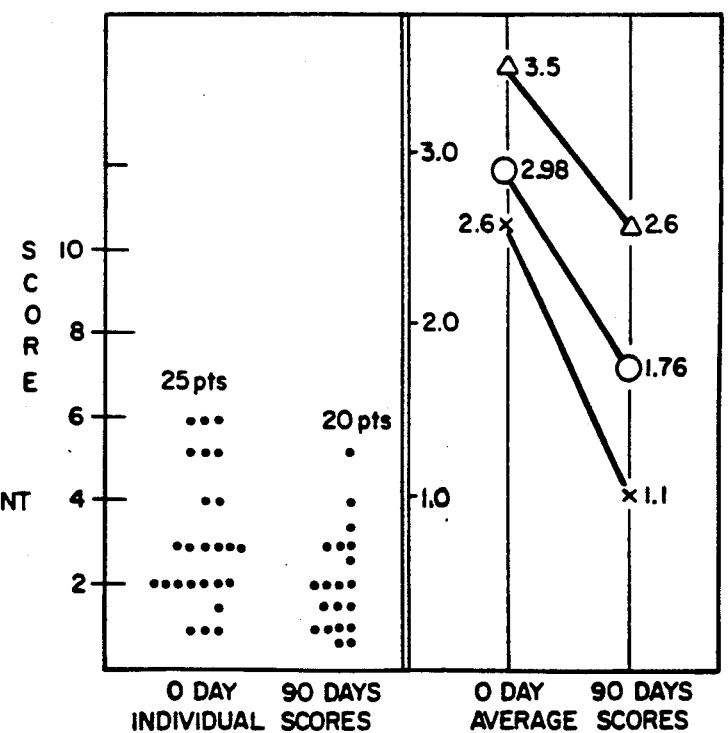
FIG. 17 is a graph showing modified Walter Reed Clinical scores in 26 HIV patients administered oral aloe drink for 90 days in tests on the second group mentioned above (Watson-McDaniel Group).

Utilizing this modified scale, the records of patients in the Pulse-McDaniel group indicate that the initial average score of 5.6 fell to 3.4 at 90 days, to 2.2 at 180 days and to 1.5 at 350 days (FIG. 16). In the Watson-McDaniel group the initial average modified Walter Reed score of 2.98 decreased to 1.76 in the 26 patients reviewed (FIG. 17). In the figure, the average scores are also shown for two subgroups: one group of 16 patients predicted to have a favorable response to treatment and another group of 10 patients predicted to have a poor response. The average scores of both groups decreased; however, the score of the 16 predicted to respond favorably changed from 2.6 to 1.1, whereas the score of the other group declined from 3.5 to 2.6, indicative of a slower rate of improvement for the latter group as illustrated by the slopes of the lines (see FIG. 17).

Figure 19:
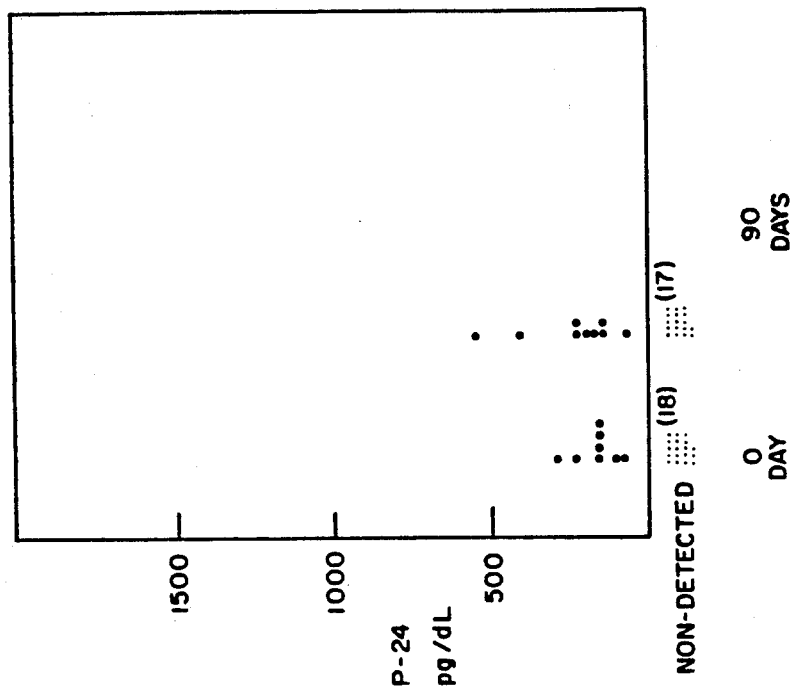
FIG. 19 is a graph showing serum core antigen (Abbott Diagnostics) in P-24 pg/dL in 26 HIV patients administered oral aloe drink over a period of 90 days in tests on second group (Watson-McDaniel Group).
Figure 18:
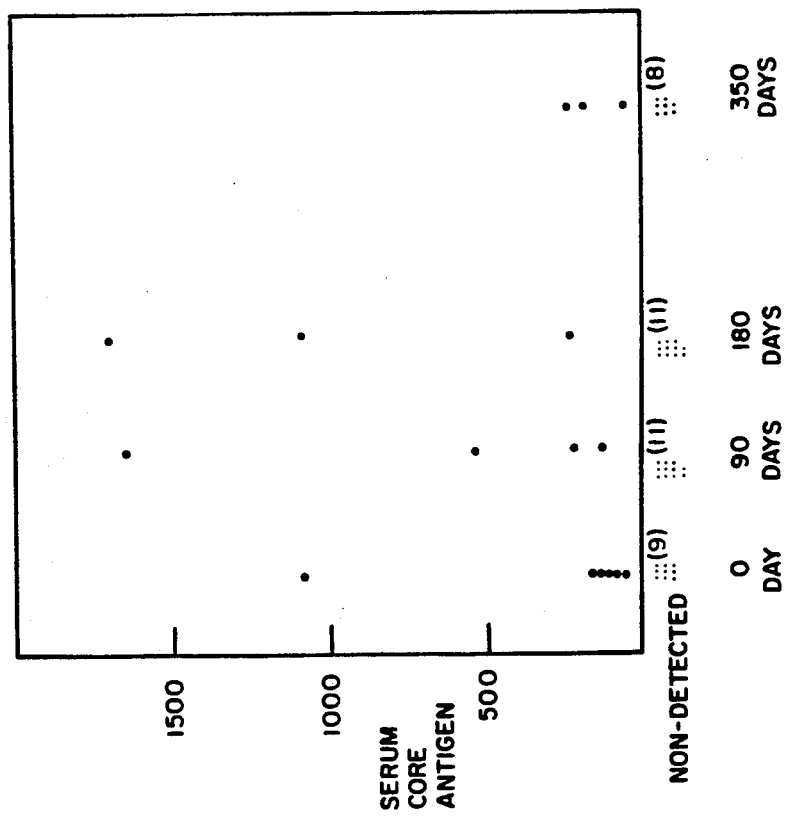
FIG. 18 is a graph showing serum core antigen (Abbott Diagnostics) in P-24 pg/dL in 15 HIV patients administered oral aloe drink over a period of 350 days in tests on the first group mentioned above (Pulse-McDaniel Group).
Figure 20:
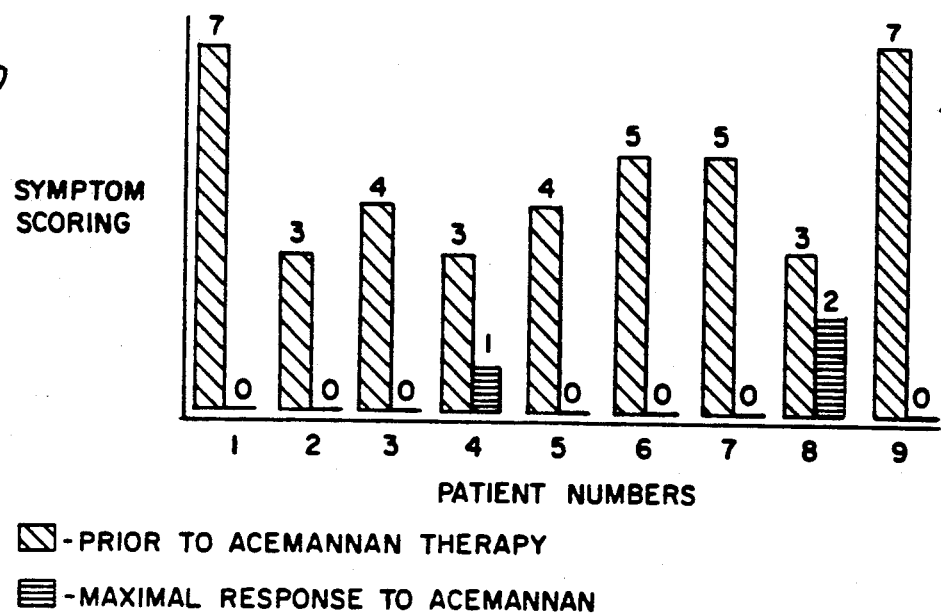
FIG. 20 is a graph showing clinical evaluation scoring of patients with inflammatory bowel syndrome in response to acemannan therapy.
Figure 21:
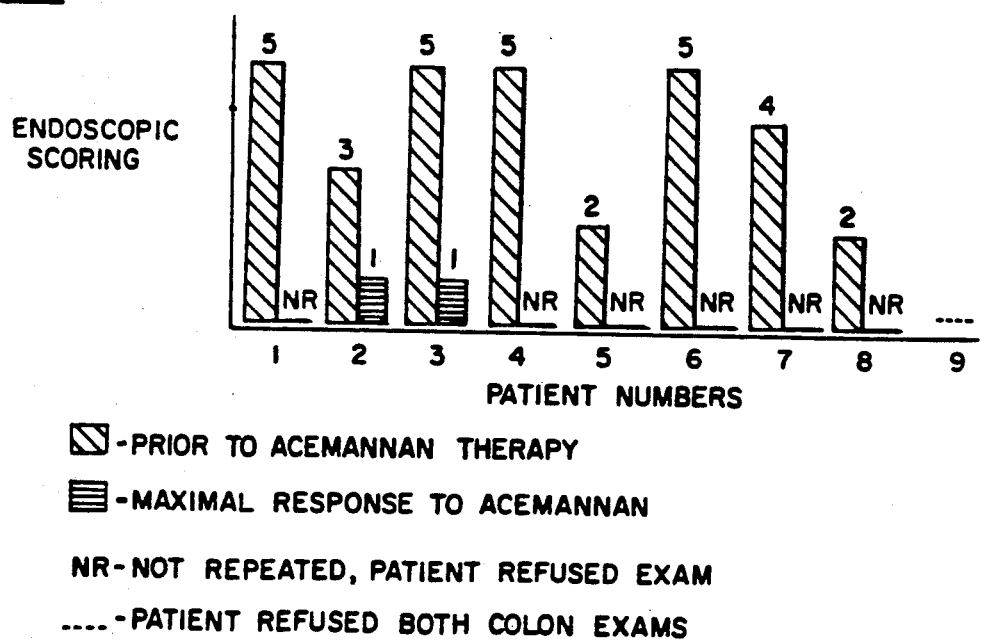
FIG. 21 is a graph showing endoscopic evaluation of patients with inflammatory bowel syndrome in response to acemannan therapy.

In the patient records for the Pulse-McDaniel group, six of the 15 HIV patients had detectable serum core antigens initially. At 90 days, four patients tested positive. In 180 days, three of 14 patents tested positive, and at 350 days three of 11 tested positive (see FIG. 18). In the Watson-McDaniel study similar results were observed. A decrease in serum core antigen was suggested by the data; however, the differences did not appear to be significant (see FIG. 19).

Because the pre-treatment absolute T-4 lymphocyte levels (ABT-4) and P-24 core antigen levels appeared to identify which patients would respond favorably to an oral daily dosage of 20 fl. oz. of aloe drink, in the Pulse-McDaniel group, 15 HIV patients were stratified into two groups, designated as those responsive and those non-responsive to the aloe drink.

The hypothesis developed from the results of the Pulse-McDaniel group was as follows: "Patients will favorably respond to aloe drink if both the initial absolute T-4 lymphocyte level is more than 150 $mm^3$ and the initial HIV core antigen (P-24) is negative or less than 300 pg/dL. Conversely, patients will respond poorly to aloe drink if both the initial absolute T-4 lymphocyte count is less than 150 $mm^3$ and the initial HIV core antigen level is greater than 300 pg/dL."

In the Watson-McDaniel group, these putative prognostic criteria were prospectively applied. Sixteen patients met favorable prognostic criteria (ABT-4>150 $mm^3$, P-24<300 pg/dL). Within 90 days thirteen patients (81 percent) improved as predicted, and three had mixed and/or minor responses (see Table 16). Of the ten patients who had poor entry prognoses (ABT-4<150 $mm^3$, P-24>300 pg/dL), seven responded poorly as predicted; however, two met all improvement criteria and one had a mixed response. Overall, 20 of the 26 patients (77 percent) had responded as predicted after 90 days treatment. Fifteen of 26 patients (58 percent) met all improvement criteria at every evaluation interval (ABT-4 increase>10 percent, negative or decreasing P-24 and the modified Walter Reed clinical score reduced). Table 16 shows the ratio of T-4/T-8 helper-suppressor lymphocyte ratios for 11 patients on whom data was available for each of the four time periods (0, 90, 180 and 350 days).

TABLE 16

Summary of the Application of Prognostic Criteria to 26 Patients, Status After 90 Days Treatment with Aloe Drink in the Second Group*

| Response Category | Criteria Status | No. | Percent |
|---|---|---|---|
| 16 Patients | All Criteria Improved | 13 | 81% |
| Predicted Favorable | Mixed & Minor Response | 3 | 19% |
| Response to Treatment: | Poor Response | 0 | 0% |
| 10 Patients | All Criteria Improved | 2 | 20% |
| Predicted Poor | Mixed & Minor Response | 1 | 10% |
| Response to Treatment: | Poor Response | 7 | 70% |

TABLE 16-continued

Summary of the Application of Prognostic Criteria to 26 Patients, Status After 90 Days Treatment with Aloe Drink in the Second Group*

| Response Category | Criteria Status | No. | Percent |
|---|---|---|---|
| Summary: | | | |
| Twenty-six (26) Patients on 90 Days Treatment Therapy: | | | |
| 15 Patients | Met All Improvement Criteria | | 58% |
| 4 Patients | Mixed & Minor Response | | 15% |
| 7 Patients | Uniformly Poor Response | | 27% |
| 20 Patients | Responded as Predicted | | 77% |

*Watson-McDaniel Group

TABLE 17

T-4/T-8 Helper-Suppressor Lymphocyte Ratios for 11 Patients on Whom Data is Available for Each Time Period in the Pulse-McDaniel Study Group

| Patient ID# | Days Treatment | | | |
|---|---|---|---|---|
| | 0 | 90 | 180 | 350 |
| 20 | 1.13 | 0.66 | 1.66 | 1.03 |
| 26 | 0.82 | 0.60 | 0.76 | 0.69 |
| 31 | 0.26 | 0.91 | 0.63 | 1.10 |
| 33 | 0.86 | 0.46 | 0.52 | 0.43 |
| 35 | 1.00 | 0.88 | 1.04 | 1.07 |
| 41 | 0.82 | 0.75 | 1.29 | 1.10 |
| 42 | 0.60 | 0.30 | 0.67 | 1.05 |
| 43 | 0.56 | 0.58 | 0.88 | 1.63 |
| 50 | 0.68 | 1.00 | 1.09 | 0.92 |
| 52 | 0.83 | 1.17 | 0.73 | 1.16 |
| 55 | 1.28 | 0.81 | 0.49 | 1.04 |
| Mean | 0.80 | 0.74 | 0.89 | 1.02 |
| Number of Patients at or Above 1.0: | 3 | 2 | 4 | 8 |

In both the Pulse-McDaniel and Watson-McDaniel groups (15 plus 26 patients), 24 of 41 patients, or 59 percent, exceeded or met the above-described improvement criteria at 90 days therapy. This tread of clinical and laboratory improvement in patients who were expected to do well continued for up to 350 days. No hematologic or biochemical evidence of damage or suppression of function in bone marrow, liver, kidney or other organs was detected. These 41 HIV-infected patients receiving aloe drink showed no toxicity and reported no significant, consistent of specific adverse effects that could reasonably be attributed to the aloe drink.

EXAMPLE 22

An Exploratory Clinical Pilot Study Utilizing Acemannan in Inflammatory Bowel Disease Inflammatory bowel disease (IBD) is a collective term for Crohn's disease and ulcerative colitis. Crohn's occurs mainly in the ileum and colon, whereas ulcerative colitis is limited to the colon. At least three credible hypotheses have been set forth to explain the etiology of IBD. One holds that an unknown infectious agent, such as a slowly growing bacterium or virus, triggers the immune system and sets up a chronic inflammatory response. The second holds that this same sequence of events is caused by a toxic substance, such as food borne or environmental contaminants. The third hypothesis suggests that the inflammatory response is an autoimmune condition. However, the precise cause(s) of the disease remains unknown.

A. Patient Selection

Patients were selected without regard to age, sex, racial or ethnic background, and all patients were volunteers. Each received an informed consent briefing by the physician, and each was required to sign an informed consent form.

Only patients with a combination of the following symptoms and signs of IBD were admitted:
1. Number of bowel movements (diarrhea)
2. Blood in stool (occult blood)
3. Excess mucus production
4. Spontaneous abdominal pain
5. Abdominal pain on palpation
6. Constant cramping
7. Other (weight loss, etc.)

The above symptoms were used to arrive at a clinical evaluation score of zero to seven with one indicating a single symptom and seven indicating all symptoms were present. A score of zero indicated the patient was asymptomatic.

B. Endoscopic Evaluation

Endoscopy was utilized to score patients pre- and post-therapy according to the following criteria:
Ulcerations
    Confluent
    Spotty
    Linear
    Segmental
Hyperemia
Exudate
Other The above endoscopic observations were used to arrive at a scale of zero to five, with one indicating a single symptom and five indicating all symptoms were present. A score of zero indicated the patient was asymptomatic on endoscopy.

C. Histological Evaluations

Scoring of histological findings was recorded as follows:
Exudate
Ulcerated mucosa
Edema
Plasma cells
Lymphocytes
Polymorphonuclears
Eosinophiles
Granulomas
Crypt abscess
Fibrosis
Other The above clinical, endoscopic and histopathological criteria were used to grade manifestations of IBD and to quantitate response to acemannan treatment. Physical examinations with endoscopy and histological sampling were limited to regularly scheduled visits. Patients were permitted to withdraw at any time without cause and without impact upon their usual therapy. Acemannan was furnished by Carrington Laboratories, Inc.

D. Clinical Results

Nine IBD patients were admitted and were treated daily with 200 mg acemannan in capsules. Patients ranged in age from 14 to 46 years and included four females and five males. Typically, the patients had abdominal pain, diarrhea or multiple bowel movements; the stools were usually bloody and watery with an increase in mucus production or a combination of these elements. Initial endoscopic examination revealed a spectrum of mucosal alterations ranging from vascular congestion with mucosal friability to focal, extensive and confluent ulcerations, termed "pan-colitis". Histological examination of bowel biopsies revealed damage ranging from a non-specific increase in chronic inflammatory cells to frank ulceration with numerous polymorphonuclear cells and eosinophiles. Two patients had microgranulomata and crypt abscesses. All patients were presented as non-responsive to conventional agents, including one or more of the following: Azulfidine, prednisone, 6-mercaptopurine and Flagyl. Imodium and tranquilizers were often added to the above agents.

The response to medication was uniformly favorable, with all scores improving in all patients (FIGS. 20-23). The average pre- and post-medication scores were as follows:

| | |
|---|---|
| Average pre-treatment clinical score | 4.56 (average of nine patients) |
| Average post-treatment clinical score | 0.44 (average of nine patients) |
| Average pre-treatment endoscopic score | 3.88 (average of eight patients) |
| Average post-treatment endoscopic score | 0.00 (average of two patients) |
| Average pre-treatment histological score | 6.25 (average of eight patients) |
| Average post-treatment histological score | N/A (Patients all refused biopsy |

No adverse effects attributable to acemannan were observed at any time during the study. Some patients who were quite experienced with their own disease expression reported they were virtually free of pain and symptoms within 2-5 days. In others, particularly those with focal segmental disease (Crohn's and ileitis), the effects of acemannan were slower and less dramatic. All patients refused the post-treatment biopsy, and only two patients accepted post-treatment endoscopy. The following reasons were given by the patients: (1) these procedures are uncomfortable, and (2) the cost was not justified because of their improved condition.

Two patients were episodic in their intake of acemannan, taking it only when symptomatic. Both reported relief of symptoms in 24 to 88 hours after consuming the medication; however, mild symptoms returned in 4-6 weeks after discontinuance of acemannan treatment. Subsequently, 2-3 days of acemannan treatment again relieved symptoms. Acemannan provided dramatic clinical improvement in the acute inflammatory phase of the disease.

EXAMPLE 23

Monocyte/Macrophage Uptake of $C^{14}$-Labeled Acemannan In Vitro

A pilot study was devised using human peripheral blood monocyte cell cultures and carbon$^{14}$-labeled acemannan to track the incorporation or absorption of acemannan into a biological system. The purpose of this experiment was to determine if the uptake of $^{14}C$-labeled acemannan by normal, peripheral monocyte/macrophage cells is: (a) detectible, (b) constant with time or sporadic, (c) cytotoxic at 0.5% w/v concentration and (d) ultimately, whether monocyte/macrophage cells are capable of concentrating acemannan within the cell itself to levels higher than that presented in the culture environment (media).

A. Preparation of $^{14}$C-Labeled Acemannan

One hundred mg of $^{14}$C-labeled acemannan, derived from the gel of Aloe plants grown in $^{14}$C-labeled carbon dioxide, was weighed into a 50 mL polypropylene centrifuge tube. Five mL of sterile water containing the antibiotic, gentamicin, 100 μgm/mL, was added. Five days later, 5 mL of RPMI 1640+Ab+1% Hepes+10% heat-inactivated fetal calf serum+1% L-glutamine was added to the tube. Solubilization with occasional agitation was allowed to proceed at refrigerator temperatures (5° C.) for 1 week. On day 14, 2.5 mL of the 10 mg/mL acemannan solution was dispensed to each of three sterile 10 mL tubes. Two and one-half mL of monocyte/macrophage medium was added to give a final concentration of 5 mg/mL in 5 mL. These 5 mL preparations were then transferred to each of three 25-cm$^2$ tissue culture flasks containing approximately 500,000 monocyte/macrophage cells of peripheral blood origin.

B. Preparation of Peripheral Blood Monocyte/Macrophage Cells

Blood collected in EDTA was obtained from the hematology department of Dallas/Ft. Worth Medical Center. Only blood with normal hematological parameters was used. The two-step separation method using Sepratech Corporation's Sepracell-MN TM system was followed to obtain a relatively pure (88% +9.27) monocyte cell fraction. This suspension was introduced into each of three Corning #25100 25-cm$^2$ tissue culture flasks at a cell density of approximately 750,000 cells per flask. To substantiate the assumed cell mass in the final number of cells in the assay, the cells from two 25-cm$^2$ flasks, each less than 50% confluent, were harvested and counted on a Coulter Model ZM Electronic cell counter. The two flasks yielded approximately 750,000 cells (roughly equivalent to one confluent flask). Eighty percent confluence would have equaled 625,000 cells; therefore, the 500,000 cells/flask used in the calculation seems reasonable. Monocyte/macrophage medium (RPMI 1640 +antibiotic +1% Hepes +10% heat-inactivated fetal calf serum +1% L-glutamine) was added, and the flasks were maintained in a 5% CO$_2$ incubator for 1 week to allow the monocytes to mature into the macrophage form. Medium was replaced once during the week of maturation. On day 7, each flask was copiously washed with fresh monocyte/macrophage medium. The remaining adherent cells, which had attached and enlarged to occupy approximately 80% of the surface area, were aspirated free of media. The 5 mL aliquots of $^{14}$C-labeled acemannan at a concentration of 5 mg/mL were added to each of the three flasks of adherent cells.

C. Preparation Steps for Assay of $^{14}$C-Uptake by Liquid Scintillation

At 24, 48 and 72 hours, each of the three assay flasks was treated as follows: the acemannan solution was removed from the incubation flask and transferred to a 15 mL sterile conical polystyrene centrifuge tube (supernatant tube). The flask was washed with 1 mL of monocyte/macrophage medium with agitation by rotation to collect any residual acemannan solution. The wash was added to the supernatant tube. One milliliter of trypan blue (0.01% in PBS) was added to the flask, allowed to stand for 5 minutes and the flask was examined by phase contrast microscopy. Less than 1% of the adherent cells was positive (non-viable). The trypan blue was removed. The flask was washed once with 1 mL Pucks EDTA, which was discarded. Pucks EDTA was added to the flask of adherent cells and allowed to stand at 30° C. for approximately 3 minutes. The Pucks EDTA was removed and transferred to a 15 mL sterile conical polystyrene centrifuge tube (cell mass tube). Three milliliters of Pucks, with 12.5% trypsin, was added 1 mL at a time to release adherent cells. A rubber policeman was used after the last addition to scrape the remaining adherent cells free. The final volume of cells in Pucks/trypsin was approximately 4 mL in the cell mass tube. Examination of flasks by phase contrast microscopy showed very few cells remaining in the flask. All $^{14}$C-labeled acemannan solution not used in the cell flasks was retained as a control.

All tubes plus flasks were refrigerated pending acid hydrolysis. All tubes were frozen and lyophilized on a Virtis lyophilizer. Five milliliters of 2N TFA (trifluoroacetic acid) was added to the lyophilized material. After becoming solubilized, the contents of each tube was transferred to Pyrex glass, screw top tubes and put into a 70° C. oven. The contents were allowed to digest and reduce in volume until approximately 1 mL remained. The tubes were removed from the oven and allowed to cool, with multiple vortex mixes to dissolve dry material on tube walls. At this point, the tubes contained approximately 1 mL of dark liquid and some insoluble sediment. Two-tenths milliliters of 35% $H_2O_2$ was added to each of the supernatant tubes and to the control tube. The tubes were allowed to stand capped in the dark overnight to obtain maximum decoloration of the residual liquid containing the digested $^{14}$C. Three-tenths milliliters of water was added to each of the cell mass tubes. The entire contents of each of the seven digestion tubes was transferred to a 20 mL glass scintillation vial. Each digest tube was washed with 3 mL of ScintiVerse Bio HP (Fisher Scientific) scintillation fluid, which was added to the scintillation vial. The vial was then filled to capacity (20 mL) with scintillation fluid. The contents were mixed by shaking on several different occasions, then set aside to stand overnight to allow the insoluble material to settle out before counting in a Packard Minaxi Tri-Carb 4000 series beta counter.

Based on the CPM of the seven samples, calculations were made on a percent uptake of available $^{14}$C-labeled acemannan. These percents were plotted against time. From the calculations and plot, it was determined that uptake by the cell mass was 2.0% at 24 hours, 5.16% at 48 hours and 3.48% at 72 hours. Further calculations were made by totaling the seven sample counts. This total represents the entire 100 mg of $^{14}$C-labeled acemannan used. The total counts were used to derive the milligram quantity of each cell mass counted. The highest uptake, 5.16% at 48 hours, was equal to 0.97 mg of labeled acemannan absorbed or ingested by the monocyte/macrophage cell mass. Estimating that there were 500,000 viable cells in the cell mass, each with an uptake of $^{14}$C-labeled acemannan, there was an estimated $1.9 \times 10^{-6}$ mg of acemannan in each cell. Geigy Scientific Tables, Vol. 3, p. 205, states the volume of a monocyte to be 470 femtoliters (fL). The volume of each cell was calculated as 500 fL since monocytes enlarge into macrophages. This produces a w/v value of 3800 femtograms/fL. Comparing this to the w/v value of the $^{14}$C-labeled acemannan, 5 mg/mL, yields a ratio of concentration in the cells 760 times greater than in the supernatant.

Based on this pilot study, detectable amounts of $^{14}$C-labeled acemannan at a concentration of 5 mg/mL was not cytotoxic to the monocyte/macrophage cells, and the digested cell mass, in weight/volume (w/v) terms, was 760 times greater than the w/v of the digested acemannan solution.

EXAMPLE 24

Preliminary Investigation of the In Vitro Effects of Acemannan on Measles Virus

Measles virus was incubated with various concentrations of acemannan prior to the addition of measles virus to susceptible cultures of VERO cells. The purpose of this experiment was to determine if acemannan would inhibit infection or inactivate measles virus treated with acemannan prior to introduction into a susceptible cell culture. Acemannan-treated virus did not infect the VERO monolayer as evidenced by the absence of cytopathic effects (CPE) of the virus at a threshold concentration of 2.5 mg/mL. Complete absence of CPE was achieved at 5 mg/mL of acemannan in the virus inoculum.

African Green Monkey kidney cells (VERO cells) were used as the target cells. Measles virus was titrated to obtain a plaque count of 30–50 plaques/mL (20 TCID units/0.05 mL) on the virus/cell monolayer. Acemannan at different concentrations was then introduced into media containing this fixed amount of virus. The concentrations of acemannan were made in complete tissue culture medium. An aliquot of rubella attenuated virus vaccine was used for each titration. The mixtures were pre-incubated at 30° C. for one-half hour and added to previously prepared VERO monolayer in tissue culture chambers.

Figure 24:
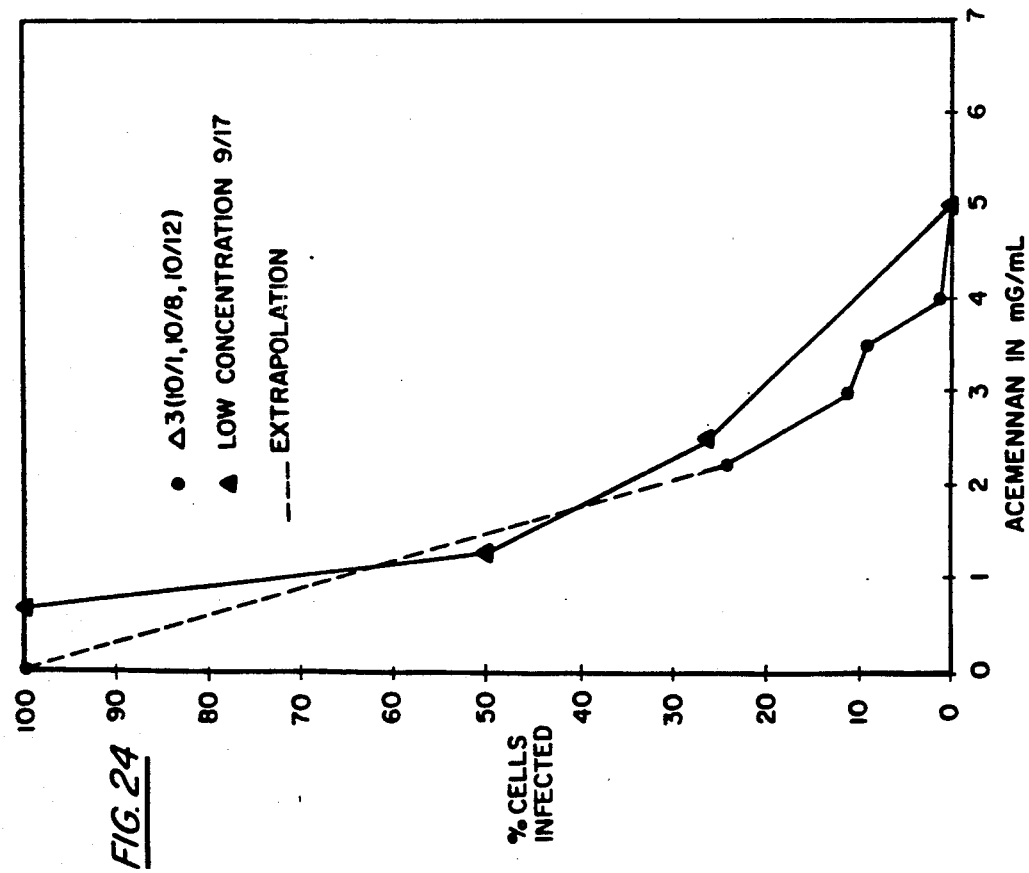
FIG. 24 is a graph showing titration of acemannan to establish the concentration required to block CPE in a VERO cell/measles virus/acemannan in bitro system.

The results of combining measles virus with various concentrations of acemannan incubated five full days on confluent VERO cell monolayers are provided in FIG. 24 and Table 18.

Repetitious challenges with various concentrations of acemannan showed that a protective concentration was achieved between 2 mg/mL and 4 mg/mL, this being a transition zone for inhibiting measles virus infectivity. Note Table 18. It is apparent that the 5 mg/mL acemannan level consistently provided protection to the VERO cell monolayer challenged with measles virus pretreated with acemannan.

TABLE 18

Effect of Acemannan Concentration

| DATE | DIL | VIRUS DOSE | # | 1 | 2 | 3 | 4 | AV. | % INF. |
|---|---|---|---|---|---|---|---|---|---|
| 09/10/86 | 5 | 25 | 34 | 1(?) | | | | 1 | 0 |
| | 2.5 | 12.5 | 30 | 0 | | | | 0 | 0 |
| | 1.25 | 6.25 | 16 | 1 | | | | 1 | 6.25 |
| | 0.625 | 3.125 | 12 | 4 | | | | 4 | 33.3 |
| 09/17/86 | 5 | 20 | 100+ | 0 | 0 | | | 0 | 0 |
| | 2.5 | | | 20 | 30 | | | 25 | 25 |
| | 1.25 | | | 60 | 30 | | | 50 | 50 |
| | 0.625 | | | 100+ | 100+ | | | 100+ | 100 |
| | 0.3125 | | | 100+ | 100+ | | | 100+ | 100 |
| | 0.1525 | | | 100+ | 100+ | | | 100+ | 100 |
| 10/08/86 | 5.0 | 20 | 100+ | 0 | 1 | | | 1 | <1 |
| | 4.5 | | | 1 | 0 | | | 1 | <1 |
| | 4.0 | | | 0 | 2 | | | 2 | — |
| | 3.5 | | | 10 | 1 | | | 5.5 | 6 |
| | 3.0 | | | 9 | 0 | | | 4.5 | 5 |
| | 2.5 | | | 5 | 9 | | | 7 | 7 |
| | 2.3 | 10 | | 0 | | | | 0 | 0 |
| | 1.0 | 5 | | 0 | | | | 0 | 0 |
| 10/12/86 | 5.0 | 20 | 5.5 | 0 | 0 | 0 | 0 | 0 | 0 |
| | 4.5 | | | 0 | 0 | 0 | 0 | 0 | 0 |
| | 4.0 | | | 0 | 0 | 0 | 0 | 0 | 0 |
| | 3.5 | | | 1 | 0 | 0 | 0 | 0.25 | 4.5 |
| | 3.0 | | | 1 | 0 | 0 | 0 | 0.25 | 4.5 |
| | 2.5 | | | 0 | 1 | 1 | 1 | 0.75 | 11 |
| | 2.5 | 12.5 | | 0 | 0 | 0 | 0 | 0 | 0 |
| | 1.0 | 6.25 | | 0 | 0 | 0 | 0 | 0 | 0 |
| 10/01/86 | 5.0 | 20 | 6.0 | 0 | 0 | | | 0 | 0 |
| | 4.5 | | | 0 | 0 | | | 0 | 0 |
| | 4.0 | | | 0 | 0 | | | 0 | 0 |
| | 3.5 | | | 0 | 2 | | | 1 | 16.6 |
| | 3.0 | | | 1 | 2 | | | 1.5 | 25 |
| | 2.5 | | | 3 | 3 | | | 3 | 50 |
| | 2.5 | 10 | | 0 | 0 | | | 0 | 0 |
| | 1.0 | 5 | | 0 | 0 | | | 0 | 0 |

The effect of acemannan on measles virus in this pilot study was evaluated by comparing untreated (VERO cell control), measles virus (positive control) and measles virus-infected cells treated with 5 mg/mL acemannan. There was a significant reduction in plaque formation in the acemannan-pretreated virus-infected cultures as determined by plaque count assay. Complete prevention of infection of cultures by the treated virus was achieved when the virus was pretreated with 5 mg/mL acemannan.

EXAMPLE 25

Ability of Acemannan to Reverse Measles Virus Infection in VERO Cell Culture

VERO cells were incubated with medium containing 40 TCID/mL of measles virus for various periods of time (0.5 to 6 hours) prior to the addition of 5 mg/mL of acemannan. Incubation with acemannan after cells were exposed to the measles virus did not protect the VERO cells from infection.

VERO cells were incubated for 0.5 to 6 hours with media containing 40 TCID/mL of measles virus. The VERO cells were then washed with fresh medium to remove any unbound virus. Medium containing 5 mg/mL acemannan was then added to the cultures, and the cultures were examined for cytopathology after five days.

Figure 25:
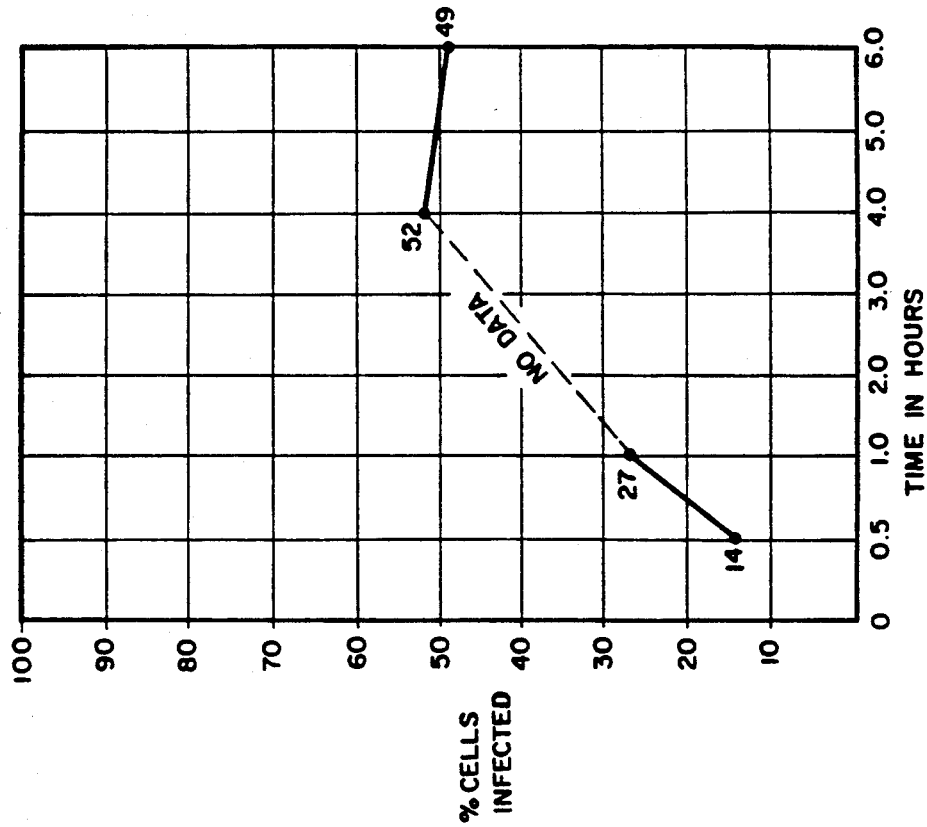
FIG. 25 is a graph showing the infection rate of VERO cells by measles virus in hours of time.

The results of this experiment are indicated in FIG. 25 and Table 19:

TABLE 19

Effect of Brief Incubation of VERO Cells Measles Virus Followed by Acemannan Treatment

| DATE | DIL | VIRUS DOSE | # | 1 | 2 | 3 | 4 | AV. | INF. |
|---|---|---|---|---|---|---|---|---|---|
| 09/29/86 | 5.0 | 0t 20 | L/0.5 mL | 25 | 25 | 25 | 10 | 21.25 | 100 |
| | 5.0 | 0.5 hr | | 1 | 3 | 10 | 2 | 3.5 | 16 |
| | 5.0 | 1.0 hr | | 1 | 10 | 9 | 16 | 9 | 42 |
| | 5.0 | 4.0 hr | | 8 | 21 | 25 | 7 | 15.25 | 71 |
| | 5.0 | 6.0 hr | | X | 18 | 15 | 4 | 12.3 | 58 |
| 11/14/86 | 5.0 | 0t 20 | L/0.5 mL | 13 | 17 | 17 | 25 | 18 | 100 |
| | | 0.5 hr | | acemannan bacterially contaminated | | | | | |
| | | 1.0 hr | | | | | | | |
| | | 4.0 hr | | | | | | | |
| | | 6.0 hr | | | | | | | |
| 06/10/87 | 5.0 | 0t 20 | L/0.5 mL | 100 | 100 | | | 100 | 100 |
| | 5.0 | 0.5 hr | | 8 | 8 | 10 | 9 | 8.75 | 14 |
| | 5.0 | 1.0 hr | | 10 | 8 | 9 | 11 | 9.5 | 15.5 |
| | 5.0 | 4.0 hr | | 25 | 15 | 25 | 30 | 23.75 | 38 |
| | 5.0 | 6.0 hr | | 24 | 24 | 25 | 31 | 26 | 42 |
| Average of two assays for graph | | | | 0t = 100% | | | | | |
| | | | | 0.5 hr = 15% | | | | | |
| | | | | 1.0 hr = 28.8% | | | | | |
| | | | | 4.0 hr = 54.5% | | | | | |
| | | | | 6.0 hr = 50% | | | | | |

There was a lower infection rate noted in 0.5- and 1-hour acemannan pre-incubation cultures. There was no clinically significant protection of VERO cells noted on the cultures post-incubated for longer periods with acemannan.

VERO cells pre-incubated with measles virus were not significantly protected from infection by addition of 5 mg/mL of acemannan after the infection period had ended.

EXAMPLE 26

Project to Determine the Effectiveness of Carrisyn TM Extract on the Induction of a Protective Immune Response in Commercial Poultry Nationally, losses from disease and management-related problems cost the poultry industry in excess of $2.0 billion annually. Infectious agents such as infectious bursal disease virus (IBDV), a retrovirus that induces mortality and/or morbidity associated with immunosuppression, cause severe economic losses to the poultry industry. IBDV specifically targets precursor B-cells in the bursa of Fabricius leading to selective destruction of the humoral arm of the immune system. This causes an immunosuppressed state akin to AIDS (Acquired Immune Deficiency Syndrome).

The poultry industry routinely vaccinates flocks against IBDV by oral administration of live virus or by subcutaneous injection of inactivated virus. Although both methods of vaccination may effectively elicit an immune response, inherent problems associated with the use of vaccines are introduced. Live virus vaccines are more effective in the elicitation of a protective immune response to a specific strain, but the virus itself may revert to virulence, or replication of the vaccine strain may cause transient immunosuppression leading to increased susceptibility of the flock to secondary pathogens. Killed virus vaccines do not have the same problems as those associated with live virus vaccines, but immune responsiveness is diminished and is dose dependent. Numerous alternatives to vaccination that involve complicated high-tech solutions are being evaluated, but directed modulation of the immune response, by inclusion of an additional component in a killed-virus vaccine, represents a potentially simple solution.

Carrisyn TM extract, on the basis of preliminary observations, acts as an immunomodulator, and this project was designed to determine if this compound stimulates the immune response to a killed infectious bursal disease virus (IBDV)

A. Animals

Chicks hatched from eggs purchased from SPAFAS, Inc. were used for all experiments. Eggs were hatched, and day-old chicks were placed in Horsfall Units.

B. Antigen

BursaVac K (oil emulsion)—Carrisyn TM extract used: Lot #80226-001; resuspended at 0.5, 1 or 2 mg/ml (see experimental design)

C. Experimental Design

Study #1 (Group 1). For Study #1 25 2-week old chicks were divided into five groups. The chicks in each group were vaccinated as follows:
Group 1 —control, sham inoculated
Group 2 —inoculated subcutaneously in the back area with 0.5 ml of oil emulsion vaccine
Group 3 —inoculated subcutaneously with 0.25 ml of oil emulsion vaccine (Bio-Burs K; Key Vet., Gainesville, GA) mixed with the 0.25 ml of Carrisyn TM extract (0.5 mg/ml) suspended in water (1:1)
Group 4 —inoculated orally with 0.5 ml of microcapsules suspended in acidic water
Group 5 —inoculated orally with 0.5 ml of microcapsules suspended in acidic water with 0.5 mg of Carrisyn TM extract Study #2 (Group 2). For Study #2 117 1-week old SPF chicks were divided into six groups. The chicks in each group were vaccinated as follows:
Group 1 —control, sham inoculated
Group 2 —inoculated subcutaneously over the back with 0.5 ml of Carrisyn TM extract (2 mg/ml) suspended in water
Group 3 —inoculated subcutaneously over the back with 0.5 ml of oil emulsion vaccine (Bio-Burs K; Key Vet., Gainesville, GA)
Group 4 —inoculated subcutaneously over the back with 0.25 ml of oil emulsion vaccine mixed with 0.25 ml of Carrisyn TM extract (1 mg/ml) suspended in water (1:1)
Group 5 —inoculated subcutaneously over the back with 0.25 ml of oil emulsion vaccine mixed with 0.25 ml of Carrisyn TM extract (2 mg/ml) suspended in water (1:1)
Group 6 —inoculated subcutaneously over the back with 0.5 ml of oil emulsion vaccine and over the femoral region with 0.5 ml of Carrisyn TM extract (2 mg/ml) suspended in water For both studies serum was collected from each chick at weekly intervals, and serum IBDV ELISA titers were determined using commercially available AgriTech IBDV ELISA kits. ELISA titers were determined using FlockChek software, a program marketed by AgriTech, Inc.

D. Results

Chicks exhibited no discomfort or side effects as a result of subcutaneous or peros administration of Carrisyn TM extract suspended in water or oil emulsion.

For Study #1 (Group 1) the mean ELISA titers are presented through the sixth week following vaccination in Table 20:

TABLE 20

| | | Immunostimulatory Effects of Carrisyn TM Extract: Study #1 | | | | | |
|---|---|---|---|---|---|---|---|
| | | DAYS POST-VACCINATION | | | | | |
| Group | Presentation of Antigen | 0 | 7 | 14 | 21 | 28 | 35 | 42 |
| | | IBDV ELISA TITERS | | | | | |
| #1 | Cont | 0 | 0 | 0 | 0 | 7 | 107 | 191 |
| #2 | Em | 0 | 0 | 54 | 372 | 556 | 2184 | 983 |
| #3 | Em&Ca | 0 | 5 | 231 | 1142 | 2276 | 4508 | 3101 |
| #4 | Mic | 0 | 0 | 0 | 2 | 5 | 61 | 127 |
| #5 | Mic&Ca | 0 | 0 | 1 | 0 | 13 | 150 | 0 |

Two weeks after the primary vaccination, titers to IBDV started to rise in chicks treated with oil emulsion or oil emulsion supplemented with Carrisyn TM extract. The chicks treated with the oil emulsion vaccine supplemented with Carrisyn TM extract had an overall mean titer approximately 3.9 times higher than those vaccinated with oil emulsion vaccine only. Three weeks after vaccination the chicks were revaccinated, with each chick receiving the same antigen mixture as presented in the primary vaccination. One week after secondary vaccination the difference in the mean titer ratio had increased to approximately 4.1. Thereafter the ratio fell to approximately 2.1 by 2 weeks after the secondary injection, when mean titers for both groups had reached their peak. By 3 weeks after secondary vaccination, mean titers for both vaccinated groups had begun to decrease, but the decrease in titer for chicks vaccinated with oil emulsion alone was more precipitous, with a drop in titer of 55% as compared to 31% for chicks vaccinated with oil emulsion supplemented with Carrisyn TM extract. The maintenance of the higher titer in birds treated with oil emulsion supplemented with Carrisyn TM extract appears due to the prolonged immunostimulatory actions of Carrisyn TM extract, indicative of a prolonged effect of Carrisyn TM extract.

Three weeks after the secondary vaccination chicks from the oil emulsion vaccine group (#2) and the oil emulsion vaccine supplemented with Carrisyn TM extract group (#3) were redivided into two groups (A and B). Group A chicks were challenged with the homologous live vaccine strain, and Group B chicks were challenged with a virulent field strain. Three days after challenge all chicks were necropsied. There was no effect on the immune system in Group A chicks challenged with the vaccine strain. But all Group B chicks had lesions as demonstrated by histopathology. These are the expected results, but if chicks given only a primary vaccination had been challenged, it is likely that a greater preponderance of lesions in the chicks given only the oil emulsion vaccine would have been seen. If the chicks had been vaccinated with the live virus vaccine, lesions in the lymphoid organs would have been seen in chicks resistant to homologous virus challenge.

For Study #2 group sizes and the vaccination protocols were changed. As may be seen from Table 21, results were inconsistent:

TABLE 21

| | Immunostimulatory Effects of Carrisyn TM Extract: Study #2 | | | | |
|---|---|---|---|---|---|
| | | DAYS POST-VACCINATION | | | |
| Group | Presentation of Antigen | 0 | 7 | 14 | Std. Dev. |
| | | IBDV ELISA TITERS | | | |
| #1 | Cont | 0 | 11 | 1 | S.D. 0 |
| #2 | Ca(0.5 mg) | 11 | 37 | 1 | S.D. 0 |
| #3 | Em | 21 | 11 | 181 | S.D. 571 |
| #4 | Em&0.25 mgCa | 46 | 0 | 5 | S.D. 11 |
| #5 | Em&0.5 mgCa | 188 | 0 | 279 | S.D. 824 |
| #6 | EmRt&0.5 mgCaLt | 36 | 79 | 504 | S.D. 842 |

It was initially noticed that there were differences in the birds two weeks after injection. There were more runts than would be expected, and some of the sites where the chicks were banded appeared to be infected; they had pressure necrosis, which would result in toxin release, in addition to secondary bacterial infection. In an effort to circumvent the latter problem the chicks were rebanded and treated with a topical antibiotic. However, the problems already described would probably cause an overall immunosuppression, which would void the results of this study. Therefore, the experiment was terminated.

In spite of the negative factors associated with Study #2, Carrisyn TM extract caused an overall stimulatory effect of the immune system, which is recognized as an enhanced immune response to test antigens administered at sites remote from the site of Carrisyn TM extract administration. Although the initial impression was that Carrisyn ™ extract had to be mixed with the oil emulsion vaccine, it appears that an enhanced immune response was elicited when the antigen and Carrisyn ™ extract were presented separately as well. This result allows for exploration of alternative vaccination methodologies and applications for this compound.

Carrisyn ™ extract appears to have adjuvant properties. It appeared to increase the persistence or effective presentation of IBDV antigen within the body, possibly leading to release of lymphokines and an enhanced lymphocyte response.

EXAMPLE 27

Malabsorption syndromes in man cause a wasting condition which can eventually result in death. Specific human syndromes such as Sprue and Celiac disease can be ameliorated if certain grains containing complex polysaccharides and enzyme inhibiting peptides are withdrawn from the diet. The result of this diet change is to reduce the symptoms. The major physiological problem that remains for the patient is the maturation arrest of small bowel intestinal mucosa (page 132) due to inhibition in the synthesis of glycoproteins essential for cell maturation. This failure of small bowel interaction reduces absorptive surface area and further results in failure to absorb essential amino acids, fatty acids, minerals, vitamins and other critical molecular substances present in the diet.

Providing additional mannose, a substance required for glycoprotein synthesis, predictably shifts the velocity of $K_{MAX}$ to increase the rate of glycoprotein synthesis. Enzymes synthesis is promoted by the availability of the critical mannose substrate that fosters ribosomal/glycoprotein synthesis by mannose metabolizing enzymes. This increase in glycoprotein synthesis and availability results in small intestine mucosal cell maturation and reduction in symptoms associated with Sprue and Celiac disease. The thermodynamic shift in glycoprotein synthesis has use in other categories of disease with no effective existing therapy.

EXAMPLE 28

Multiple Sclerosis

Multiple sclerosis is a neurological disease of unknown etiology and no effective treatment. Analysis of patient data and demographics indicate the disease is most likely initiated by an infectious agent, probably of viral origin. Analysis of central nervous system lesions, spinal fluid and serum suggest that an autoimmune component is also present. This autoimmune response results in myelin sheath degradation.

The antiviral properties of acemannan noted in tissue cultures, animals, and humans led to the early effort to investigate whether multiple sclerosis would respond to an immune modulating complex polysaccharide. The precipitous and abrupt induction of a clinical remission in five (5) sequential symptomatic patients with independently diagnosed multiple sclerosis has led to this claim of anecdotal observed efficacy.

The rational basis for the above clinical responses are projected as follows:

1. Nonspecific gamma interferon and specific alpha interferon induction against the viral agent through monocyte/macrophage system induction by the acetylated polymannan (acemannan).

2. An activation of desirable effects on the immune humoral and cellular antiviral action of IL-1 production by the monocyte/macrophage system against the causative agent.

3. Interleukin-1 induction by the M/M system has been found to result in a down-regulation of T-8 suppression lymphocytes essential to the elimination of autoimmune tissue destruction.

4. Nerve growth factor (NGF) is released by (8) activated monocytes under induction by LPS. Mannans are the biologically active moiety in L.P.S., as in acemannan. Activated neurite processes extend from neurons to induce Schwann cells to produce myelin to encircle and restore neural impulse transmission to injured and non-functional nerves. This latter sequence of events, induced by acemannan, undoubtedly is active in the repair and restoration of multiple sclerosis patient nerve function. The return of nerve function in M.S. patients treated with acemannan follows the classical progression of return of nerve function seen in selected cord lesions applied experimentally in animals and seen in human trauma.

POSSIBLE USES FOR CARRISYN ™ EXTRACT

Acemannan has a number of possible uses. The first use is expected to be as an immunostimulant demonstrating antitumor activity against: equine sarcoid, bovine ocular squamous cell carcinoma, canine mammary tumor, canine venereal sarcoma, feline leukemia, and bovine leukemia; against parasitic and infectious skin diseases: staphylococcal pyoderma, demodecosis, sarcoptic mange, ear mites, and flea allergy; against infectious and allergic respiratory disease: bovine shipping fever, chronic cough in horses, and equine epistaxis; against infectious digestive diseases: viral and bacterial diarrheas, cryptosporidiosis, and coccidiosis; and against other systemic diseases: toxoplasmosis.

Acemannan's second expected use is as an adjuvant wherein the Carrisyn ™ extract may promote the response to any inactivated vaccine containing viral, parasitic or bacterial antigens including the following: cattle vaccines —infectious bovine rhinotracheitis, parainfluenza 3, respiratory syncytial virus, bovine virus diarrhea, rotavirus, coronavirus, bluetongue, rabies, clostridial diseases, footrot, pinkeye, anaplasmosis, babesiosis, pasteurellosis, salmonellosis, colibacillosis, corynebacterium sp., vibriosis, brucellosis, leptospirosis, hemophilus somnus, foot and mouth disease, papillomavirus, and staphylococcal mastitis; sheep vaccines—clostridial diseases, footrot, rabies, foot and mouth disease, erysipelas, louping ill, and caseous lymphadenitis; swine vaccines—parvovirus, erysipelas, transmissible gastroenteritis, pseudorabies, bordetella bronchiseptica, colibacillosis, pasteurellosis, foot and mouth disease, clostridial diseases, leptospirosis, and hemophilus pleuropneumonia; equine vaccines—influenza, rhinopneumonitis, tetanus, strangles, equine arteritis, Eastern, Western and Venezuelan encephalitis, and rabies; feline vaccines—rhinotracheitis, feline leukemia, calicivirus, chlamydiosis, lentivirus, panleukemia, rabies, and infectious peritonitis; canine vaccines—distemper, adenovirus (types 1 and 2), rabies, parvovirus, leptospirosis, parainfluenza, coronavirus, measles, rhodococcus equi, tetanus, and rabies; and avian vaccines—infectious bursal disease, Newcastle disease, infectious bronchitis, infectious laryngotracheitis, Mareks disease, and coccidiosis.

Acemannan's third expected use is as an antiviral agent wherein Carrisyn ™ extract may prevent the replication of any virus that requires glycosylation of its proteins in order to replicate. This has been shown for lentiviruses. It may also be employed to control the replication of: reoviridae including reoviruses, orbiviruses and rotaviruses (examples of these include African horse sickness, and bluetongue; picornaviridae including enteroviruses, rhinoviruses and caliciviruses (examples of these include polioviruses, foot and mouth disease virus, and Coxsackie viruses); togaviruses including the alphaviruses, and flaviviruses (examples of these include the equine encephalitides, and St. Louis encephalitis); orthomyxoviruses (examples of these include the influenza viruses and Newcastle disease virus); paramyxoviruses including morbilliviruses, and pneumoviruses (examples include mumps, measles, parainfluenze, and respiratory syncytial viruses); retroviruses including both oncoviruses and lentiviruses (examples include human immunodeficiency virus and feline leukemia virus); rhabdoviruses (examples include rabies virus and vesicular stomatitis virus); bunyaviruses such as Rift Valley fever; coronaviruses (an example of which is avian infectious bronchitis virus); parvoviruses (examples include canine parvovirus, feline panleukemia and mink enteritis); papovaviruses including papilloma and papovaviruses; adenoviruses; herpesviruses (examples include infectious bovine rhinotracheitis, herpes simplex virus, feline rhinotracheitis, varicella zoster, Epstein Barr virus and cytomegalovirus); poxviruses including the orthopox viruses and the parapoxviruses (examples include vaccinia and variola); and hepatitis viruses (examples include hepatitis A and B).

What is claimed is:

1. A method of activation, induction and enhancement of the production of Interleukin I and prostaglandin $E_2$ in a mammal by monocyte and macrophage peripheral blood adherent cells, comprising:

administering to a mammal an amount of acemannan sufficient to effect monocyte and macrophage stimulation.

2. The method of Claim 1 wherein acemannan is administered orally in the range of about 0.1 mg/kg bwt/day to about 100.0 mg/kg bwt/day, or administered by injection in a range of about 0.001 mg/kg bwt/day to 10 mg/kg bwt/day.

3. A method of stimulating macrophage phagocytosis in a mammal, comprising:

administering to a mammal an amount of acemannan sufficient to effect monocyte and macrophage stimulation.

4. A method of producing an antiviral effect in mammals, comprising:

administering to a mammal an amount of acemannan sufficient to effect monocyte and macrophage stimulation.

5. A method of producing defective virus in humans, comprising:

administering to a human an amount of acemannan sufficient to effect monocyte and macrophage stimulation and alter viral replication metabolism in virus-infected cells.

6. A method of treatment of tumor in a mammal, comprising:

administering to said mammal an amount of acemannan sufficient to effect monocyte and macrophage stimulation, enhance natural killer cell activity, and specific tumor cell lysis by white cells and antibodies.

7. A method of treatment of tumor in a mammal, comprising:

administering to said mammal an amount of acemannan sufficient to effect monocyte and macrophage stimulation, enhance natural killer cell activity, and specific tumor cell lysis by antibodies.

* * * * *

UNITED STATES PATENT AND TRADEMARK OFFICE
CERTIFICATE OF CORRECTION

PATENT NO. : 5,106,616         Page 1 of 3

DATED : April 21, 1992

INVENTOR(S) : McAnalley, et al.

It is certified that error appears in the above-identified patent and that said Letters Patent is hereby corrected as shown below:

Col. 2, line 60, delete "N)" and insert --NO.--.

Column 4, line 14, delete "Leibovic" and insert --Leibovici--;

line 48, after "al.," insert --Nature,--.

Column 6, line 43, delete "Antimirobial" and insert --Antimicrobial--.

Column 10, line 22, change "th" to --the--.

Col. 14, line 6, change "bitro" to --vitro--.

Column 22, line 7, change Il-18" to --Il-1β--;

line 54, between "in" and "to" add --vitro--.

Column 24, line 1, after "medium" add --;--;

line 3, change "$CO_295\%$" to --$CO_2$-95%--.

Column 28, line 38, before "Microtiter Infection Assay" add --C.--.

Column 29, line 19, change "45%" to --43%--;

line 44, change "(GP-12" to --(GP-120--.

UNITED STATES PATENT AND TRADEMARK OFFICE
CERTIFICATE OF CORRECTION

PATENT NO. : 5,106,616

DATED : April 21, 1992

INVENTOR(S) : McAnalley, et al.

It is certified that error appears in the above-identified patent and that said Letters Patent is hereby corrected as shown below:

Column 30, line 24, before "Aliquots" add --Assay:--.

Column 31, line 32, before "effective" add --an--.

Column 38, line 45, change "364"" to --36"--.

Column 40, line 52, change "bottles is" to --bottles are--.

Column 41, line 26, change "tank When" to --tank. When--.

Column 42, line 45, change "-37°C" to --∼37°C--;
            line 63, change "102 0" to --102.0--.

Column 43, line 28, change "uconventionally-cleaned" to --conventionally-cleaned--.

Column 46, line 10, change "both in and" to --both in vivo and--.

Column 52, line 2, after "than" add --10%--.

Column 54, line 40, change "tread" to --trend--;
            line 47, change "of" to --or--.

UNITED STATES PATENT AND TRADEMARK OFFICE
CERTIFICATE OF CORRECTION

PATENT NO. : 5,106,616

DATED : April 21, 1992

INVENTOR(S) : McAnalley, et al.

It is certified that error appears in the above-identified patent and that said Letters Patent is hereby corrected as shown below:

Column 56, line 48, change "24 to 88" to --24 to 48--.
Column 57, line 32, change "(88% + 9.27)" to --(88% $\pm$ 9.27)--.
Column 62, line 41, change "(IBDV)" to --(IBDV) vaccine--.
Column 67, line 16, change "parainfluenze" to --parainfluenza--.

Signed and Sealed this

Fifth Day of October, 1993

BRUCE LEHMAN

*Attesting Officer*   *Commissioner of Patents and Trademarks*